(12) United States Patent
Futami et al.

(10) Patent No.: US 10,837,964 B2
(45) Date of Patent: Nov. 17, 2020

(54) DNA APTAMER BINDING TO CANCER CELL

(71) Applicant: Agency for Science, Technology and Research, Singapore (SG)

(72) Inventors: Kazunobu Futami, Tokyo (JP); Ichiro Hirao, Tokyo (JP); Michiko Hirao, Tokyo (JP)

(73) Assignee: Agency for Science, Technology and Research, Singapore (SG)

( * ) Notice: Subject to any disclaimer, the term of this patent is extended or adjusted under 35 U.S.C. 154(b) by 62 days.

(21) Appl. No.: 15/771,584

(22) PCT Filed: Oct. 25, 2016

(86) PCT No.: PCT/JP2016/081517
§ 371 (c)(1),
(2) Date: Apr. 27, 2018

(87) PCT Pub. No.: WO2017/073535
PCT Pub. Date: May 4, 2017

(65) Prior Publication Data
US 2018/0348220 A1    Dec. 6, 2018

(30) Foreign Application Priority Data
Oct. 30, 2015 (JP) ................. 2015-214591

(51) Int. Cl.
| | | |
|---|---|---|
| *C12N 15/11* | (2006.01) | |
| *G01N 33/574* | (2006.01) | |
| *C12N 15/115* | (2010.01) | |
| *A61K 31/713* | (2006.01) | |
| *A61K 31/711* | (2006.01) | |
| *C12Q 1/6886* | (2018.01) | |

(52) U.S. Cl.
CPC ...... *G01N 33/57415* (2013.01); *A61K 31/711* (2013.01); *A61K 31/713* (2013.01); *C12N 15/111* (2013.01); *C12N 15/115* (2013.01); *G01N 33/574* (2013.01); *C12N 2310/122* (2013.01); *C12N 2310/16* (2013.01); *C12N 2310/33* (2013.01); *C12N 2310/531* (2013.01); *C12N 2320/13* (2013.01); *C12Q 1/6886* (2013.01)

(58) Field of Classification Search
CPC .................................................. C12N 15/115
See application file for complete search history.

(56) References Cited

PUBLICATIONS

Hirao et al, An unnatural hydrophobic base pair system: site-specific incorporation of nucleotide analogs into DNA and RNA, Nature Methods, 2006, vol. 3, No. 9: 729-735 (Year: 2006).*
Acquah et al., "Deploying aptameric sensing technology for rapid pandemic monitoring," Critical Reviews in Biotechnology, Sep. 18, 2015, 36(6):1010-1022.
Meyer et al., "Aptamers: versatile probes for flow cytometry," Appl. Microbiol. Biotechnol., Jul. 10, 2013, 97:7087-7109.
Sefah et al., "Development of DNA aptamers using Cell-SELEX," Nature Protocols, Jun. 3, 2010, 5(6):1169-1185.

* cited by examiner

*Primary Examiner* — Ekaterina Poliakova-Georgantas
(74) *Attorney, Agent, or Firm* — Kilpatrick Townsend & Stockton LLP

(57) ABSTRACT

The purpose of the present invention is to provide an aptamer to a cancer cell, said aptamer being superior to conventional aptamers in binding ability, specificity, and/or stability. To solve this problem, provided is a DNA aptamer binding to a cancer cell, said DNA aptamer containing an artificial base(s).

16 Claims, 37 Drawing Sheets
Specification includes a Sequence Listing.

Fig. 9

14A-MCF7
(37DsDs)
SEQ ID NO: 8

14A-MCF7
(35DsDs)
SEQ ID NO: 9

14A-MCF7mh
(44DsDs)
SEQ ID NO: 10

14A-MCF7mh
SEQ ID NO: 11

14A-MCF7mh
(40DsDs)
SEQ ID NO: 12

14A-MCF7mh
(38DsDs)
SEQ ID NO: 13

Fig. 11
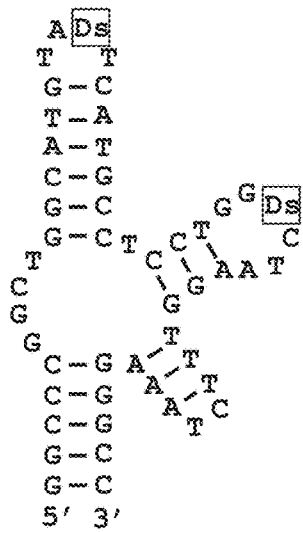
08B-MCF7
(51DsDs)
SEQ ID NO: 20
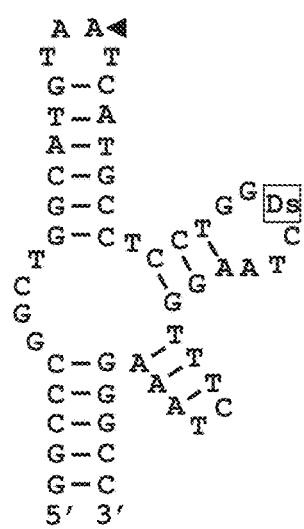
08B-MCF7
(51ADs)
SEQ ID NO: 21
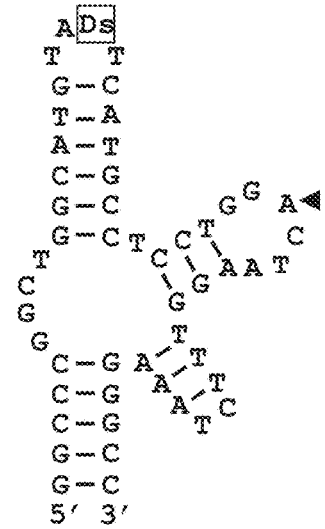
08B-MCF7
(51DsA)
SEQ ID NO: 22
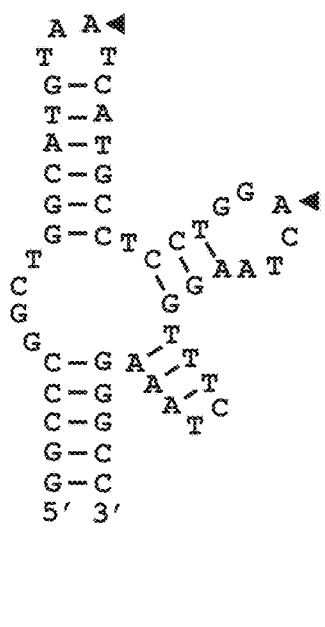
08B-MCF7
(51AA)
SEQ ID NO: 23
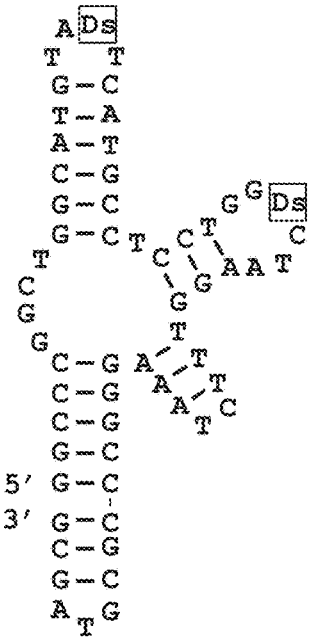
08B-MCF7mh
SEQ ID NO: 24
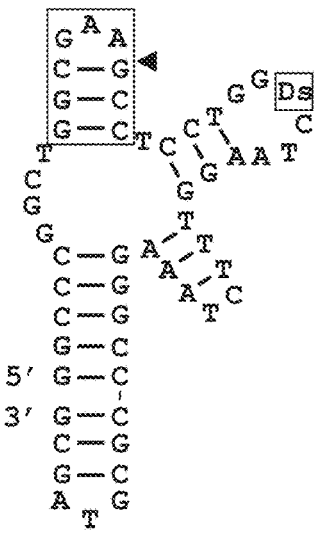
08B-MCF7mh2
SEQ ID NO: 25

Fig. 13
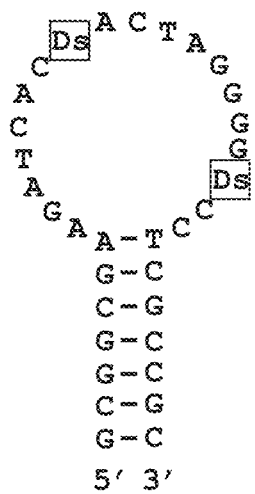
03-T47D
(DsDs)
SEQ ID NO: 29
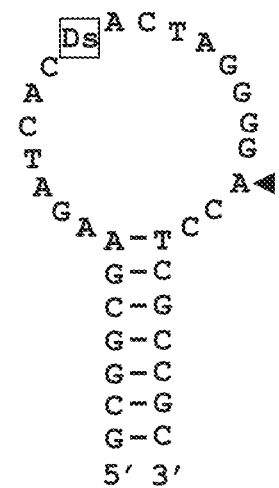
03-T47D
(DsA)
SEQ ID NO: 30
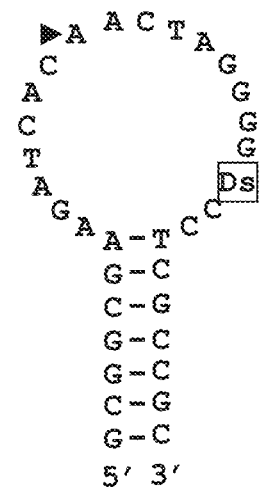
03-T47D
(ADs)
SEQ ID NO: 31
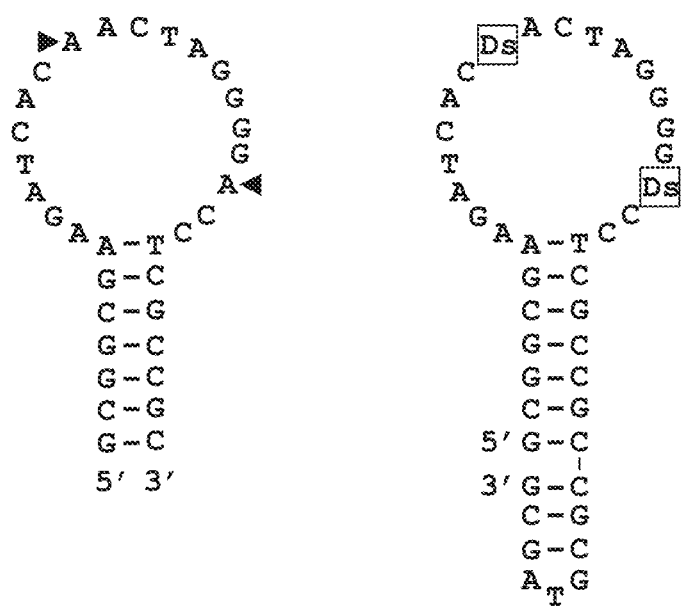

Fig. 15
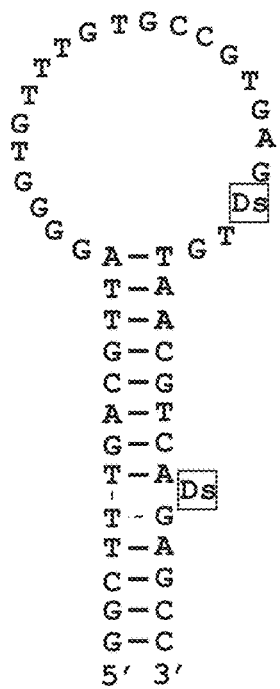
05-MB231
(DsDs)
SEQ ID NO: 36
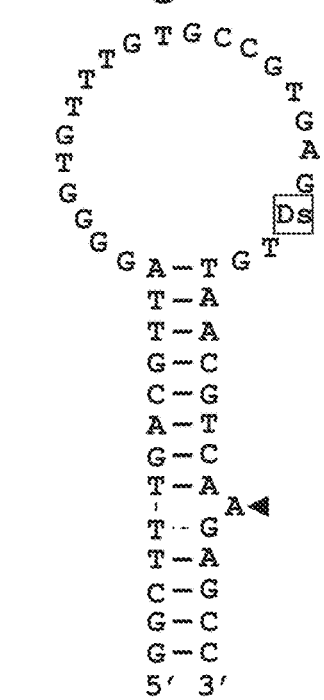
05-MB231
(DsA)
SEQ ID NO: 37
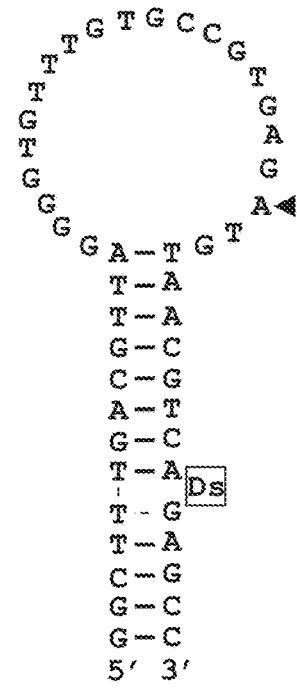
05-MB231
(ADs)
SEQ ID NO: 38
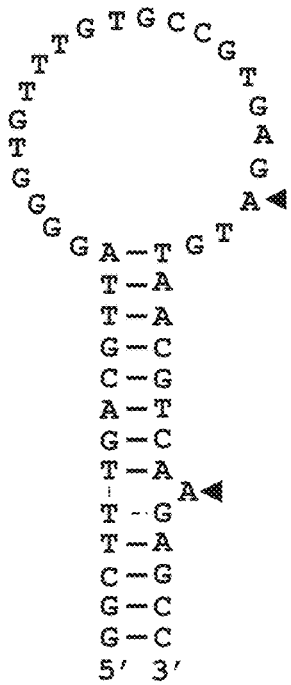
05-MB231
(AA)
SEQ ID NO: 39
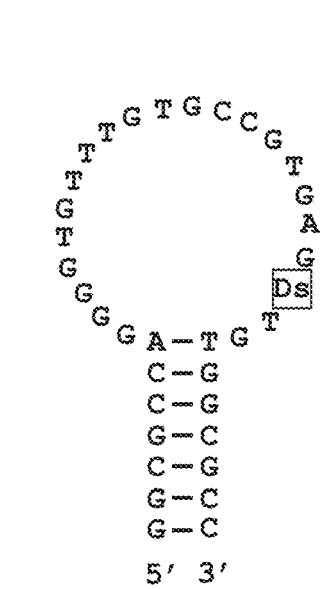
05-MB231GC
SEQ ID NO: 40
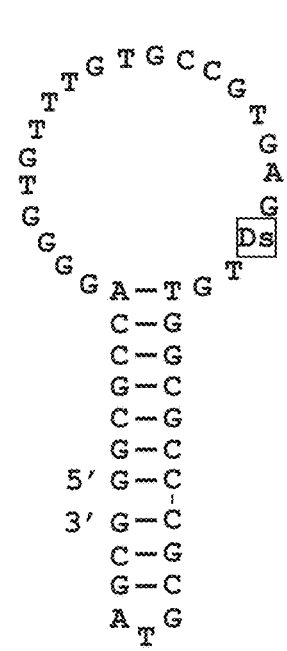
05-MB231GCmh
SEQ ID NO: 41

Fig. 17

```
      C T
    T   C
Ds    T
  G··T
  G··T
  G··T
  T—A
  C—G T C
  C—G A Ds
  G··T
  A—T C A
          A
  C—G C T
  G—C
  C—G
  G—C
  C—G
  C—G
  5'  3'
```
07-MB231
(DsDs)
SEQ ID NO: 44

```
      C T
    T   C
Ds    T
  G··T
  G··T
  G··T
  T—A
  C—G T C
  C—G A A◄
  G··T
  A—T C A
          A
  C—G C T
  G—C
  C—G
  G—C
  C—G
  C—G
  5'  3'
```
07-MB231
(DsA)
SEQ ID NO: 46

```
      C T
    T   C
►A    T
  G··T
  G··T
  G··T
  T—A
  C—G T C
  C—G A Ds
  G··T
  A—T C A
          A
  C—G C T
  G—C
  C—G
  G—C
  C—G
  C—G
  5'  3'
```
07-MB231
(ADs)
SEQ ID NO: 47

```
      C T
    T   C
►A    T
  G··T
  G··T
  G··T
  T—A
  C—G T C
  C—G A A◄
  G··T
  A—T C A
          A
  C—G C T
  G—C
  C—G
  G—C
  C—G
  C—G
  5'  3'
```
07-MB231(AA)
SEQ ID NO: 48

```
      C T
    T   C
Ds    T
  G··T
  G··T
  G··T
  T—A
  C—G T C
  C—G A Ds
  G··T
  A—T C A
          A
  C—G C T
  G—C
  C—G
  G—C
  C—G
5' C—G
3' G—C
  C—G
  G—C
  A   G
   T
```
07-MB231mh
SEQ ID NO: 45

Fig. 25
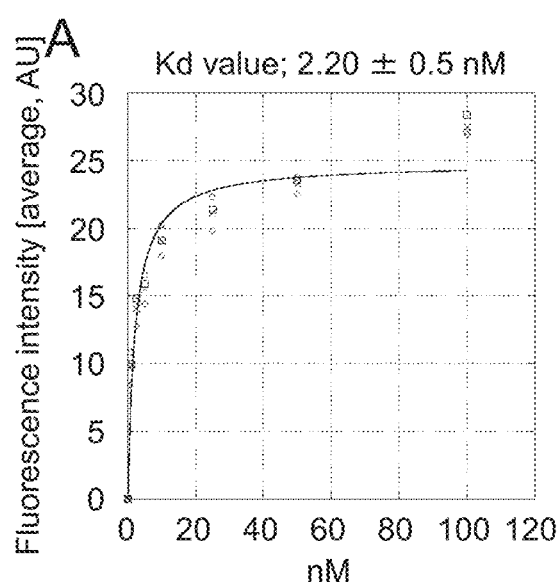
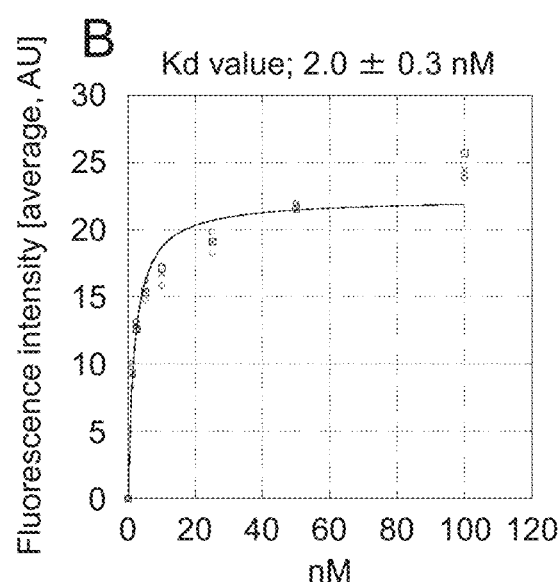

Fig. 33-2
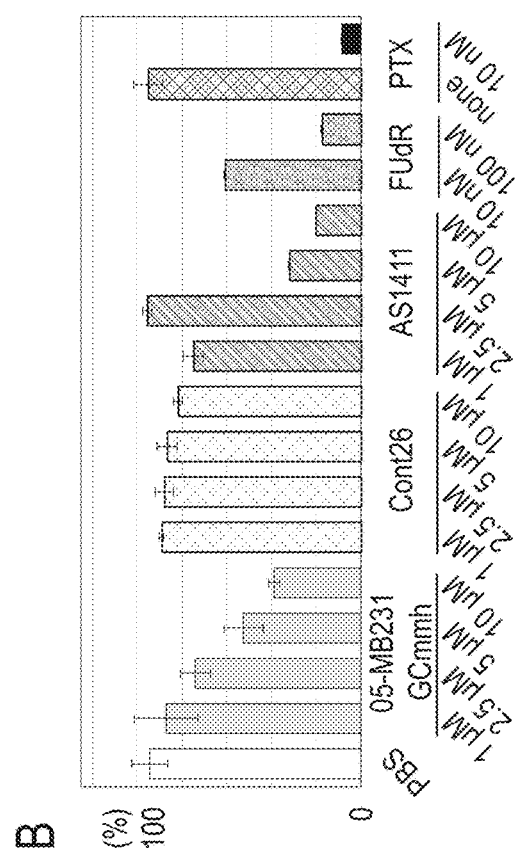
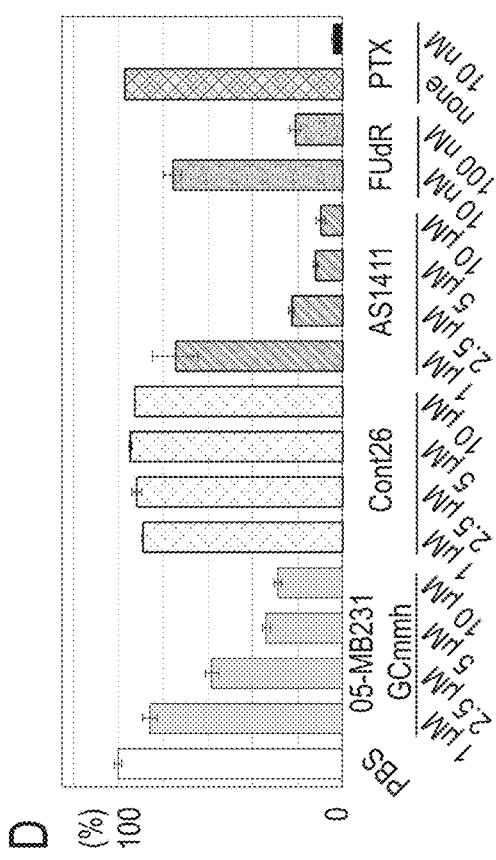
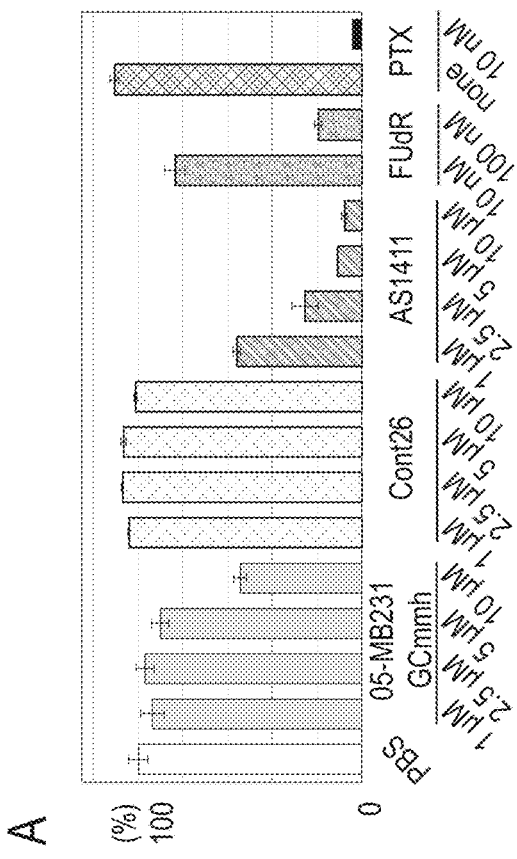
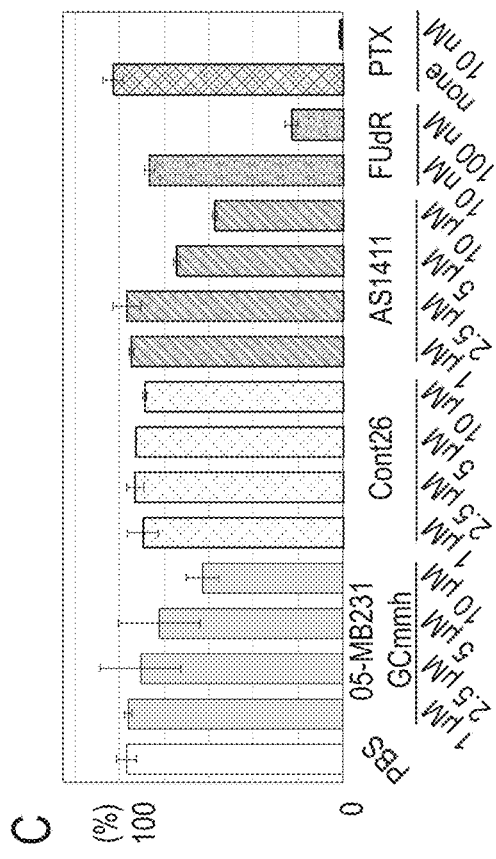

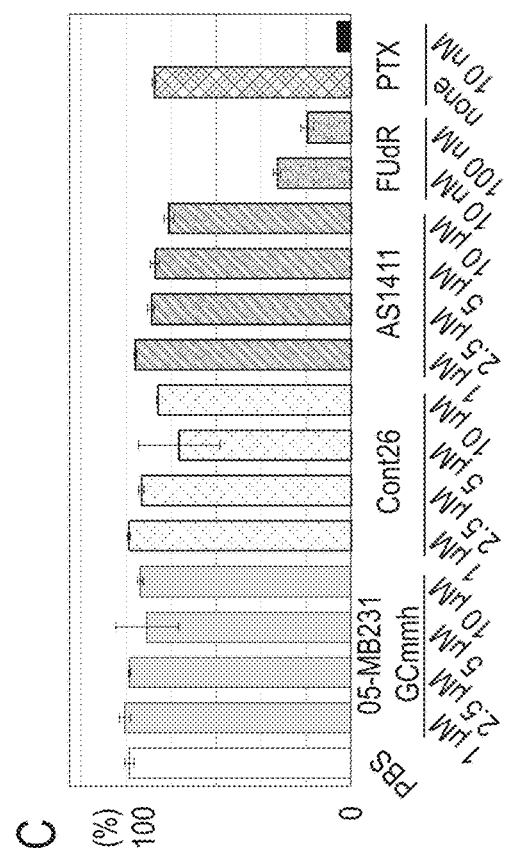
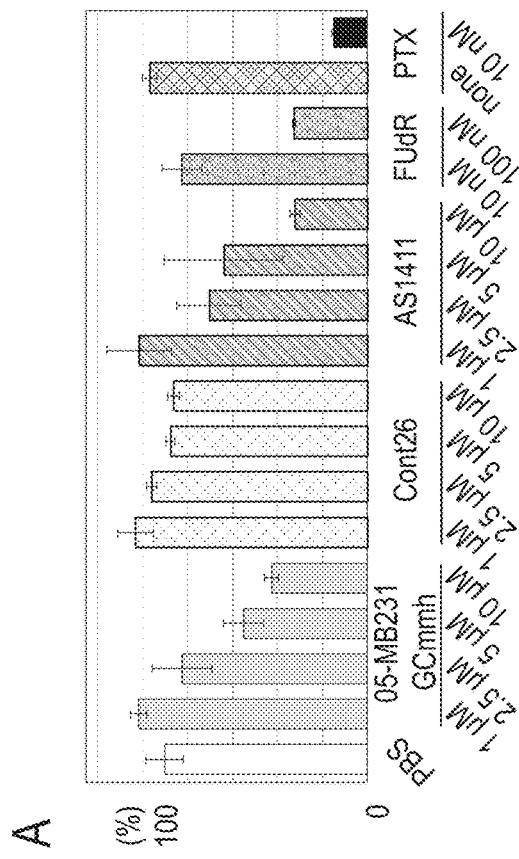
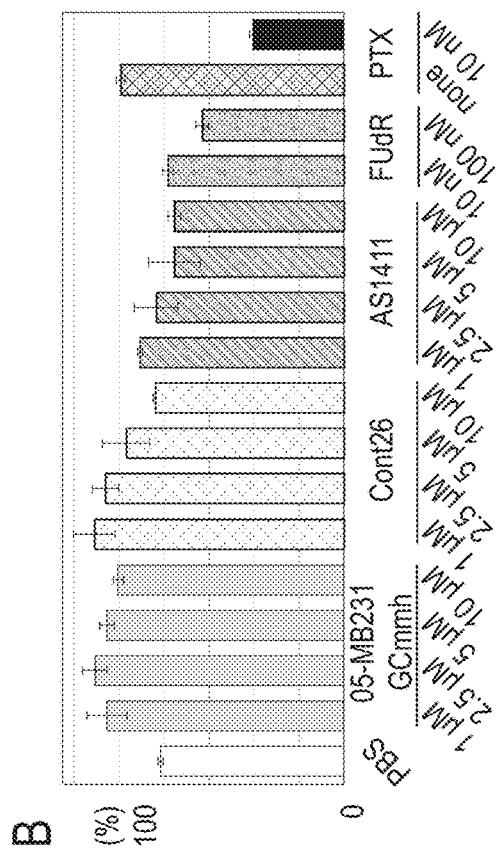
Fig. 33-3

DNA APTAMER BINDING TO CANCER CELL

CROSS-REFERENCE TO RELATED APPLICATIONS

This application is a National Stage application of PCT/JP2016/081517, filed Oct. 25, 2016, which claims priority from Japanese application JP 2015-214591, filed Oct. 30, 2015.

TECHNICAL FIELD

The present invention relates to a DNA aptamer that binds to a cancer cell comprising artificial nucleotide(s), a pharmaceutical composition comprising the DNA aptamer, and a method of detecting a cancer cell using the DNA aptamer.

BACKGROUND ART

A nucleic acid fragment having binding activity to a target molecule is referred to as a "nucleic acid aptamer," and extensive applications thereof as nucleic acid pharmaceuticals to medical practice have been expected. In recent years, cells and viruses are found to be able to serve as targets of nucleic acid aptamers, in addition to low-molecular-weight substances and proteins (Non Patent Literature 1 to Non Patent Literature 3). By targeting an whole cell, aptamers that recognize surface molecules peculiar to the cell, such as receptors and glycosylated chains expressed on the cell surface, can be obtained.

In recent years, also, it has become a general practice of cancer treatment to prepare a treatment regimen on the basis of the state of tumor marker expression. However, a variety of known markers is not enough at present. If a novel marker capable of identifying various types of cancers is discovered by obtaining a nucleic acid aptamer targeting a cancer cell, it can be useful for early diagnosis of various types of cancers. Further, if a nucleic acid aptamer that specifically targets and binds to a cancer cell is obtained, it can be applied to an anticancer agent or a drug delivery system (DDS). However, conventional nucleic acid aptamers were not sufficient in terms of binding ability, specificity, stability, and the like for use in the field of medical practice, including treatment and diagnosis.

CITATION LIST

Non-Patent Literature

Non-Patent Literature 1: Sefah, K. et al., Nature protocols 2010, 5, 6, pp. 1169-1185 Non-Patent Literature 2: Acquah, C. et al., Critical Reviews in Biotechnology 2015, early Online (Doi: 10.3109/07388551.2015.1083940)
Non-Patent Literature 3: Meyer, M. et al., Appl. Microbiol. Biotechnol., 2013, 97, pp. 7097-7109

SUMMARY OF INVENTION

Technical Problem

Accordingly, development of an aptamer reacting with cancer cells, which exhibits higher binding ability, specificity, and/or safety than a conventional nucleic acid aptamer is demanded.

Solution to Problem

The present inventors performed the Cell-SELEX technique using the library containing artificial nucleotides developed by the present inventors (WO2013/073602) while targeting breast-cancer-derived three types of cell lines (MCF7, MDA-MB-231, and T-47D), and they obtained a plurality of DNA aptamers containing artificial nucleotide(s). Each DNA aptamer containing artificial nucleotide(s) bound to the target cell line very firmly, and no or little affinity with non-cancer cells was observed. The DNA aptamers obtained were further examined and found to comprise DNA aptamers binding to most cancer cells and DNA aptamers exhibiting different binding ability depending on cancer cell lines. The former type of the DNA aptamers is very useful in terms of the ability to detect a wide variety of cancer cells, while the latter type of the DNA aptamers is very useful in terms of the applicability to cancer cell classification.

The present invention is completed based on the above finding and it includes the following aspects.

(1) A DNA aptamer that binds to a cancer cell comprising the nucleotide sequence (i) or (ii) below:

(i) (a) a nucleotide sequence represented by $N_1N_2N_3N_4N_5$AGGGGTGTTTGTGCCGTGAGN$_{26}$TGTN$_{30}$N$_{31}$N$_{32}$N$_{33}$N$_{34}$ (SEQ ID NO: 35), wherein $N_1$ to $N_5$ each independently represent G, T, A, or C, $N_{26}$ represents 7-(2-thienyl)-3H-imidazo[4,5-b]pyridin-3-yl, $N_{30}$ forms a base pair with $N_5$, $N_{31}$ forms a base pair with $N_4$, $N_{32}$ forms a base pair with $N_3$, $N_{33}$ forms a base pair with $N_2$, and $N_{34}$ forms a base pair with $N_1$), or (b) a nucleotide sequence in which one or several nucleotides are added, deleted, and/or substituted in the nucleotide sequence (i)(a) at position(s) other than the position of $N_{26}$: or (ii) (a) a nucleotide sequence represented by $N_1N_2N_3N_4N_5N_6$GATCACN$_{13}$N$_{14}$CTAGGGGN$_{22}$CCN$_{25}$N$_{26}$N$_{27}$N$_{28}$N$_{29}$N$_{30}$N$_{31}$ (SEQ ID NO: 28), wherein, $N_1$ to $N_6$, $N_{14}$, and $N_{25}$ each independently represent G, T, A, or C, $N_{13}$ and $N_{22}$ each represent 7-(2-thienyl)-3H-imidazo[4,5-b]pyridin-3-yl, $N_{26}$ forms a base pair with $N_4$, $N_{29}$ forms a base pair with $N_3$, $N_{30}$ forms a base pair with $N_2$, $N_{31}$ forms a base pair with $N_1$, and $N_{27}$ and $N_{21}$ each independently represent G, T, A, or C or none), or (b) a nucleotide sequence in which one or several nucleotides are added, deleted, and/or substituted in the nucleotide sequence (ii)(a) at position (s) other than the positions of $N_{13}$ and $N_{22}$.

(2) The DNA aptamer according to (1), wherein the nucleotide sequence (i) (a) or (ii) (a) further comprises 1 to 5 GC base-pairs at its terminus.

(3) The DNA aptamer according to (1) or (2), wherein the base pair is a GC base-pair.

(4) The DNA aptamer according to any of (1) to (3), wherein the one or several nucleotides of the nucleotide sequence (i) (b) are added, deleted, and/or substituted at position(s) 1 to 5 or 30 to 34 of SEQ ID NO: 35.

(5) The DNA aptamer according to any of (1) to (3), wherein the one or several nucleotides of the nucleotide sequence (ii) (b) are added, deleted, and/or substituted at position(s) 1 to 6, 14, or 25 to 31 of SEQ ID NO: 28.

(6) The DNA aptamer according to (1) or (2), wherein the nucleotide sequence (i) (a) is the sequence as shown in SEQ ID NO: 36, 37, or 40.

(7) The DNA aptamer according to (1) or (2), wherein the nucleotide sequence (ii) (a) is the sequence as shown in SEQ ID NO: 29.

(8) The DNA aptamer according to any of (1) to (7), which further comprises a mini-hairpin structure at the 3'-terminus, wherein the mini-hairpin structure is composed of the nucleic acid regions (A) to (C) below sequentially ligated from the 5'-terminus toward the 3'-terminus:

(A) a first nucleic acid region consisting of 2 to 5 arbitrary nucleotides;

(B) a second nucleic acid region consisting of a nucleotide sequence of GNA or GNNA (wherein each "N" independently represents any of G, T, A, or C); and (C) a third nucleic acid region consisting of a nucleotide sequence complementary to the first nucleic acid region, wherein the first nucleic acid region and the third nucleic acid region form a stem portion by base pairing, and the second nucleic acid region forms a loop portion.

(9) A DNA aptamer that binds to a breast cancer cell comprising any of the nucleotide sequences (1) to (IV) below:

(I) (a) a nucleotide sequence represented by $N_1N_2N_3N_4N_5N_6CAGCCTGGGN_{16}TN_{18}TCTTTN_{24}$ $AGTCN_9AN_{31}TTCAN_{36}TCGN_{40}N_{41}N_{42}N_{43}N_{44}N_{45}$ (SEQ ID NO: 43), wherein $N_1$ to $N_6$, $N_{18}$, $N_{24}$, $N_{31}$, and $N_{36}$ each independently represent G, T. A, or C, $N_{16}$ represents 7-(2-thienyl)-3H-imidazo[4,5-b]pyridin-3-yl, $N_{29}$ represents 7-(2-thienyl)-3H-imidazo[4,5-b]pyridin-3-yl, G, T, A, or C, $N_{40}$ forms a base pair with $N_6$, $N_{41}$ forms a base pair with $N_5$, $N_{42}$ forms a base pair with $N_4$, $N_{43}$ forms a base pair with $N_3$, $N_{44}$ forms a base pair with $N_2$, and $N_{45}$ forms a base pair with $N_1$, or (b) a nucleotide sequence in which one or several nucleotides are added, deleted, and/or substituted in the nucleotide sequence (I)(a) at position(s) other than the position of $N_{16}$;

(II) (a) a nucleotide sequence represented by $N_1N_2N_3N_4CN_6N_7TCGAACTGN_{16}N_{17}ATGAGN_{23}GTN_2$ $N_{27}N_2N_{29}N_{30}N_{31}$ (SEQ ID NO: 2), wherein $N_1$ to $N_4$, $N_7$, $N_{16}$, $N_{23}$, $N_{26}$, and $N_{31}$ each independently represent G, T, A, or C, $N_6$ represents 7-(2-thienyl)-3H-imidazo[4,5-b]pyridin-3-yl, G, T, A, or C, $N_{17}$ represents 7-(2-thienyl)-3H-imidazo[4,5-b]pyridin-3-yl. $N_{17}$ forms a base pair with $N_3$, $N_{28}$ forms a base pair with $N_2$, and $N_{29}$ and $N_{30}$ each independently represent G, T, A, or C or none, or (b) a nucleotide sequence in which one or several nucleotides are added, deleted, and/or substituted in the nucleotide sequence (II)(a) at position (s) other than the position of $N_{17}$;

(III) (a) a nucleotide sequence represented by $N_1N_2N_3CCGGCTN_{10}N_{11}N_{12}N_{13}N_{14}N_{15}N_{16}N_{17}N_{18}N_{19}N_{20}$ $N_{21}N_{22}N_{23}N_{24}N_{25}TCCTGGN_{32}N_{33}TA$ $AGGTTTCTAAN_{46}N_{47}N_{48}N_{49}N_{50}N_{51}$ (SEQ ID NO: 18), wherein $N_1$ to $N_3$, $N_{13}$ to $N_{17}$, $N_{19}$ to $N_{22}$, $N_{33}$, $N_{46}$ to $N_{48}$, and $N_{50}$ each independently represent G, T, A, or C, $N_{10}$ to $N_{12}$ and $N_{23}$ to $N_{25}$ each independently represent G, T, A, or C or none, $N_{18}$ represents 7-(2-thienyl)-3H-imidazo[4,5-b] pyridin-3-yl, G, T, A, or C or none, $N_{32}$ represents 7-(2-thienyl)-3H-imidazo[4,5-b]pyridin-3-yl, $N_{49}$ forms a base pair with $N_3$, $N_{51}$ forms a base pair with $N_1$, and 3 or more of $N_{10}$ to $N_{15}$ form base pairs with 3 or more of $N_{20}$ to $N_{25}$, or (b) a nucleotide sequence in which one or several nucleotides are added, deleted, and/or substituted in the nucleotide sequence (III)(a) at position(s) other than the position of $N_{32}$; and (IV) (a) nucleotide sequence represented by $N_1N_2N_3TCTTAAGTTTAN_{15}AN_{17}N_{18}TN_{20}N_{21}N_{22}N_{23}$ $TN_{25}N_{26}N_2N_{28}N_{29}N_{30}N_{31}N_{32}TN_{34}GGGCGTTTTAAN_{46}$ $N_{47}N_{48}N_{49}$ (SEQ ID NO: 50), wherein $N_1$ to $N_3$, $N_{15}$, $N_{17}$, $N_{20}$ to $N_{23}$, $N_{25}$ to $N_{29}$, $N_{31}$ to $N_{32}$, $N_{34}$, and $N_{46}$ each independently represent G, T, A, or C, $N_{18}$ and $N_{30}$ each represent 7-(2-thienyl)-3H-imidazo[4,5-b]pyridin-3-yl, $N_{47}$ forms a base pair with $N_3$, $N_{48}$ forms a base pair with $N_2$, and $N_{49}$ forms a base pair with $N_1$, or (b) a nucleotide sequence in which one or several nucleotides are added, deleted, and/or substituted in the nucleotide sequence (IV)(a) at position(s) other than the position(s) of $N_{18}$ and $N_{30}$.

(10) The DNA aptamer according to (9), wherein the nucleotide sequence of (I) (a), (II) (a), (III) (a), or (IV) (a) further comprises 1 to 5 GC base-pairs at its terminus.

(11) The DNA aptamer according to (9) or (10), wherein the base pair is a GC base-pair.

(12) The DNA aptamer according to any one of claims 9 to 11, wherein the one or several nucleotides of the nucleotide sequence (1) (b) are added, deleted, and/or substituted at position(s) 1 to 6, 18, 24, 29, 31, 36, or 40 to 45 of SEQ ID NO: 43.

(13) The DNA aptamer according to any one of claims 9 to 11, wherein the one or several nucleotides of the nucleotide sequence (II) (b) are added, deleted, and/or substituted at position(s) 1 to 4, 6 to 7, 16, 23, or 26 to 31 of SEQ ID NO: 2.

(14) The DNA aptamer according to any one of claims 9 to 11, wherein the one or several nucleotides of the nucleotide sequence (III) (b) are added, deleted, and/or substituted at position(s) 1 to 3, 10 to 25, 33, or 46 to 51 of SEQ ID NO: 18.

(15) The DNA aptamer according to any one of claims 9 to 11, wherein the one or several nucleotides of the nucleotide sequence (IV) (b) are added, deleted, and/or substituted at position(s) 1 to 3, 15, 17, 20 to 23, 25 to 29, 31 to 32, 34, or 46 to 49 of SEQ ID NO: 50.

(16) The DNA aptamer according to (9) or (10), wherein the nucleotide sequence of (I) (a) is the sequence as shown in SEQ ID NO: 44 or 46.

(17) The DNA aptamer according to (9) or (10), wherein the nucleotide sequence of (II) (a) is the sequence as shown in any of SEQ ID NOs: 3 to 5, 8 to 9, and 14 to 16.

(18) The DNA aptamer according to (9) or (10), wherein the nucleotide sequence of (111) (a) is the sequence as shown in any of SEQ ID NOs: 20, 21, and 26.

(19) The DNA aptamer according to (9) or (10), wherein the nucleotide sequence of (IV) (a) is the sequence as shown in SEQ ID NO: 51.

(20) The DNA aptamer according to any of (9) to (19), which further comprises a mini-hairpin structure at the 3'-terminus, wherein the mini-hairpin structure is composed of nucleic acid regions (A) to (C) below sequentially ligated from the 5'-terminus toward the 3'-terminus:

(A) a first nucleic acid region consisting of 2 to 5 arbitrary nucleotides:

(B) a second nucleic acid region consisting of a nucleotide sequence GNA or GNNA (wherein each "N" independently represents any of G, T, A, or C); and (C) a third nucleic acid region consisting of a nucleotide sequence complementary to the first nucleic acid region, wherein the first nucleic acid region and the third nucleic acid region form a stem portion by base pairing, and the second nucleic acid region forms a loop portion.

(21) A cancer detecting agent comprising the DNA aptamer according to any of (1) to (20).

(22) A cancer cell detecting kit comprising the DNA aptamer according to any of (1) to (20).

(23) A pharmaceutical composition comprising the DNA aptamer according to any of (1) to (20).

(24) An anticancer agent consisting of the DNA aptamer comprising the nucleotide sequence (i) (a) or (b) according to any of (1) to (8).

(25) A pharmaceutical composition for delivering a drug to a cancer cell comprising the DNA aptamer according to any of (1) to (20) and a drug.

(26) A method for detecting cancer cells comprising:
a step of contacting a sample containing cells obtained from a subject with the DNA aptamer according to any one of (1) to (8); and
a step of detecting cancer cells based on the binding between the sample and the DNA aptamer.

(27) A method for detecting a breast cancer cell comprising:
a step of contacting a sample containing cells obtained from a subject with the DNA aptamer according to any of (9) to (20); and
a step of detecting breast cancer cells based on the binding between the sample and the DNA aptamer.

(28) A method for classifying cancer cells obtained from a subject comprising:
a step of contacting cancer cells obtained from a subject with the DNA aptamer according to any of (1) to (20);
a step of determining the presence or absence of the binding between the cancer cells and the DNA aptamer, or measuring the strength of the binding; and
a process of classifying cancer cells based on the presence or absence of the binding, or the strength of the binding.

(29) A method for classifying breast cancer cells obtained from a subject comprising:
a step of contacting breast cancer cells obtained from a subject with the DNA aptamer according to any of (9) to (20);
a step of determining the presence or absence of the binding between the breast cancer cells and the DNA aptamer, or measuring the strength of the binding; and
a step of classifying breast cancer cells based on the presence or absence of the binding, or the strength of the binding.

(30) The method according to (29), wherein the step of contacting comprises contacting breast cancer cells obtained from a subject with 2 or more DNA aptamers selected from at least 2 groups among the 4 groups (I) to (IV) according to any one of (9) to (20).

This description includes the disclosure of Japanese Patent Application No. 2015-214591, to which present application claims priority.

Advantageous Effects of Invention

The present invention provides a DNA aptamer binding to cancer cells that has higher binding ability, specificity, and/or stability than conventional nucleic acid aptamers. The present invention also provides a method for assisting diagnosis of affliction with a cancer, a method for detecting a cancer, and a pharmaceutical composition for treatment and/or prevention of a cancer with the use of the DNA aptamer of the present invention.

BRIEF DESCRIPTION OF DRAWINGS

FIG. 9 shows the sequences of the DNA aptamers used in Example 4 and the putative secondary structures. On the basis of 14A-MCF7 (53DsDs), respective 8 nucleotides were removed from the 5'-terminus and the 3'-terminus; i.e., 16 nucleotides were removed therefrom in total, to design 14A-MCF7 (37DsDs) (SEQ ID NO: 8), a bulge structure of AG was removed from 14A-MCF7 (37DsDs) and several terminal stems were substituted with GC pairs to design 14A-MCF7 (35DsDs) (SEQ ID NO: 9), a mini-hairpin structure was added to the 3'-terminus of 14A-MCF7 (35DsDs) to design 14A-MCF7mh (44DsDs) (SEQ ID NO: 10), and 1, 2, and 3 GC pairs were removed from the stem structure to design 14A-MCF7mh (SEQ ID NO: 11), 14A-MCF7mh (40DsDs) (SEQ ID NO: 12), and 14A-MCF7mh (38DsDs) (SEQ ID NO: 13), respectively. Ds is marked as boxed.

FIG. 11 shows the sequences of the DNA aptamers used in Example 5 and its putative secondary structures. On the basis of 08B-MCF7 (51DsDs) (SEQ ID NO: 20), Ds at position 18 was substituted with A to design 08B-MCF7 (51ADs) (SEQ ID NO: 21), Ds at position 32 was substituted with A to design 08B-MCF7 (51DsA) (SEQ ID NO: 22), Ds at positions 18 and 32 were each substituted with A to design 08B-MCF7 (51AA) (SEQ ID NO: 23), a mini-hairpin structure was added to 08B-MCF7 (51DsDs) to design 08B-MCF7mh (SEQ ID NO: 24), and the internal stem-loop structure of 08B-MCF7mh was substituted with the mini-hairpin structure to design 08B-MCF7mh2 (SEQ ID NO: 25). Ds is marked as boxed, a position at which Ds has been substituted with A is shown by an arrow head, and a position at which the stem-loop structure was substituted with the mini-hairpin structure is boxed with an arrow head.

FIG. 13 shows the sequences of the DNA aptamers used in Example 6 and its putative secondary structures. On the basis of 03-T47D (DsDs) (SEQ ID NO: 29). Ds at position 24 was substituted with A to design 03-T47D (DsA) (SEQ ID NO: 30), Ds at position 15 was substituted with A to design 03-T47D (ADs) (SEQ ID NO: 31), Ds at positions 15 and 24 were each substituted with A to design 03-T47D (AA) (SEQ ID NO: 32), and a mini-hairpin structure was added to the terminus of 03-T47D (DsDs) to design 03-T47Dmh (SEQ ID NO: 33). Ds is boxed and a position at which Ds was substituted with A is shown by an arrow head.

FIG. 15 shows the sequences of the DNA aptamers used in Example 7 and its putative secondary structures. On the basis of 05-MB231 (DsDs) (SEQ ID NO: 36). Ds at position 44 was substituted with A to design 05-MB231 (DsA) (SEQ ID NO: 37), Ds at position 33 was substituted with A to design 05-MB231 (ADs) (SEQ ID NO: 38), Ds at positions 33 and 44 were each substituted with A to design 05-MB231 (AA) (SEQ ID NO: 39), a part of the terminal sequence of 05-MB231 (DsDs) was removed and a part of the stem was substituted with a GC base-pair to design 05-MB231GC (SEQ ID NO: 40), and a mini-hairpin structure was added to 05-MB231GC to design 05-MB231GCmh (SEQ ID NO: 41). Ds is marked as boxed and a position at which Ds has been substituted with A is shown by an arrow head.

FIG. 17 shows the sequences of the DNA aptamers used in Example 8 and its putative secondary structures. On the basis of 07-MB231 (DsDs) (SEQ ID NO: 44), Ds at position 28 was substituted with A to design 07-MB231 (DsA) (SEQ ID NO: 46), Ds at position 15 was substituted with A to design 07-MB231 (ADs) (SEQ ID NO: 47), Ds at positions 15 and 28 were each substituted with A to design 07-MB231 (AA) (SEQ ID NO: 48), and a mini-hairpin structure was added to the terminus of 07-MB231 to design 07-MB231mh (SEQ ID NO: 45). Ds is marked as boxed and a position at which Ds was substituted with A is shown by an arrow head.

FIG. 25 shows the results of measurement of the Kd values of 07-MB231 (DsDs) and its modified form analized by a flow cytometry. A horizontal axis represents the concentration of the DNA aptamer and a vertical axis represents the fluorescence intensity. A shows the results of 07-MB231 (DsDs) and B shows the results of 07-MB231mh.

FIG. 32-1 shows the effects of non-labeled 08B-MCF7mh and 14A-MCF7mh and other drugs on the growth of target cancer cells (MCF7) (A, C) and non-cancer cells (MCF10A) (B, D). FUdR represents floxuridine and PTX represents Paclitaxel. N.A. (Not available) indicates that measurement was not performed.

FIG. 32-2 shows the effect of non-labeled 05-MB231GCmh and 07-MB231mh and other drugs on the growth of target cancer cells (MB231) (A, C) and non-cancer cells (MCF10A) (B, D). FUdR represents floxuridine and PTX represents Paclitaxel.

FIG. 32-3 shows the effects of non-labeled 03-T47Dmh and other drugs on the growth of target cancer cells (T47D) (A) and non-cancer cells (MCF10A) (B). FUdR represents floxuridine and PTX represents Paclitaxel.

FIG. 33-1 shows the effects of the non-labeled 05-MB231GCmmh aptamer and other drugs on the growth of various cancer cells (A: MCF7; B: T47D: C: MDA-MB231: D: MDA-MB453). FUdR represents floxuridine and PTX represents Paclitaxel.

FIG. 33-2 shows the effects of the non-labeled 05-MB231GCmmh aptamer and other drugs on the growth of various cancer cells (A: MIAPaCa-2; B: PC-3; C: HCT116; and D: A549). FUdR represents floxuridine and PTX represents Paclitaxel.

FIG. 33-3 shows the effects of the non-labeled 05-MB231GCmmh aptamer and other drugs on the growth of cancer cells (KG-1) (A) and non-cancer cells (B: MCF10A; C: HUVEC). FUdR represents floxuridine and PTX represents Paclitaxel.

DESCRIPTION OF EMBODIMENTS

1. Definition

Figure 1:
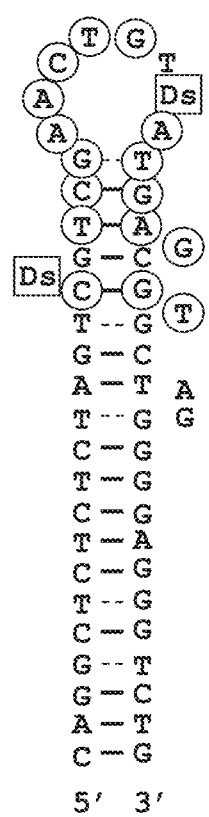
FIG. 1 shows the sequence and the putative secondary structure of the DNA aptamer (14A-MCF7) (SEQ ID NO: 4) selected by Cell-SELEX targeting MCF7 cells. A base found to have a degree of conservation of 85% or higher in a second selection is circled and an artificial base (Ds) is boxed. In the figure, bold lines indicate bases capable of forming Watson-Crick base pairs, dotted lines indicate bases capable of forming non-Watson-Crick base pairs, and solid lines indicate base linkage via phosphodiester bond. Bold lines, dotted lines, and solid lines are used in the same manner in FIGS. 2 to 7, 9, 11, 13, 15, 17, and 19 below.
Figure 2:
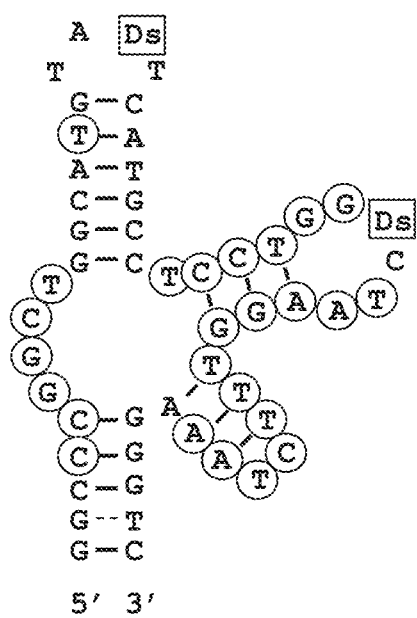
FIG. 2 shows the sequence of the DNA aptamer (08B-MCF7) (SEQ ID NO: 17) selected by Cell-SELEX targeting MCF7 cells and the putative secondary structure. A base found to have a degree of conservation of 85% or higher in a second selection is circled and a Ds is boxed.

Definitions of general terms used herein are described below.

The term "nucleic acid" or "nucleic acid molecule" used herein refers to, in principle, a biopolymer composing nucleotides as composing units bound each other via phosphodiester bond.

The term "natural nucleotide" used herein refers to a nucleotide that exists in nature. Examples thereof include DNA composed of deoxyribonucleotides comprising any natural bases selected from among adenine, guanine, cytosine, and thymine, RNA composed of ribonucleotides comprising any natural bases selected from among adenine, guanine, cytosine, and thymine, and a combination thereof.

The term "un-natural nucleotide" used herein refers to a nucleotide composed of artificial bases that does not exist in nature. Phosphoric acid groups and sugars constituting the un-natural nucleotide according to the present invention are structurally identical to the phosphoric acid groups and sugars constituting a natural nucleotide.

The term "artificial base" or "base analog" used herein refers to an artificially constructed chemical substance having properties similar to those of a natural base constituting a natural nucleotide. As with the case of a natural base, it has a base analog capable of forming an artificial base pair therewith (hereafter, referred to as a "complementary artificial base." The term "artificial base pairing" used herein refers to base pairing formed of a pair of complementary artificial bases, in the same ways natural bases such as adenine and thymine, adenine and uracil, or guanine and cytosine. The term "artificial base pairing" encompasses chemical bonding via a hydrogen bond as observed in base pairing between natural bases, physical bonding via molecular structure-based interlocking between artificial bases, and stacking effects via hydrophobic interaction.

"Properties similar to those of natural bases" of an artificial base include properties capable of replication or transcription (including reverse transcription) of nucleic acids aided by complementarity caused by artificial base pairing. As with the case of natural bases, artificial bases have exclusive selectivity in artificial base pairing. In the presence of an un-natural nucleotide comprising a pair of complementary artificial bases in a substrate nucleotide, accordingly, a nucleic acid molecule comprising an un-natural nucleotide can also be accurately replicated or transcribed as with a natural nucleotide based on complementarity between artificial bases. In the presence of an un-natural nucleotide, accordingly, a DNA molecule can be amplified by nucleic acid amplification, such as PCR.

Specific examples of the artificial bases include 7-(2-thienyl)-3H-imidazo[4,5-b]pyridin-3-yl (referred to as "Ds" herein), 2-nitropyrrol-1-yl (referred to as "Pn" herein), 2-formyl-1H-pyrrol-1-yl (referred to as "Pa" herein), 2-amino-imidazo[1,2-a]-1,3,5-triazin-4(8H)-one (referred to as "P" herein), 6-amino-5-nitro-2(1H)-pyridone (referred to as "Z" herein), 6-methylisoquinoline-1(2H)-thione (referred to as "5SICS" herein), 3-methoxynaphthalen-2-yl (referred to as "NaM" herein), and 2-methoxy-4-methylphenyl (referred to as "MMO2" herein). Among these artificial bases, examples of complementary artificial bases of Ds include Pn and Pa, an example of a complementary artificial base of P is Z, and examples of complementary artificial bases of 5SICS include NaM and MMO2.

When a substrate does not comprise an un-natural nucleotide having complementary artificial base, at the time of replication or transcription, an artificial base can undergo alternative base pairing with a natural base having similar structure and/or property with the complementary artificial base. In such a case, an un-natural nucleotide in the template nucleic acid molecule will be substituted with a natural nucleotide after replication or transcription. For example, Ds is known to be substituted with A or T.

The term "modified base" used herein refers to an artificially and chemically modified base. Examples of modified bases include modified pyrimidine, such as 5-hydroxycytosine, 5-fluorouracil, 4-thiouracil, 5-(3-indole-2-ethyl)uracil, and 5-(4-hydroxyphenyl-2-ethyl)uracil), modified purine, such as 6-methyladenine and 6-thioguanosine, and other heterocyclic bases.

The term "DNA aptamer" used herein refers to an aptamer composed of DNAs. A DNA aptamer is a ligand molecule that firmly and specifically binds to a target molecule through a conformational structure formed based on a secondary and a tertiary structure of a single-stranded nucleic acid molecule via a hydrogen bond or other means. When a DNA aptamer has an ability of specifically inhibiting or suppressing functions such as physiological activity of a target molecule, such DNA aptamer can serve as a functional inhibitor of a target molecule. The term "functional inhibition of a target molecule" used herein refers to inhibition or suppression of biological functions, such as catalytic activity, function of gene expression regulation (including regulation of transcription, translation, and transportation), and regulation of apoptosis of a target molecule.

The term "target molecule" used herein refers to a substance that can be bound by a DNA aptamer. The type of target molecule is not specifically limited, provided that it is a biological substance which can be bound by a DNA aptamer. Examples thereof include a peptide (an oligopeptide or polypeptide), a nucleic acid, a lipid, a sugar (including a sugar chain), a low-molecular-weight compound, a naturally-occurring substance, a chemically synthesized substance, a gene recombinant substance, a cell, and a virus. Preferable substances include cancer cells and proteins expressed in cancer cells.

The term "base pair" used herein refers to a Watson-Crick base pair; i.e., an AT pair or GC pair, unless otherwise specified.

The term "mini-hairpin structure" used herein refers to a structure comprising the 3 DNA nucleic acid regions described below: i.e., a first nucleic acid region, a second nucleic acid region, and a third nucleic acid region, sequentially ligated from the 5'-terminus toward the 3'-terminus. Mini-hairpin-shaped DNA may improve heat stability of the DNA aptamer by enhancing degradation resistance against a nuclease and/or increasing a Tm value of the DNA aptamer.

The "first nucleic acid region" is a nucleic acid region consisting of 2 to 5 arbitrary nucleotides. The nucleotide is a deoxyribonucleotide comprising a base selected from among guanine (G), adenine (A), cytosine (C), and thymine (T). A base constituting the nucleic acid region is preferably guanine or cytosine. This is because when the first nucleic acid region forms a stem structure with the third nucleic acid region described below, a Tm value elevates as the GC content increases, and the stem structure can be maintained stably. Accordingly, most preferably, the full-length nucleotide sequence of the first nucleic acid region is composed of G and/or C.

The "second nucleic acid region" is a nucleic acid region consisting of a nucleotide sequence 5'-GNA-3' or 5'-GNNA-3'. In the sequence, each "N" is a natural base (G, A, T, or C) such as T.

The "third nucleic acid region" is a nucleic acid region consisting of a nucleotide sequence complementary to the first nucleic acid region. Accordingly, the nucleotide sequence of the third nucleic acid region is determined based on the nucleotide sequence of the first nucleic acid region, and the first nucleic acid region forms base pairing with the third nucleic acid region in the molecule. As a result, the first nucleic acid region and the third nucleic acid region form a completely base-paired stem portion, and the second nucleic acid region flanked by the first nucleic acid region and the third nucleic acid region forms loop portions therewith, and, as a whole, mini-hairpin-shaped DNA consisting of 7 to 14 nucleotides is formed. An example of mini-hairpin-shaped DNA is DNA consisting of a nucleotide sequence CGCG-TAGCG (SEQ ID NO: 83).

2. DNA Aptamer Binding to Cancer Cells

In one aspect, the present invention relates to a DNA aptamer that binds to cancer cells comprising the nucleotide sequences (i) (a)-(b) or (ii) (a)-(b) below.

The nucleotide sequence (i) (a) is represented by: $N_1 N_2 N_3 N_4 N_5 AGGGGTGTTTGTGCCGTGAGN_{26}TGTN_{30} N_{31}N_{32}N_{33}N_{34}$ (SEQ ID NO: 35), wherein $N_1$ to $N_5$ each independently represent G, T, A, or C, and $N_{26}$ represents 7-(2-thienyl)-3H-imidazo[4,5-b]pyridin-3-yl (hereafter, it may be simply denoted as "Ds"), $N_{30}$ forms a base pair with $N_5$, $N_{31}$ forms a base pair with $N_4$, $N_{32}$ forms a base pair with $N_3$, $N_{33}$ forms a base pair with $N_2$, and $N_{34}$ forms a base pair with $N_1$. The base pair may be a GC pair. In one embodiment, $N_{30}$ represents A, $N_{32}$ represents C. $N_{33}$ represents G, and/or $N_{34}$ represents T. Examples of the nucleotide sequence (i) (a) include the sequences as shown in any one of SEQ ID NOs: 36, 37, and 40.

The nucleotide sequence (i) (b) is a nucleotide sequence in which one or several nucleotides are added, removed, and/or substituted in the nucleotide sequence (i)(a) at position(s) other than the position of $N_{26}$. The term "one or several" used herein refers to, for example, 1 to 6, 1 to 5, 1 to 4, 1 to 3, or 1 to 2. Addition(s), removal(s), and/or substitution(s) can be performed in a region in which a low degree of conservation was found in a second selection in Example 3, for example, a region of position(s) 1 to 5 or 30 to 34 of SEQ ID NO: 35, preferably, position(s) 1 to 5 or 31.

The nucleotide sequence (ii) (a) is represented by: $N_1 N_2 N_3 N_4 N_5 N_6 GATCACN_{13}N_{14}CTAGGGGN_{22}CCN_{25} N_{26}N_{27}N_{28}N_{29}N_{30}N_{31}$ (SEQ ID NO: 28), wherein $N_1$ to $N_6$, $N_{14}$, and $N_{25}$ each independently represent G, T, A, or C, $N_{13}$ and $N_{22}$ each independently represent Ds, $N_{26}$ forms a base pair with $N_4$, $N_{29}$ forms a base pair with $N_3$, $N_{30}$ forms a base pair with $N_2$, $N_{31}$ forms a base pair with $N_1$, and $N_{27}$ and $N_{28}$ each independently represent G, T, A, or C or none. The base pair may be a GC pair. In one embodiment, $N_3$ represents C, $N_4$ represent G, and/or $N_{14}$ represent A. An example of the nucleotide sequence (ii) (a) is the sequence as shown in SEQ ID NO: 29.

The nucleotide sequence (ii) (b) is a nucleotide sequence in which one or several nucleotides are added, removed, and/or substituted in the nucleotide sequence (ii)(a) at position (s) other than the position(s) of $N_{13}$ and $N_{22}$. Addition(s), deletion(s), and/or substitution(s) can be performed in a region in which a low degree of conservation was found in a second selection in Example 3, for example, a region of position(s) 1 to 6, 14, or 25 to 31, such as position(s) 1 to 6 or 25 to 31 of SEQ ID NO: 28, preferably, position(s) 1 to 2, 5 and 6, or 25 to 31.

In one embodiment, the nucleotide sequence (i) (a) or (ii) (a) comprises, at its terminus, base pairs, for example, 1 to 5, 1 to 4, 1 to 3, 1 to 2, or 1 GC pair(s). In addition to or instead of the base pair(s) mentioned above, the nucleotide sequence (i) (a) or (ii) (a) may comprise a sequence constituting a mini-hairpin structure (hereafter, such sequence may be referred to as the "mini-hairpin sequence").

Examples of sequences in which the mini-hairpin sequence is added to the sequence (i) (a) include the sequences as shown in SEQ ID NO: 41 or SEQ ID NO: 80 in which the mini-hairpin sequence is added to the sequence as shown in SEQ ID NO: 40. An example of a sequence in which the mini-hairpin sequence is added to the sequence (ii) (a) include the sequence as shown in SEQ ID NO: 33 in which the mini-hairpin sequence is added to the sequence as shown in SEQ ID NO: 29.

The DNA aptamer that binds to a cancer cell according to the present invention may consist of the nucleotide sequences (i) (a)-(b) or (ii) (a)-(b) or sequences in which GC pair and/or a mini-hairpin structure is added thereto.

Cancer cells to which the DNA aptamer according to the present invention binds include breast cancer cells, liver cancer cells, pancreatic cancer cells, prostate cancer cells, ovarian cancer cells, colorectal (e.g., colon) cancer cells, gastric cancer cells, cervix cancer cells, and lung cancer cells. Cancer cells used herein include leukemia cells and malignant lymphomas. Cancer cells may be derived from any organism species. Examples thereof include mammals including primates such as humans and chimpanzees, experimental animals such as rats and mice, livestock animals such as pigs, cows, horses, sheep, and goats, and pet animals such as dogs and cats, preferably, humans.

The DNA aptamer that binds to cancer cells according to the present invention binds to a wide variety of cancer cells. Accordingly, such DNA aptamer can be used for detection or treatment of various types of cancer cells or cancers. The DNA aptamer comprising the nucleotide sequence (i) (a) or (i) (b) can not only bind to cancer cells but also suppress cancer cell growth. Thus, the DNA aptamer can be used as an anticancer agent.

The length of the DNA aptamer that binds to a cancer cell according to the present invention is, for example, 150 mer or shorter, 140 mer or shorter, 130 mer or shorter, 120 mer or shorter, or 110 mer or shorter, and it is preferably 100 mer or shorter, 90 mer or shorter, 80 mer or shorter, 70 mer or shorter, or 60 mer or shorter.

The DNA aptamer that binds to cancer cells according to the present invention may optionally comprise a base analog, another artificial base, another modified base, or the like, in addition to Ds.

The DNA aptamer that binds to cancer cells according to the present invention may be modified by the addition of other substances, such as polyethylene glycol (PEG) (e.g., a PEG polymer of about 20 to 60 kDa), an amino acid, a peptide, inverted dT, a lipid, a dye, a fluorescent substance, an enzyme, a radioactive substance, and biotin. Such substance may be linked via a known linker, if needed. Examples of linkers used herein include a nucleotide linker, a peptide linker, and a linker containing a disulfide bond. It is generally known that a half-life of the DNA aptamer is extended by linking PEG to the DNA aptamer.

The DNA aptamer that binds to a cancer cell according to the present invention has a Kd for cancer cells of, for example, 100 nM or lower, 90 nM or lower, 80 nM or lower, 70 nM or lower, 60 nM or lower, 50 nM or lower, 40 nM or lower, 30 nM or lower, 20 nM or lower, and preferably 10 nM or lower, 9 nM or lower, 8 nM or lower, 7 nM or lower, 6 nM or lower, 5 nM or lower, 4 nM or lower, or 3 nM or lower, based on the measurement of flow cytometry.

A method for producing the DNA aptamer that binds to cancer cells according to the present invention is not particularly limited. A method known in the art may be employed. For example, the DNA aptamer according to the present invention can be chemically synthesized on the basis of the sequences indicated above in accordance with a known solid-phase synthesis method. Regarding a method of chemical synthesis of nucleic acids, see, for example, Current Protocols in Nucleic Acid Chemistry. Volume 1, Section 3. Many life science manufacturers (e.g., Takara Bio Inc. and Sigma-Aldrich Corporation) provide contract manufacturing services concerning such chemical synthesis, and such services may be used. A DNA aptamer may be prepared by synthesizing several fragments on the basis of the DNA aptamer sequence and then ligating the fragments via, for example, intramolecular annealing or ligation using a ligase.

The DNA aptamer according to the present invention prepared by chemical synthesis is preferably purified by a method known in the art before use. Examples of methods of purification include gel purification, affinity column purification, and HPLC.

3. DNA Aptamer Binding to Breast Cancer Cells

In one aspect, the present invention relates to a DNA aptamer that binds to breast cancer cells comprising the nucleotide sequences (I) (a)-(b), (II) (a)-(b), (III) (a)-(b), or (IV) (a)-(b) below.

The nucleotide sequence (I) (a) is represented by $N_1N_2N_3N_4N_5N_6CAGCCTGGGN_{16}TN_{18}TCTTTN_{24}$ $AGTCN_2AN_{31}TTCAN_{36}TCGN_{40}N_{41}N_{42}N_{43}N_{44}N_{45}$ (SEQ ID NO: 43), wherein $N_1$ to $N_6$, $N_{15}$, $N_{24}$, $N_{31}$, and $N_{36}$ each independently represent G, T, A, or C, $N_{16}$ represents Ds, $N_{79}$ represents Ds, G, T, A, or C, preferably Ds, $N_{40}$ forms a base pair with $N_6$, $N_{41}$ forms a base pair with $N_5$, $N_{42}$ forms a base pair with $N_4$, $N_{43}$ forms a base pair with $N_3$, $N_{44}$ forms a base pair with $N_2$, and $N_{45}$ forms a base pair with $N_1$. In one embodiment, $N_3$ represents T. $N_{18}$ represents C. $N_{24}$ represents T, $N_{31}$ represents G. and/or $N_{36}$ represents A. Examples of the nucleotide sequence (I) (a) include the nucleotide sequences as shown in SEQ ID NOs: 44 or 46.

The nucleotide sequence (I) (b) is a nucleotide sequence in which one or several nucleotides are added, deleted, and/or substituted in the nucleotide sequence (I)(a) at position (s) other than the position of $N_{16}$, preferably at position (s) other than those of $N_{16}$ and $N_{29}$. Addition(s), deletion(s), and/or substitution(s) can be performed in a region in which a low degree of conservation was found in a second selection in Example 3, such as a region of position(s) 1 to 6, 18, 24, 29, 31, 36, or 40 to 45, for example, a region of position(s) 1 to 6, 18, 24, 31, 36, or 40 to 45, preferably a region of position(s) 1 to 6 or 40 to 45, and more preferably a region of position(s) 1 to 2, 4 to 6, or 40 to 45 of SEQ ID NO: 43.

The nucleotide sequence (II) (a) is represented by $N_1N_2N_3N_4CN_6N_7TCGAACTGN_6N_{17}ATGAGN_{23}GTN_{26}$ $N_{27}N_{28}N_{29}N_{30}N_{31}$ (SEQ ID NO: 2), wherein $N_1$ to $N_4$, $N_7$, $N_{16}$, $N_{23}$, $N_{26}$, and $N_{31}$ each independently represent G, T, A, or C, preferably, Ds, $N_6$ represents Ds, G, T, A, or C, $N_{17}$ represents Ds, $N_{27}$ forms a base pair with $N_3$, $N_{28}$ forms a base pair with $N_2$, and $N_{29}$ and $N_{30}$ each independently represent G, T, A, or C or none. $N_{23}$ may form a base pair with $N_7$ and $N_{31}$ may form a base pair with $N_1$. In one embodiment, $N_7$ represents G, $N_{16}$ represents T, and/or $N_{23}$ represents C. Examples of the nucleotide sequence (II) (a) include the nucleotide sequences as shown in any one of SEQ ID NOs: 3 to 5, 8, 9, and 14 to 16.

The nucleotide sequence (II) (b) includes a nucleotide sequence in which one or several nucleotides are added, deleted, and/or substituted in the nucleotide sequence (II)(a) at position (s) other than the position of $N_{17}$, and preferably at position (s) other than those of $N_6$ and $N_{17}$. Addition(s), deletion(s), and/or substitution(s) can be performed in a region in which a low degree of conservation was found in a second selection in Example 3, such as a region of position(s) 1 to 4, 6 to 7, 16, 23, or 26 to 31, specifically a region of position(s) 1 to 4, 7, 16, 23, or 26 to 31, preferably a region of position(s) 1 to 4, 7, 23, or 26 to 31, and more preferably a region of position(s) 1 to 4 or 26 to 31 of SEQ ID NO: 2.

The nucleotide sequence (III) (a) is represented by $N_1N_2N_3CCGGCTN_{10}N_{11}N_{12}N_{13}N_{14}N_{15}N_{16}N_{17}N_{18}N_{19}$ $N_{20}N_{21}N_{22}N_{23}N_{24}N_{25}TCCTGGN_{32}N_{33}TA$ $AGGTTTCTAAN_{46}N_{47}N_{48}N_{49}N_{50}N_{51}$ (SEQ ID NO: 18), wherein $N_1$ to $N_3$, $N_{13}$ to $N_{17}$, $N_{19}$ to $N_{22}$, $N_{33}$, $N_{46}$ to $N_{48}$, and $N_{50}$ each independently represent G, T, A, or C, $N_{10}$ to $N_{12}$ and $N_{23}$ to $N_{25}$ each independently represent G, T, A, or C or none, $N_{18}$ represents Ds, G, T, A, or C or none, $N_{32}$ represents Ds, $N_{49}$ forms a base pair with $N_3$. $N_{51}$ forms a base pair with $N_1$, and 3 or more of $N_{10}$ to $N_{15}$ form base pairs with 3 or more of $N_{20}$ to $N_{25}$. $N_{50}$ may form a base pair with $N_2$, and $N_{10}$ to $N_{15}$ may form complete base pairs with $N_{20}$ to $N_{25}$. $N_{10}$ to $N_{25}$ may form a mini-hairpin structure as a whole. In one embodiment, $N_{33}$ represents C, $N_{46}$ represents A, $N_{47}$ represents G, and/or $N_{48}$ represents G.

Examples of the nucleotide sequence (III) (a) include the sequences as shown in any one of SEQ ID NOs: 20, 21, and 26.

The nucleotide sequence (III) (b) is a nucleotide sequence in which one or several nucleotides are added, deleted, and/or substituted in the nucleotide sequence (II)(a) at position (s) other than the position of $N_{32}$. Addition(s), deletion(s), and/or substitution(s) can be performed in a region in which a low degree of conservation was found in a second selection in Example 3, such as a region of position(s) 1 to 3, 10 to 25, 33, or 46 to 51, for example, a region of position(s) 1 to 3, 10 to 25, or 46 to 51, and preferably a region of position(s) 1 to 3 or 46 to 51 of SEQ ID NO: 18.

The nucleotide sequence (IV) (a) is represented by $N_1N_2N_3$TCTTAAGTTTA$N_{15}$A$N_{17}N_{18}$T$N_{20}N_{21}N_{22}N_{23}$ $T_{25}N_{26}N_{27}N_{28}N_{29}N_{30}N_{31}N_{32}$T$N_{34}$GGG CGTTTTAAN$N_4N_{48}N_{49}$ (SEQ ID NO: 50), wherein $N_1$ to $N_3$, $N_{15}$, $N_{17}$, $N_{20}$ to $N_{23}$, $N_{25}$ to $N_{29}$, $N_{31}$ to $N_{32}$, N+a, and $N_{46}$ each independently represent G, T, A, or C, $N_{18}$ and $N_{30}$ each independently represent Ds, $N_{47}$ forms a base pair with $N_3$, $N_{48}$ forms a base pair with $N_2$, and $N_{49}$ forms a base pair with $N_1$. In one embodiment, $N_1$ represents C, $N_2$ represents C, $N_{15}$ represents T, and/or $N_{34}$ represents A. An example of the nucleotide sequence (IV) (a) includes the sequence as shown in SEQ ID NO: 51.

The nucleotide sequence (IV) (b) is a nucleotide sequence in which one or several nucleotides are added, removed, and/or substituted in the nucleotide sequence (IV)(a) at position (s) other than those of $N_{18}$ and $N_{30}$. Addition(s), removal(s), and/or substitution(s) can be performed in a region in which a low degree of conservation was found in a second selection in Example 3, such as a region of position(s) 1 to 3, 15, 17, 20 to 23, 25 to 29, 31 to 32, 34, or 46 to 49, for example, a region of position(s) 1 to 3 or 47 to 49, and preferably a region of position 3 or position(s) 47 to 49 of SEQ ID NO: 50.

In one embodiment, the nucleotide sequence (I) (a), (II) (a), (III) (a), or (VI) (a) comprises, at its terminus, base pairs, such as 1 to 5, 1 to 4, 1 to 3, 1 to 2, or 1 GC base-pair(s).

In addition to or instead of the base pairs mentioned above, the nucleotide sequence (1) (a), (II) (a), (III) (a), or (VI) (a) may comprise sequences constituting a mini-hairpin structure. An example of a sequence in which the mini-hairpin sequence is added to the sequence (I)(a) includes the sequence as shown in SEQ ID NO: 45 in which the mini-hairpin sequence is added to the sequence as shown in SEQ ID NO: 44. Examples of sequences in which the mini-hairpin sequence is added to the sequence (II)(a) include the sequences as shown in SEQ ID NO: 10 and SEQ ID NOs: 11 to 13 in which the mini-hairpin sequence is added to the sequence as shown in SEQ ID NOs: 9 and 14 to 16, respectively. Examples of sequences in which the mini-hairpin sequence is added to the sequence (III)(a) include the sequences as shown in SEQ ID NOs: 24 and 25 in which the mini-hairpin sequence is added to the sequence as shown in SEQ ID NOs: 9 and 20 and 26, respectively. An example of a sequence in which the mini-hairpin sequence is added to the sequence (IV)(a) includes the sequence as shown in SEQ ID NO: 52 in which the mini-hairpin sequence is added to the sequence as shown in SEQ ID NO: 51.

The DNA aptamer that binds to breast cancer cells according to the present invention may optionally comprise a base analog, another artificial base, another modified base, or the like, in addition to Ds.

The DNA aptamer that binds to breast cancer cells according to the present invention may comprise the nucleotide sequences (I) (a)-(b), (II) (a)-(b), (III) (a)-(b), or (IV) (a)-(b) or sequences in which GC pair(s) and/or a mini-hairpin sequence is added thereto.

The DNA aptamer that binds to breast cancer cells according to the present invention may bind to another types of cancer cells other than breast cancer cells. Examples of such cancer cells include, but are not limited to, prostate cancer cells and lung cancer cells. Cancer cells may be derived from any organism species. Examples thereof include mammals, for example, primates such as humans and chimpanzees, experimental animals such as rats and mice, livestock animals such as pigs, cows, horses, sheep, and goats, and pet animals such as dogs and cats, and preferably, human cancer cells.

The DNA aptamer that binds to breast cancer cells according to the present invention, in particular, the DNA aptamers (I) to (III) are derived from the 07-MB231 aptamer, the 14A-MCF7 aptamer, and the 08B-MCF7 aptamer, respectively. These DNA aptamers were shown to exhibit different binding ability depending on breast cancer cell lines. Accordingly, such aptamers enables classification of breast cancer cells. For example, the 07-MB231 aptamer bound to the MDA-MB-231 cell only, which is the triple-negative breast cancer cell line. Therefore, a DNA aptamer comprising the nucleotide sequence (I) (a) or (I) (b) derived from the 07-MB231 aptamer is particularly useful, since it enables determination as to whether or not the breast cancer cell of interest is the triple-negative breast cancer cell and can be used for diagnosis of the triple-negative breast cancer. The triple-negative breast cancer refers to the type of breast cancer in which none of breast cancer causal genes; i.e., estrogen receptor (ER), progesterone receptor (PR), and human epidermal growth factor receptor 2 (HER2) genes, are overexpressed. Thus, no treatment guideline has been established for the triple-negative breast cancer, prognosis thereof was poor, and detection thereof was difficult.

The DNA aptamer that binds to breast cancer cells according to the present invention may be modified by adding other substances, such as polyethylene glycol (PEG) (e.g., a PEG polymer of about 20 to 60 kDa), an amino acid, a peptide, inverted dT, a lipid, a dye, a fluorescent substance, an enzyme, a radioactive substance, and biotin. Such substance may be linked via a known linker, if needed. It is generally known that a half-life of the DNA aptamer is extended by linking PEG to the DNA aptamer.

The length of the DNA aptamer that binds to breast cancer cells according to the present invention is, for example, 150 mer or shorter, 140 mer or shorter, 130 mer or shorter, 120 mer or shorter, 110 mer or shorter, and preferably 100 mer or shorter, 90 mer or shorter, 80 mer or shorter, 70 mer or shorter, or 60 mer or shorter.

A method of producing the DNA aptamer that binds to a breast cancer cell according to the present invention is the same as described in the "2. DNA aptamer binding to cancer cells" above, and explanation thereof is accordingly omitted herein.

4. Pharmaceutical Composition Comprising DNA Aptamer

In one aspect, the present invention relates to a pharmaceutical composition comprising the DNA aptamer described in the 2 or 3 above (the DNA aptamer(s) described in the 2 and 3 above are collectively referred to as "the DNA aptamer(s) according to the present invention"). The pharmaceutical composition according to the present invention can comprise one or more other drugs, provided that the ability of the aptamer according to the present invention to bind to cancer cells is not lost. For example, the pharmaceutical composition may comprise a given amount of an anticancer agent.

In one embodiment, the present invention relates to a pharmaceutical composition comprising the DNA aptamer and another drug for delivering the drug to a cancer cell. The other drugs may be bound to the DNA aptamer, so that the drug can be efficiently delivered to the cancer cell, utilizing the ability of the DNA aptamer to bind to the cancer cells. A method for binding the DNA aptamer to the drug is not particularly limited.

Target diseases to be prevented and/or treated with the pharmaceutical composition according to the present invention are cancers, such as breast cancer, liver cancer, pancreatic cancer, prostate cancer, ovarian cancer, colorectal cancer, colon cancer, gastric cancer, cervix cancer, and lung cancer, as well as leukemia, and malignant lymphoma.

Therapeutic effects are expected by administrating the pharmaceutical composition to a subject afflicted with cancer, and preventive effects are expected by administrating the pharmaceutical composition to a subject at risk of cancer.

The pharmaceutical composition according to the present invention can comprise a pharmaceutically acceptable carrier. The term "pharmaceutically acceptable carrier" refers to a substance generally used in the art that facilitates preparation of a pharmaceutical composition or application thereof to an organism, and such substance is added to the pharmaceutical composition in an amount that does not inhibit or suppress the activity of the pharmaceutical composition. Examples of carriers include an excipient, a binder, a disintegrator, a filler, an emulsifier, a fluidity adjustor, a lubricant, and a stabilizer.

Examples of "excipient" include a sugar, such as monosaccharide, disaccharide, cyclodextrin, and a polysaccharide (specific examples include, but are not limited to, glucose, sucrose, lactose, raffinose, mannitol, sorbitol, inositol, dextrin, maltodextrin, starch, and cellulose), metal salt (e.g., sodium phosphate, calcium phosphate, calcium sulfate, and magnesium sulfate), citric acid, tartaric acid, glycine, low-, middle-, and high-molecular-weight polyethylene glycol (PEG), Pluronic, and a combination thereof.

Examples of "binder" include starch glue using corn, wheat, rice, or potato starch, gelatin, gum tragacanth, methylcellulose, hydroxypropyl methylcellulose, carboxymethyl cellulose sodium, and polyvinyl pyrrolidone.

Examples of "disintegrator" include the starch, carboxymethylstarch, crosslinked polyvinyl pyrrolidone, agar, alginic acid, sodium alginate, and a salt thereof.

Examples of "filler" include the sugar and calcium phosphate (e.g., tricalcium phosphate and calcium hydrogen phosphate).

Examples of "emulsifier" include sorbitan fatty acid ester, glycerin fatty acid ester, sucrose fatty acid ester, and propylene glycol fatty acid ester.

Examples of "fluidity adjuster" and "lubricant" include silicate, talc, stearate, and polyethylene glycol.

Examples of "stabilizer" include an anti-oxidant such as ascorbic acid or sulfite, and sugar such as trehalose or glucose.

Such carrier may adequately be used, if needed. In addition to the additives described above, the pharmaceutical composition according to the present invention can comprise a corrigent, a solubilizer (a solubilizing agent), a suspension, a diluent, a surfactant, an absorbefacient (e.g., a quaternary ammonium salt and sodium lauryl sulfate), an extender, a wetting agent, a moisturizing agent (e.g., glycerin and starch), an absorbent (e.g., starch, lactose, kaolin, bentonite, and colloidal silicic acid), a disintegrator (e.g., saccharose, stearin, cacao butter, and hydrogenated oil), a coating agent, a colorant, a preservative, a flavoring agent, an aromatic agent, a sweetening agent, a buffer, an isotonizing agent, a soothing agent, solubilizer, or the like.

Examples of "surfactant" include alkali metal salt, alkaline earth metal salt, and ammonium salt of lignosulfonic acid, naphthalenesulfonic acid, phenolsulfonic acid, and dibutylnaphthalenesulfonic acid, alkyl aryl sulfonate, alkyl sulfate, alkyl sulfonate, fatty alcohol sulfate, fatty acid, sulfated fatty alcohol glycol ether, a condensate of a naphthalene sulfonate or naphthalene derivative and formaldehyde, a condensate of naphthalene, naphthalane sulfonic acid, or phenol and formaldehyde, polyoxyethylene octyl phenyl ether, ethoxylated isooctyl phenol, octyl phenol, nonyl phenol, alkylphenyl polyglycol ether, tributylphenyl polyglycol ether, tristearyl phenyl polyglycol ether, alkyl aryl polyether alcohol, a condensate of an alcohol/fatty alcohol and ethylene oxide, ethoxylated castor oil, polyoxyethylene alkyl ether, ethoxylated polyoxypropylene, lauryl alcohol polyglycol ether acetal, sorbitol ester, lignosulfite waste liquor, and methylcellulose.

A pharmaceutical composition according to this embodiment can contain one or more of the carriers mentioned above.

A dosage form of the pharmaceutical composition according to the present invention is not particularly limited, provided that an active ingredient is not inactivated and pharmacological effects can be exerted in vivo after administration. In general, a dosage form varies depending on a route of administration and/or prescription conditions.

Examples of dosage forms suitable for oral administration include solid preparations (including tablets, pills, sublingual formulations, capsules, drops, and troches), granules, powders, and liquids. If needed, solid preparations can be preparations with coating materials known in the art, such as sugar-coated tablets, gelatin-coated tablets, enteric coated tablets, film-coated tablets, double-layer tablets, or multi-layer tablets.

Parenteral administration is classified as systemic administration or topical administration, and topical administration is further classified as interstitial administration, transepidermal administration, transmucosal administration, or transrectal administration. The pharmaceutical composition can be prepared in a dosage form suitable for the route of administration. Examples of dosage forms suitable for systemic or interstitial administration include injection preparations, which are liquids. Examples of dosage forms suitable for transepidermal or transmucosal administration include liquids (including embrocations, eye drops, nasal drops, and inhalants), suspensions (including emulsifiers and cream agents), powders (including nasal drops and inhalants, pastes, gels, ointments, and plasters). An example of a dosage form suitable for transrectal administration is a suppository.

Specific configurations and sizes of the dosage forms mentioned above are not particularly limited, provided that they are within the scope of the dosage forms known in the art.

In principle, the pharmaceutical composition according to the present invention may be prepared in accordance with a method known in the art. For example, see the method described in Remington's Pharmaceutical Sciences (Merck Publishing Co., Easton. Pa.).

For example, injection preparations can be prepared by a method generally used in the art, comprising dissolving the DNA aptamer according to the present invention in a pharmaceutically acceptable solvent and adding a pharmaceutically acceptable carrier thereto, if needed.

Examples of "pharmaceutically acceptable solvent" include water, ethanol, propylene glycol, ethoxylated isostearyl alcohol, polyoxylated isostearyl alcohol, and a polyoxyethylene sorbitan fatty acid ester. Such solvent is preferably made isotonic to the blood, if needed.

The pharmaceutical composition according to the present invention can be administered to an organism in a pharmaceutically effective amount for treatment or prevention of a target disease such as cancer. A target organism is a vertebrate, preferably a mammal, and more preferably a human.

The pharmaceutical composition according to the present invention may be administered systemically or topically. An adequate administration route can be selected depending on a disease type, a site of disease onset, a stage, or the like. In the case of a disease that develops in a topical site, for example, topical administration directly to the site of disease onset and a region in the vicinity thereof by means of injection is preferable. This is because a sufficient amount of the DNA aptamer according to the present invention can be administered to a site to be treated (i.e., the tissue or organ) and other tissue is less likely to be affected. When the site to be treated cannot be identified or a disease develops throughout the body, systemic administration via intravenous injection or the like is preferable, although the administration route is not limited. By spreading the DNA aptamer according to the present invention through the blood flow throughout the body, it can be administered to a lesion that cannot be identified by diagnosis.

The pharmaceutical composition according to the present invention can be administered by any adequate method, provided that active ingredients are not inactivated. For example, a parenteral route (e.g., by means of injection, aerosol, topical application, instillation, or nasal drip) or an oral route may be employed, preferably, by injection.

In the case of injection administration, the site of injection is not particularly limited, provided that the DNA aptamer as an active ingredient is capable of binding to a target substance. For example, intravenous, intraarterial, intrahepatic, intramuscular, intraarticular, intramedullary, intraspinal, intraventricular, transpulmonary, percutaneous, subcutaneous, intracutaneous, or intraperitoneal administration may be performed.

5. Anticancer Agent Consisting of DNA Aptamer

In one aspect, the present invention relates to an anticancer agent consisting of the DNA aptamer comprising the nucleotide sequence (i) (a) or (i) (b) described in the "2. DNA aptamer binding to cancer cells" above. The 05-MB231 aptamer from which the DNA aptamer has been derived is not only capable of binding to cancer cells but is also capable of suppressing cancer cell growth. Thus, such aptamer can be used as an anticancer agent. In one embodiment, the present invention relates to a pharmaceutical composition comprising, as an active ingredient, an anticancer agent consisting of the DNA aptamer described above. Since the constitution of the pharmaceutical composition is as described above, the explanation thereof is omitted herein.

6. Method of Treatment Using DNA Aptamer

In one aspect, the present invention relates to a method of cancer treatment and/or prevention comprising administering the pharmaceutical composition or anticancer agent to a subject.

Target diseases to be prevented and/or treated with the pharmaceutical composition according to the present invention are cancers, such as breast cancer, liver cancer, pancreatic cancer, prostate cancer, ovarian cancer, colorectal cancer, colon cancer, gastric cancer, cervix cancer, and lung cancer, as well as leukemia, and malignant lymphoma.

Examples of animal species encompassed by "subjects" herein include mammals, for example, primates such as humans and chimpanzees, experimental animals such as rats and mice, livestock animals such as pigs, cows, horses, sheep, and goats, and pet animals such as dogs and cats, preferably, humans.

7. Detection Agent Comprising DNA Aptamer

In one aspect, the present invention relates to an agent for detecting a cancer comprising the DNA aptamer according to the present invention. The agent for detecting a cancer according to the present invention is a composition for detection of cancer or cancer cells in vivo or in vitro utilizing the ability of the DNA aptamer to bind to cancer cells. For example, the DNA aptamer is labeled with a fluorescence reagent beforehand, and the labeled DNA aptamer is administered to an organism, so as to determine the presence or absence of cancer cells in vivo, and investigate the localization thereof when the cancer cells are present. The DNA aptamer according to the present invention is useful for imaging and tissue staining.

In one aspect, the present invention relates to a composition for detecting a cancer comprising the DNA aptamer according to the present invention. The composition is the same as described with regard to the pharmaceutical composition above and explanation thereof is accordingly omitted herein.

In one aspect, the present invention relates to a kit for detecting a cancer cell comprising the DNA aptamer according to the present invention. In addition to the DNA aptamer according to the present invention, the kit according to the present invention may comprise, for example, a buffer, a label reagent, and/or instructions.

The agent for detecting a cancer, the composition for detecting a cancer, and the kit for detecting a cancer according to the present invention can be used for a method that assists diagnosis as to cancer affliction or a method of cancer cell classification described below.

8. Method of Cancer Cell Detection

In one aspect, the present invention relates to a method for detecting a cancer cell. This method comprises a step of contacting a sample obtained from a subject with the DNA aptamer according to the present invention and a step of detecting cancer cells based on the binding between the sample and the DNA aptamer. This method can assist diagnosis as to whether or not a subject is afflicted with cancer.

Samples used in the method of the present invention include biological samples including tissue and cells. Tissue examples include sites of lesions, such as breast, liver, pancreas, prostate gland, ovary, colorectal, colon, stomach, uterine cervix, lung, bone marrow, lymph node, spleen, and thymic gland. For example, biopsy samples of such tissues can be used. Examples of cells include the peripheral blood cells, the cell-containing lymphs and interstitial fluids, hair matrix cells, oral cavity cells, nasal cavity cells, intestinal tract cells, intravaginal cells, mucosal cells, and sputum (that can contain alveolar cells or tracheal cells).

When the DNA aptamer according to the present invention recognize markers such as proteins, lipids, and sugar chains existing on cancer cells and such markers are for example, secreted or cleaved to appear in body fluids, such as urine and blood, the DNA aptamer according to the present invention can be used to detect such markers in the body fluid.

A step of detection in the method of detection according to the present invention is not particularly limited, provided that the binding between the sample and the DNA aptamer is utilized, and any known method may be employed. For example, SPR method, turbidimetric method, colorimetric method, or fluorescence method may be employed.

Surface plasmon resonance (SPR) is a phenomenon that the intensity of a reflected light decreases sharply at a particular angle of incidence (i.e., an angle of resonance) when a laser beam is irradiated to a metal thin film. SPR is a measurement method based on the phenomenon described above and is capable of assaying a substance adsorbed on the surface of the metal thin film, which is a sensor, with high sensitivity. According to the present invention, for example, the target substance in the sample can then be detected by immobilizing the DNA aptamer according to the present invention on the surface of the metal thin film beforehand, allowing the sample to pass through the surface of the metal thin film, and detecting the difference of the amount of the substance adsorbed on the surface of the metal thin film resulting from the binding of the nucleic acid and target substance, between before and after the sample passes therethrough. Examples of known SPR techniques include the displacement method and the indirect competitive method, and any method may be employed herein.

Turbidimetry is a method comprising irradiating a light to a solution, optically assaying an attenuation in the light scattered by substances suspended in the solution or a light transmitted through the solution using a colorimeter or the like, and assaying the amount of the substance of interest in the solution. According to the present invention, the target substance in the sample can be quantitatively detected by assaying the absorbance before and after the DNA aptamer according to the present invention is added to the sample.

Also, the target substance can be detected by using an antibody reacting with the target substance in combination. For example, sandwich ELISA may be employed. According to this technique, the DNA aptamer according to the present invention is first immobilized on a solid-phase support, the sample is added, and the target substance in the sample is then allowed to bind to the DNA aptamer. Subsequently, the sample is washed away, and the anti-target substance antibody is added and allowed to bind to the target substance. After washing, an adequately labeled secondary antibody is used to detect the anti-target substance antibody, and the target substance in the sample can be thus detected. Examples of solid-phase supports that can be used include insoluble supports in the form of beads, microplates, test tubes, sticks, test pieces, and the like, made of materials such as polystyrene, polycarbonate, polyvinyl toluene, polypropylene, polyethylene, polyvinyl chloride, nylon, polymethacryate, latex, gelatin, agarose, cellulose, sepharose, glass, metal, ceramic, or magnet.

In one aspect, present invention relates to a method for assisting diagnosis as to whether or not a subject is afflicted with cancer. This method comprises: a step of administering the DNA aptamer according to the present invention or the agent for detecting a cancer or composition for detecting a cancer according to the present invention to a subject; and a step of detecting the DNA aptamer. When the DNA aptamer is detected at high density at a particular site in an organism, for example, it can be determined that cancer has developed at the site of interest. The step of detection may be carried out in accordance with a conventional technique. For example, the fluorescence method mentioned above may be employed.

9. Method of Cancer Cell Classification

In one aspect, the present invention relates to a method of classifying cancer cells obtained from a subject. This method comprises: a step of contacting cancer cells obtained from a subject with the DNA aptamer according to the present invention; a step of determining the presence or absence of the binding between the cancer cells and the DNA aptamer, or measuring the strength of the binding; and a step of classifying cancer cells based on the presence or absence of the binding, or the strength of the binding. The step of determining the presence or absence of the binding between the cancer cells and the DNA aptamer or measuring the strength of the binding is carried out in the same manner as described in the method of cancer cell detection above, and explanation thereof is thus omitted herein.

This method may be carried out using only one of the DNA aptamers according to the present invention or a plurality of the DNA aptamers according to the present invention. When only one of the DNA aptamers according to the present invention is used, cancer cells can be more precisely classified by using the method in combination with a conventional method of cancer classification selected from among, for example, configuration observation, cancer marker assay, staining, and the use of a conventional aptamer.

According to the method of cancer cell classification of the present invention, the origin tissue, the subtype, the intrinsic subtype, the degree of differentiation, infiltration, and the like of the cancer cell can be classified on the basis of the binding between the cancer cell and the DNA aptamer. On the basis of the cancer cell classification, for example, the clinical stage (i.e., the progression and the stage) can be determined, the prognosis can be predicted, and the treatment regimen can be prepared for the subject from which the cancer cells are derived.

In one embodiment, the cancer cells classified in accordance with the method according the present invention are breast cancer cells. This method preferably involves the use of two or more DNA aptamers selected from among the 4 groups (I) to (IV) described in the "3. DNA aptamer binding to breast cancer cells." such as two or more DNA aptamers selected from among the three groups (I) to (III) for the following reasons. That is, the DNA aptamers selected from among the three groups (I) to (III) are derived from the 07-MB231 aptamer, the 14A-MCF7 aptamer, and the 08B-MCF7 aptamer, respectively, and these DNA aptamers are shown to exhibit different binding ability depending on breast cancer cell lines. For example, the 07-MB231 aptamer can bind to the MDA-MB-231 cell only, which is the triple-negative breast cancer cell line. Therefore, a DNA aptamer comprising the nucleotide sequence (I) (a) or (b) derived from the 07-MB231 aptamer is particularly useful, since it enables determination as to whether or not the breast cancer cell of interest is the triple-negative breast cancer cell and can be used for diagnosis of the triple-negative breast cancer. The triple-negative breast cancer refers to the type of breast cancer in which none of breast cancer causal genes; i.e., estrogen receptor (ER), progesterone receptor (PR), and human epidermal growth factor receptor 2 (HER2) genes, are overexpressed. Thus, no treatment guideline has been established for the triple-negative breast cancer, prognosis thereof was poor, and detection thereof was difficult.

EXAMPLES

Example 1: Cell-SELEX

Cell Lines:

Where the cell lines used in the examples were derived and culture media therefor are as described below:

human breast cancer-derived cell lines MCF7 (RIKEN BioResource Center (BRC), RCB1904, MEM), T-47D (ATCC, HTB-133™, RPMI 1640 medium), MDA-MB-231 (ATCC, HTB-26™, L15 medium, in the absence of $CO_2$, DMEM medium in the presence of $CO_2$), and MDA-MB-453 (BRC, RCB1192, L15 medium, in the absence of $CO_2$, DMEM medium in the presence of $CO_2$); human fibrous disease of the breast-derived cell line MCF10A (ATCC, CRL-10317™, MEGM medium); colorectal cancer-derived cell line HCT-116 (BRC, RCB2979, DMEM medium): lung cancer-derived cell line A549 (BRC, RCB0098, F12K medium); gastric cancer-derived cell line MKN45 (BRC, RCB1001, RPMI 1640 medium); ovarian cancer-derived cell line NIH: OVCAR-3 (BRC, RCB2135, RPMI 1640 medium); prostate cancer-derived cell line PC-3 (ATCC, CRL-1435, RPMI 1640 medium): pancreatic cancer-derived cell lines MIAPaca2 (Institute of Development, Aging and Cancer, Tohoku University, TKG0227, RPMI 1640 medium) and Panc1 (Institute of Development, Aging and Cancer, Tohoku University, TKG0606, RPMI 1640 medium): liver cancer-derived cell line PLC/PRT/5 (JCRB, JCRB0406, RPMI 1640 medium); cervix cancer-derived cell line HeLa (BRC, BRC0007, MEM medium); myelocytic leukemia-derived cell line KG-1 (BRC, RCB1166, RPMI 1640 medium); acute lymphatic leukemia-derived cell line CCRF-CEM (Institute of Development, Aging and Cancer, Tohoku University, 1-4924, RPMI 1640 medium); and human umbilical vein endothelial cells (Huvec) (Lonza, CC-2519, MEG medium). The above cell lines were used in all the examples unless otherwise specified.

(Cell-SELEX)

At first, a DNA library was prepared in accordance with the method described in WO 2013/073602. The DNA library is composed of nucleic acids including a 95-bp sequence comprising primer sequences (25 nucleotides each) at both termini and a 45-bp random sequence in the middle. In the 45-bp random sequence, an artificial base Ds has been incorporated into two sites, and the sites of incorporation can be determined based on a sequence of 3 nucleotides at the 5'-terminus of the random sequence (i.e., a tag sequence). Twenty four types of sublibraries containing such tag sequences were chemically synthesized and mixed to prepare a DNA library (N42Ds3nmix-P003) (Table 1).

TABLE 1

Table 1: List of libraries and primer sequences used for test

| Name | Sequence | SEQ ID NO: |
|---|---|---|
| N42Ds-01 | 5'-GAGNNNNNNNNNNNNNNNNNNNNNNNDsNNNNNNNDsNNNNNNNNNNNNNNN-3' | 53 |
| N42Ds-02 | 5'-GACNNNNNNNNNNNNNNNNNNNNNNNDsNNNNNNNDsNNNNNNNNNNNNNNN-3' | 54 |
| N42Ds-03 | 5'-CAGNNNNNNNNNNNNNNNNNNNNNNNDsNNNNNNNDsNNNNNNNNNNNNNNN-3' | 55 |
| N42Ds-04 | 5'-CACNNNNNNNNNNNNNNNNNNNNNNNDsNNNNNNNDsNNNNNNNNNNNNNNN-3' | 56 |
| N42Ds-05 | 5'-AGGNNNNNNNNNNNNNNNNNNNNNNDsNNNNNNNDsNNNNNNNNNNNNNNN-3' | 57 |
| N42Ds-06 | 5'-GGANNNNNNNNNNNNNNNNNNNNNNDsNNNNNNNDsNNNNNNNNNNNNNNN-3' | 58 |
| N42Ds-07 | 5'-GGGNNNNNNNNNNNNNNNNNNNNNDsNNNNNNNNDsNNNNNNNNNNNNNNN-3' | 59 |
| N42Ds-08 | 5'-GGCNNNNNNNNNNNNNNNNNNNNNDsNNNNNNNNDsNNNNNNNNNNNNNNNN-3' | 60 |
| N42Ds-09 | 5'-GGTNNNNNNNNNNNNNNNDsNNNNNNNNNNNNDsNNNNNNNNNNNNNNN-3' | 61 |
| N42Ds-10 | 5'-CGANNNNNNNNNNNNNNDsNNNNNDsNNNNNNNNNNNNNNNNNNNNNN-3' | 62 |
| N42Ds-11 | 5'-CGGNNNNNNNNNNNNNNDsNNNNNNNNDsNNNNNNNNNNNNNNNNNNNN-3' | 63 |
| N42Ds-12 | 5'-CGCNNNNNNNNNNNNNNDsNNNNNNNNNDsNNNNNNNNNNNNNNNNNNN-3' | 64 |
| N42Ds-13 | 5'-CGTNNNNNNNNNNNNNNDsNNNNNNNNNNDsNNNNNNNNNNNNNNNNNN-3' | 65 |
| N42Ds-14 | 5'-TGGNNNNNNNNNNNNNDsNNNNNNNNNNNDsNNNNNNNNNNNNNNNNNN-3' | 66 |
| N42Ds-15 | 5'-TGCNNNNNNNNNNNNNDsNNNNNNNNNNNNDsNNNNNNNNNNNNNNNNN-3' | 67 |
| N42Ds-16 | 5'-ACGNNNNNNNNNNNNNDsNNNNNNNNNNNNDsNNNNNNNNNNNNNNNNN-3' | 68 |
| N42Ds-17 | 5'-GCANNNNNNNNNNNNNDsNNNNNNNNNNNNNDsNNNNNNNNNNNNNNNN-3' | 69 |
| N42Ds-18 | 5'-GCGNNNNNNNNNNNNNNNNNDsNNNNNDsNNNNNNNNNNNNNNNN-3' | 70 |
| N42Ds-19 | 5'-GCCNNNNNNNNNNNNNNNNDsNNNNNNNNNDsNNNNNNNNNNNNNNN-3' | 71 |
| N42Ds-20 | 5'-GCTNNNNNNNNNNNNNNNNDsNNNNNNNNNNDsNNNNNNNNNNNNNNN-3' | 72 |
| N42Ds-21 | 5'-CCANNNNNNNNNNNNNNNNDsNNNNNNNNNNNDsNNNNNNNNNNNNNNN-3' | 73 |
| N42Ds-22 | 5'-CCGNNNNNNNNNNNNNNNNDsNNNNNNNNNNNNDsNNNNNNNNNNNNNN-3' | 74 |
| N42Ds-23 | 5'-CCCNNNNNNNNNNNNNNDsNNNNNNNNNNNNDsNNNNNNNNNNNNNNN-3' | 75 |
| N42Ds-24 | 5'-CCTNNNNNNNNNNNNNNNDsNNNNNNNNNNNNNDsNNNNNNNNNNNNNNN-3' | 76 |
| 5'-Rev019 | 5'-ACGACCGTTCTCTAATTTTGACGTT-3' | 77 |

TABLE 1-continued

Table 1: List of libraries and primer sequences used for test

| Name | Sequence | SEQ ID NO: |
|---|---|---|
| 3'T15-L-Fow026 | 5'-TTTTTTTTTTTTTTT-C12spacer-ACCAAATTATTGCGATACAGACCCT-3' | 78 |
| 3'-Fow026 | 5'-ACCAAATTATTGCGATACAGACCCT-3' | 79 |

Cell-SELEX that detects the breast cancer cell line MCF7 was initiated with 2,000 pmol of the library. Also, the breast cancer cell line T-47D and the breast cancer cell line MDA-MB-231 were utilized for Cell-SELEX using 1,000 pmol of the library as a starting material. Cell-SELEX was performed in accordance with the method described in Non Patent Literature 1, and the DNA library containing artificial bases was handled in accordance with the method described in WO 2013/073602.

From the third round, counter selection was performed in accordance with the method described in Non Patent Literature 1 using, as a control cell, the non-cancer mammary gland-derived endothelial cell line MCF10A. Screening conditions for the cells are shown in Tables 2 to 4.

TABLE 2

Conditions for MCF7 Cell-SELEX selection

| Library | Round | [DNA] (nM) | Volume (ml) | Cell | Binding | Time (min) | Washing | PCR cycles |
|---|---|---|---|---|---|---|---|---|
| N42Ds3mix-P003 | 1 | 1000 | 2 | MCF7 (100 mm dish x1) | 4° C. | 60 | 5 ml x 5 times | 15 |
| | pre-2 | 50 | 2 | MCF10A (100 mm dish x1) | 4° C. | 60 | | |
| | 2 | 50 | 2 | MCF7 (100 mm dish x1) | 4° C. | 30 | 5 ml x 5 min x 5 times | 22 |
| | pre-3 | 5 | 2 | MCF10A (100 mm dish x5) | 4° C. | 60 | | |
| | 3 | 5 | 10 | MCF7 (100 mm dish x1) | 4° C. | 30 | 5 ml x 10 min x 5 times | 20 |
| | pre-4 | 2.5 | 2 | MCF10A (100 mm dish x5) | Room temperature | 60 | | |
| | 4 | 2.5 | 10 | MCF7 (100 mm dish x1) | 4° C. | 30 | 7 ml x 10 min x 5 times | 21 |
| | pre-5 | 1 | 2 | MCF10A (100 mm dish x5) | Room temperature | 60 | | |
| | 5 | 1 | 10 | MCF7 (100 mm dish x1) | 4° C. | 30 | 10 ml x 10 min x 5 times | 20 |
| | pre-6 | 1 | 2 | MCF10A (100 mm dish x5) | Room temperature | 60 | | |
| | 6 | 1 | 10 | MCF7 (100 mm dish x1) | 4° C. | 30 | 10 ml x 10 min x 5 times | 18 |
| | post-6 | | 1 | MCF10A (100 mm dish x1) | Room temperature | 60 | | |
| | pre-7 | 1 | 2 | MCF10A (100 mm dish x5) | 37° C. | 60 | | |
| | 7 | 1 | 10 | MCF7 (100 mm dish x1) | 4° C. | 30 | 10 ml x 10 min x 5 times | 18 |
| | post-7 | | 1 | MCF10A (100 mm dish x1) | 37° C. | 60 | | |

TABLE 3

Conditions for T-47D Cell-SELEX selection

| Library | Round | [DNA] (nM) | Volume (ml) | Cell | Binding | Time (min) | Washing | PCR cycles |
|---|---|---|---|---|---|---|---|---|
| N42Ds3mix-P003 | 1 | 50 | 20 | T-47D (100 mm dish x1) | 4° C. | 60 | 5 ml x 5 times | 23 |
| | 2 | 10 | 10 | T-47D (100 mm dish x1) | 4° C. | 60 | 5 ml x 5 min x 5 times | 24 |
| | pre-3 | 5 | 10 | MCF10A (150 mm dish x1) | 4° C. | 60 | | |
| | 3 | 5 | 10 | T-47D (100 mm dish x1) | 4° C. | 30 | 5 ml x 10 min x 5 times | 25 |
| | pre-4 | 2.5 | 10 | MCF10A (150 mm dish x1) | 4° C. | 60 | | |
| | 4 | 2.5 | 10 | T47D (100 mm dish x1) | 4° C. | 30 | 7 ml x 10 min x 5 times | 26 |
| | pre-5 | 2.5 | 10 | MCF10A (150 mm dish x1) | 4° C. | 60 | | |
| | 5 | 2.5 | 10 | T-47D (100 mm dish x1) | 4° C. | 30 | 10 ml x 10 min x 5 times | 25 |
| | pre-6 | 1 | 10 | MCF10A (150 mm dish x1) | 4° C. | 60 | | |
| | 6 | 1 | 10 | T-47D (100 mm dish x1) | 4° C. | 30 | 10 ml x 10 min x 5 times | 24 |
| | pre-7 | 1 | 5 | MCF10A (150 mm dish x1) | 4° C. | 60 | | |
| | 7 | 1 | 5 | T-47D (100 mm dish x1) | 4° C. | 30 | 10 ml x 10 min x 5 times | 22 |

TABLE 4

Conditions for MDA-MB-231 Cell-SELEX selection

| Library | Round | [DNA] (nM) | Volume (ml) | Cell | Binding | Time (min) | Washing | PCR cycles |
|---|---|---|---|---|---|---|---|---|
| N42Ds3mix-P003 | 1 | 50 | 20 | MDA-MB-231 (100 mm dish x1) | 4° C. | 60 | 5 ml x 5 times | 14 |
| | 2 | 10 | 10 | MDA-MB-231 (100 mm dish x1) | 4° C. | 60 | 5 ml x 5 min x 5 times | 15 |
| | pre-3 | 5 | 10 | MCF10A (150 mm dish x1) | 4° C. | 60 | | |
| | 3 | 5 | 10 | MDA-MB-231 (100 mm dish x1) | 4° C. | 45 | 5 ml x 10 min x 5 times | 21 |
| | pre-4 | 2.5 | 10 | MCF10A (150 mm dish x1) | 4° C. | 60 | | |
| | 4 | 2.5 | 10 | MDA-MB-231 (100 mm dish x1) | 4° C. | 30 | 7 ml x 10 min x 5 times | 23 |

TABLE 4-continued

Conditions for MDA-MB-231 Cell-SELEX selection

| Library | Round | [DNA] (nM) | Volume (ml) | Cell | Binding | Time (min) | Washing | PCR cycles |
|---|---|---|---|---|---|---|---|---|
| | pre-5 | 2.5 | 10 | MCF10A (150 mm dish x1) | 4° C. | 60 | | |
| | 5 | 2.5 | 10 | MDA-MB-231 (100 mm dish x1) | 4° C. | 30 | 10 ml × 10 min × 5 times | 21 |
| | pre-6 | 1 | 10 | MCF10A (150 mm dish x1) | 4° C. | 60 | | |
| | 6 | 1 | 10 | MDA-MB-231 (100 mm dish x1) | 4° C. | 30 | 10 ml × 10 min × 5 times | 24 |
| | pre-7 | 1 | 5 | MCF10A (150 mm dish x1) | 4° C. | 60 | | |
| | 7 | 1 | 5 | MDA-MB-231 (100 mm dish x1) | 4° C. | 30 | 10 ml × 10 min × 5 times | 19 |

The DNA pool obtained after each round of selection was subjected to PCR and labeled with fluorescence (Alexa488) at the 5'-terminus. The enrichment of the bound sequences was then examined using a flow cytometer. Specifically, 25 pmol each of the Alexa488-labeled DNA pool obtained after each round was heated in D-PBS(−) at 95° C. for 5 minutes, and the resultant was allowed to stand at room temperature for 20 minutes for folding. These labeled DNAs were subjected to incubation with an enzyme-free suspension of MCF7 ($2.5 \times 10^5$ cells) at 4° C. for 30 minutes (0.45% glucose, 0.1 mg/ml tRNA, 1 mg/ml BSA, 5 mM $MgCl_2$/D-PBS(−)). After the labeled DNAs that did not bind to cells were washed away with the use of a wash buffer (0.45% glucose, 5 mM $MgCl_2$), the DNA aptamers bound to the cells were analyzed using a flow cytometer (S3 Cell Sorter, BIO-Rad) in terms of changes in the fluorescence intensity.

As a result, the fluorescence intensity began to change from the fifth round of MCF7 Cell-SELEX, and the fluorescence intensity continued to increase up to the seventh round. In the case of MDA-MB231, the fluorescence intensity began to change from the sixth round, and the fluorescence intensity further increased at the seventh round. A population exhibiting changes in the fluorescence intensity at the seventh round (i.e., a population exhibiting fluorescence-labeled DNAs bound to cells) was fractionated using a cell sorter (S3 Cell Sorter, BIO-Rad).

Example 2: Sequence Determination of DNA Obtained Via Cell-SELEX

The nucleotide sequences of DNAs obtained from the sorted cells were identified via Ion-PGM sequencing (Thermo Fisher Scientific). The number of the target sequences to be analyzed in MCF7 Cell-SELEX was 80,592, when extracting sequences retaining primer sequences correctly at the both termini from among a total read number of 246,903 different sequence molecules. When the extent of sequence enrichment was examined based on enrichment of each molecule and then derivatives having one nucleotide difference are clustered, ten molecules were identified as enriched candidate sequences. These candidate moleculess were chemically synthesized and subjected to screening based on the binding ability. As a result, two sequences (14A-MCF7 (SEQ ID NO: 4) and 08B-MCF7 (SEQ ID NO: 17)) were identified.

The number of the target sequences to be analyzed in T-47D Cell-SELEX (the first round) was 205,801, when extracting sequences retaining primer sequences correctly at the both termini from among a total read number of 638,160 sequences. On the basis of the extracted sequences, the sequences shifted therefrom by 1 nucleotide were clustered as derived sequences. As a result, the sequences were found to be enriched to a sequence constituting 76% of the whole (03-T47D: SEQ ID NO: 27)).

The number of the target sequences to be analyzed in MDA-MB-231 Cell-SELEX was 128,607, when extracting sequences retaining primer sequences correctly at the both termini from among a total read number of 497,341 sequences. On the basis of the extracted sequences, the sequences shifted therefrom by 1 nucleotide were clustered as derived sequences and the extent of sequence condensation was examined. As a result, the following three molecules: i.e., 23-MB231 (SEQ ID NO: 49): 36.6%; 05-MB231 (SEQ ID NO: 34): 17.5%; and 07-MB231 (SEQ ID NO: 42): 14.2%, were highly enriched.

Example 3: Second Selection of DNA Aptamer Obtained Via Cell-SELEX

The DNA aptamers comprising the sequences obtained in Example 2 were subjected to second selection (doped selection) in accordance with the method described in Example 3 of WO 2013/073602, and the secondary structure of each DNA aptamer was elaborated. Second selection was carried out with the use of a library prepared to comprise 55% of the nucleotide composition of the original sequence obtained by the first step selection and 15% each of other nucleotides (Doped-14A, Doped-08B, Doped-03-T47D short, Doped-05-MB231, Doped-07-MB231, and Doped-23-MB231).

Selection was carried for four rounds using the target cells; i.e., MCF7, T-47D, or MDA-MB-231. The second selection conditions for each DNA aptamer are shown in Tables 5 to 7.

TABLE 5

Second selection conditions for aptamers obtained via MCF7 Cell-SELEX

| Library | Round | [DNA] (nM) | Volume (ml) | Cell | Binding | Time (min) | Washing | PCR cycles |
|---|---|---|---|---|---|---|---|---|
| Doped-14A | 1 | 50 | 10 | MCF7 (100 mm dish x1) | 4° C. | 60 | 5 ml × 3 times | 22 |
| | 2 | 5 | 10 | MCF7 (100 mm dish x1) | 4° C. | 45 | 5 ml × 5 min × 3 times | 25 |
| | 3 | 2 | 5 | MCF7 (100 mm dish x1) | 4° C. | 30 | 5 ml × 5 min × 3 times | 28 |
| | 4 | 1 | 5 | MCF7 (100 mm dish x1) | 4° C. | 30 | 5 ml × 5 min × 5 times | 21 |

TABLE 5-continued

Second selection conditions for aptamers obtained via MCF7 Cell-SELEX

| Library | Round | [DNA] (nM) | Volume (ml) | Cell | Binding | Time (min) | Washing | PCR cycles |
|---|---|---|---|---|---|---|---|---|
| Doped-08B | 1 | 50 | 10 | MCF7 (100 mm dish x1) | 4° C. | 60 | 5 ml × 3 times | 21 |
| | 2 | 5 | 10 | MCF7 (100 mm dish x1) | 4° C. | 45 | 5 ml × 5 min × 3 times | 25 |
| | 3 | 2 | 5 | MCF7 (100 mm dish x1) | 4° C. | 30 | 5 ml × 5 min × 3 times | 25 |
| | 4 | 1 | 5 | MCF7 (100 mm dish x1) | 4° C. | 30 | 5 ml × 5 min × 5 times | 16 |

TABLE 6

Second selection conditions for aptamers obtained via T-47D Cell-SELEX

| Library | Round | [DNA] (nM) | Volume (ml) | Cell | Binding | Time (min) | Washing | PCR cycles |
|---|---|---|---|---|---|---|---|---|
| Doped-03-T47D short | 1 | 50 | 10 | T-47D (100 mm dish x1) | 4° C. | 60 | 5 ml × 3 times | 19 |
| | 2 | 5 | 10 | T-47D (100 mm dish x1) | 4° C. | 45 | 5 ml × 5 min × 3 times | 21 |
| | 3 | 2 | 5 | T-47D (100 mm dish x1) | 4° C. | 30 | 5 ml × 5 min × 3 times | 20 |
| | 4 | 1 | 5 | T-47D (100 mm dish x1) | 4° C. | 30 | 5 ml × 5 min × 5 times | 19 |

TABLE 7

Second selection conditions for aptamers obtained via MDA-MB-231 Cell-SELEX

| Library | Round | [DNA] (nM) | Volume (ml) | Cell | Binding | Time (min) | Washing | PCR cycles |
|---|---|---|---|---|---|---|---|---|
| Doped-05-MB231 | 1 | 50 | 10 | MDA-MB231 (100 mm dish x1) | 4° C. | 60 | 5 ml × 3 times | 18 |
| | 2 | 5 | 10 | MDA-MB231 (100 mm dish x1) | 4° C. | 45 | 5 ml × 5 min × 3 times | 21 |
| | 3 | 2 | 5 | MDA-MB231 (100 mm dish x1) | 4° C. | 30 | 5 ml × 5 min × 3 times | 24 |
| | 4 | 1 | 5 | MDA-MB231 (100 mm dish x1) | 4° C. | 30 | 5 ml × 5 min × 5 times | 21 |
| Doped-07-MB231 | 1 | 50 | 10 | MDA-MB-231 (100 mm dish x1) | 4° C. | 60 | 5 ml × 3 times | 15 |
| | 2 | 5 | 10 | MDA-MB231 (100 mm dish x1) | 4° C. | 45 | 5 ml × 5 min × 3 times | 24 |
| | 3 | 2 | 5 | MDA-MB231 (100 mm dish x1) | 4° C. | 30 | 5 ml × 5 min × 3 times | 24 |
| | 4 | 1 | 5 | MDA-MB231 (100 mm dish x1) | 4° C. | 30 | 5 ml × 5 min × 5 times | 21 |
| Doped-23-MB231 | 1 | 50 | 10 | MDA-MB-231 (100 mm dish x1) | 4° C. | 60 | 5 ml × 3 times | 15 |
| | 2 | 5 | 10 | MDA-MB231 (100 mm dish x1) | 4° C. | 45 | 5 ml × 5 min × 3 times | 21 |
| | 3 | 2 | 5 | MDA-MB231 (100 mm dish x1) | 4° C. | 30 | 5 ml × 5 min × 3 times | 25 |
| | 4 | 1 | 5 | MDA-MB231 (100 mm dish x1) | 4° C. | 30 | 5 ml × 5 min × 5 times | 23 |

FIGS. 1 to 6 show the sequences of the DNA aptamers obtained via Cell-SELEX. A nucleotide found to have conserved more than 85% between first selection and second selection is circled.

Example 4: Modification of 14A-MCF7 Aptamer

Figure 7:
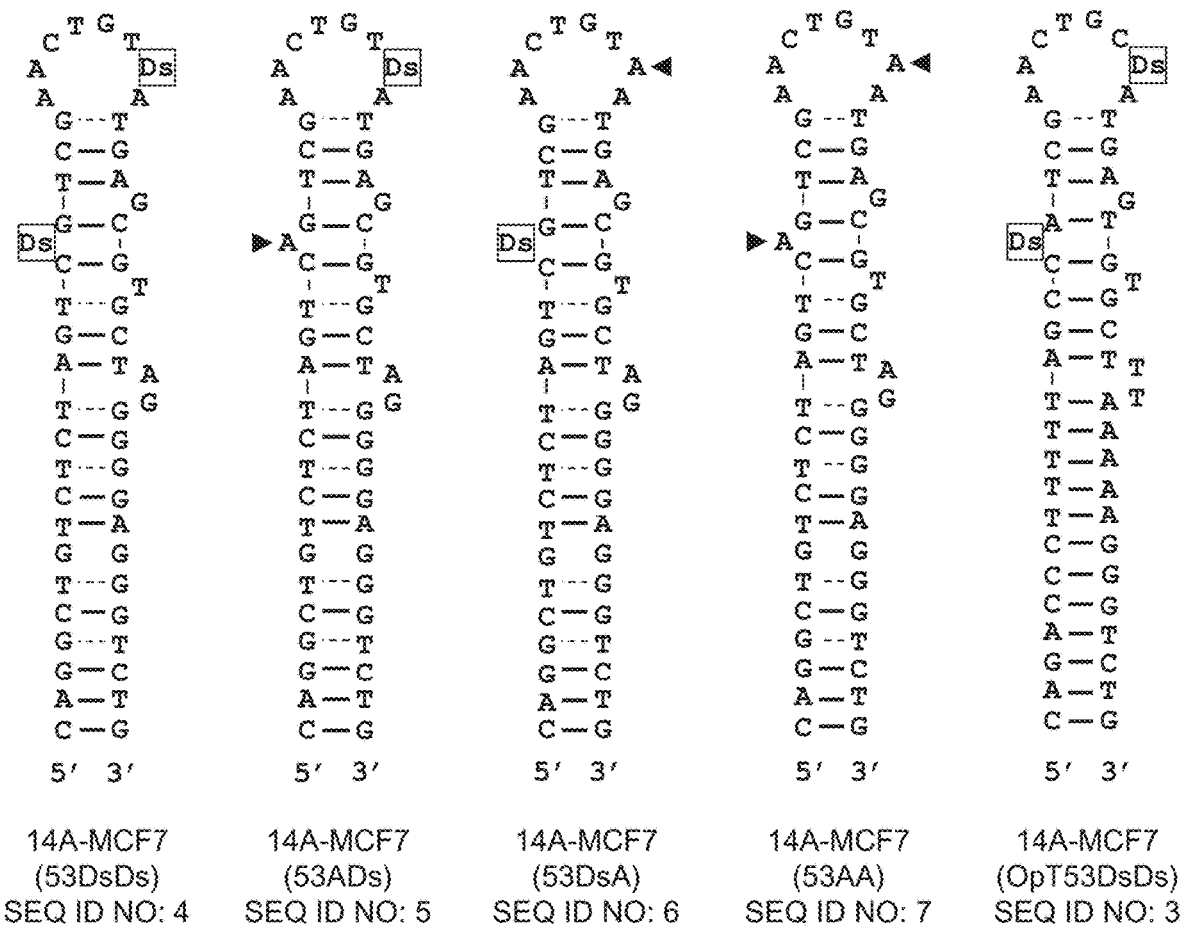
FIG. 7 shows the sequences of the DNA aptamers used in Example 4 and the putative secondary structures. On the basis of 14A-MCF7 (53DsDs) (SEQ ID NO: 4), Ds at position 17 was substituted with A to design 14A-MCF7 (53ADs) (SEQ ID NO: 5), Ds at position 28 was substituted with A to design 14A-MCF7 (53DsA) (SEQ ID NO: 6), Ds at positions 17 and 28 were each substituted with A to design 14A-MCF7 (53AA) (SEQ ID NO: 7), and AG at the 3'-terminal bulge portion were substituted with TT and a part of the mismatched region of the stem region was substituted to form a base pair to design 14A-MCF7 (Opt53DsDs) (SEQ ID NO: 3). Ds is boxed and a position at which Ds was substituted with A is shown by an arrow head.

On the basis of 14A-MCF7 (53DsDs) (SEQ ID NO: 4) obtained in Example 3, Ds at position 17 was substituted with A to design 14A-MCF7 (53ADs) (SEQ ID NO: 5), Ds at position 28 was substituted with A to design 14A-MCF7 (53DsA) (SEQ ID NO: 6), Ds at positions 17 and 28 were each substituted with A to design 14A-MCF7 (53AA) (SEQ ID NO: 7), and AG in the 3'-terminal bulge portion was substituted with TT and a part of the mismatched region in the stem region was substituted to form a base pair to design 14A-MCF7 (Opt53DsDs) (SEQ ID NO: 3). Thus, the DNA aptamers comprising the relevant nucleotide sequences were chemically synthesized. (FIG. 7 shows the nucleotide sequences and the secondary structures thereof elaborated by doped selection.)

Figure 8:
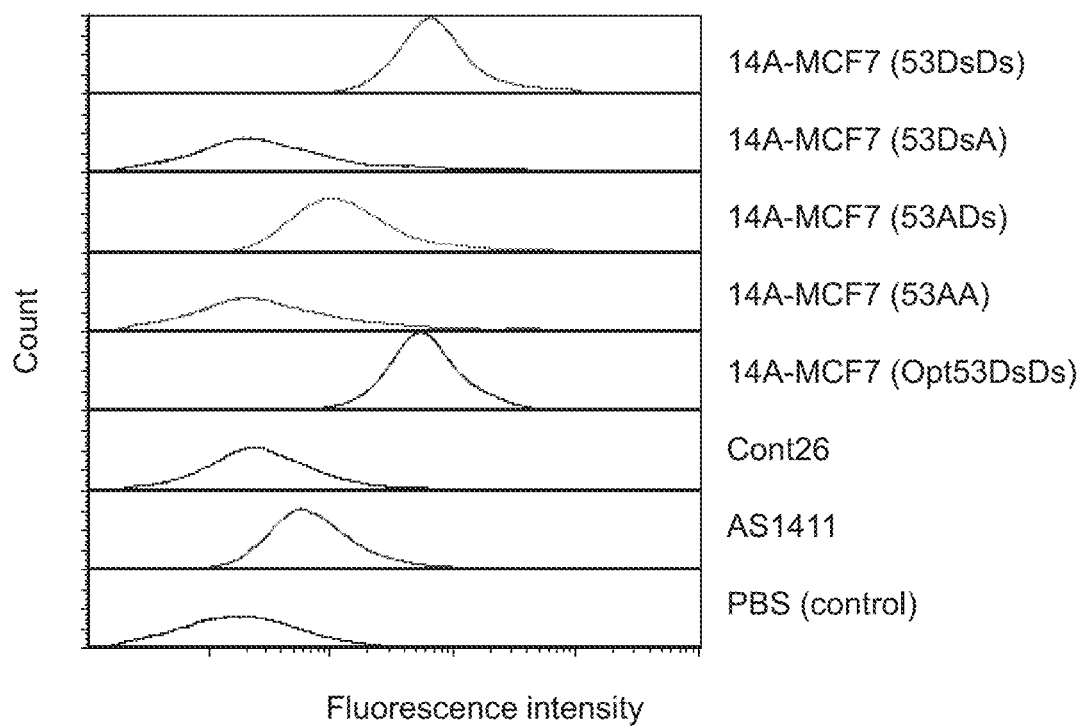
FIG. 8 shows the results of flow cytometry analysis of the DNA aptamers shown in FIG. 7, as well as AS1411, and Cont26 representing the cell-binding ability of each aptamer.

As a positive control, AS1411 targeting nucleolin that is reported to have the ability to bind to a cancer cell (SEQ ID NO: 81) (merely referred to as "AS1411" herein) was chemically synthesized, and as a negative control, Cont26, which is an AS1411 mutant lacking the ability to bind to nucleolin (SEQ ID NO: 82) (merely referred to as "Cont26" herein), was chemically synthesized. With the use of the DNA aptamers prepared in the manner described above, the binding ability to MCF7 cells was analyzed by the changes of the fluorescence intensity as with the case of Example 1 (incubation was carried out in 25 pmol of Alexa488-labeled DNA/2.5×10$^5$ cells/100 μl). As a result, activity of 14A-MCF7 (53ADs) was found to be lowered compared with that of the original DNA aptamer (14A-MCF7 (53DsDs)), and 14A-MCF7 (53DsA) was found to lose its activity. This indicates that Ds in the sequence both at the two positions was each contributed to binding, in particular Ds at the 3'-terminal side was significantly contributed to binding (FIG. 8). The fact that the DNA aptamer 14A-MCF7 (Opt53DsDs) comprising a sequence with modification in the bulge region or the stem region has activity equivalent to that of the original DNA aptamer indicates that such regions are not substantially contributed to binding activity of the DNA aptamer.

Subsequently, the stem length that may affect the binding was examined. On the basis of 14A-MCF7 (53DsDs), specifically, 8 nucleotides were each removed from the 5'-terminus and the 3'-terminus; i.e., 16 nucleotides were removed therefrom in total, to design 14A-MCF7 (37DsDs) (SEQ ID NO: 8), a bulge structure of AG was further removed from 14A-MCF7 (37DsDs) and several terminal stems were substituted with GC pairs to design 14A-MCF7 (35DsDs) (SEQ ID NO: 9), a mini-hairpin structure was added to the 3'-terminus of 14A-MCF7 (35DsDs) to design 14A-MCF7mh (44DsDs) (SEQ ID NO: 10), and 1, 2, and 3 GC pairs were removed from the stem structure to design 14A-MCF7mh (SEQ ID NO: 11), 14A-MCF7mh (40DsDs) (SEQ ID NO: 12), and 14A-MCF7mh (38DsDs) (SEQ ID NO: 13), respectively. Thus, the DNA aptamers comprising the relevant nucleotide sequences were chemically synthesized. (FIG. 9 shows the nucleotide sequences and the secondary structures thereof deduced via doped selection.) The DNA aptamers were subjected to incubation at 250 nM each (25 pmol of Alexa488-labeled DNA/$2.5 \times 10^5$ cells, 100 μl) at 4° C. for 30 minutes, and the cell-binding ability was examined based on changes in the fluorescence intensity using a flow cytometer as with Example 1.

Figure 10:
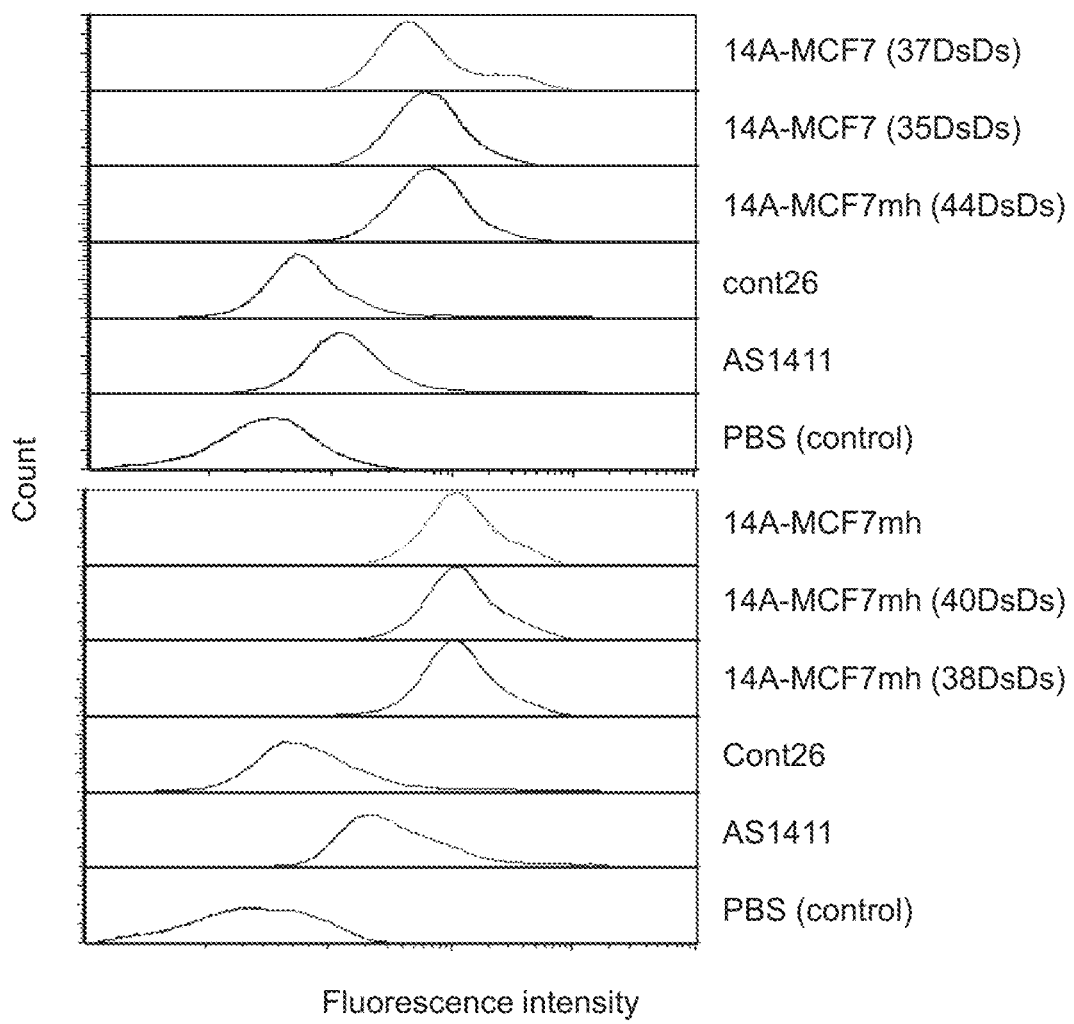
FIG. 10 shows the results of flow cytometric analysis of the cell-binding ability of the DNA aptamers shown in FIG. 9, as well as AS1411, and Cont26.

As a result, all the aptamers were demonstrated to bind to MCF7 cells (FIG. 10). The results demonstrate that equivalent activity is maintained even if the terminal stem structure was shortened or the mini-hairpin structure was added to the terminus.

Example 5: Modification of 08B-MCF7 DNA Aptamer

The 08B-MCF7 aptamer was also modified. On the basis of 08B-MCF7 (51DsDs) (SEQ ID NO: 20), specifically, Ds at position 18 was substituted with A to design 08B-MCF7 (51ADs) (SEQ ID NO: 21), Ds at position 32 was substituted with A to design 08B-MCF7 (51DsA) (SEQ ID NO: 22), Ds at positions 18 and 32 were each substituted with A to design 08B-MCF7 (51AA) (SEQ ID NO: 23), a mini-hairpin structure was added to 08B-MCF7 (51DsDs) to design 08B-MCF7mh (SEQ ID NO: 24), and the internal stem-loop structure of 08B-MCF7mh was substituted with the mini-hairpin structure to design 08B-MCF7mh2 (SEQ ID NO: 25). Thus, the DNA aptamers comprising the relevant nucleotide sequences were chemically synthesized. (FIG. 11 shows the nucleotide sequences and the secondary structures thereof deduced via doped selection.)

The DNA aptamers were subjected to incubation at 250 nM each (25 pmol of Alexa488-labeled DNA/$2.5 \times 10^5$ cells/100 μl) at 4° C. for 30 minutes, and the cell-binding ability was examined based on changes in the fluorescence intensity using a flow cytometer as with Example 1.

Figure 12:
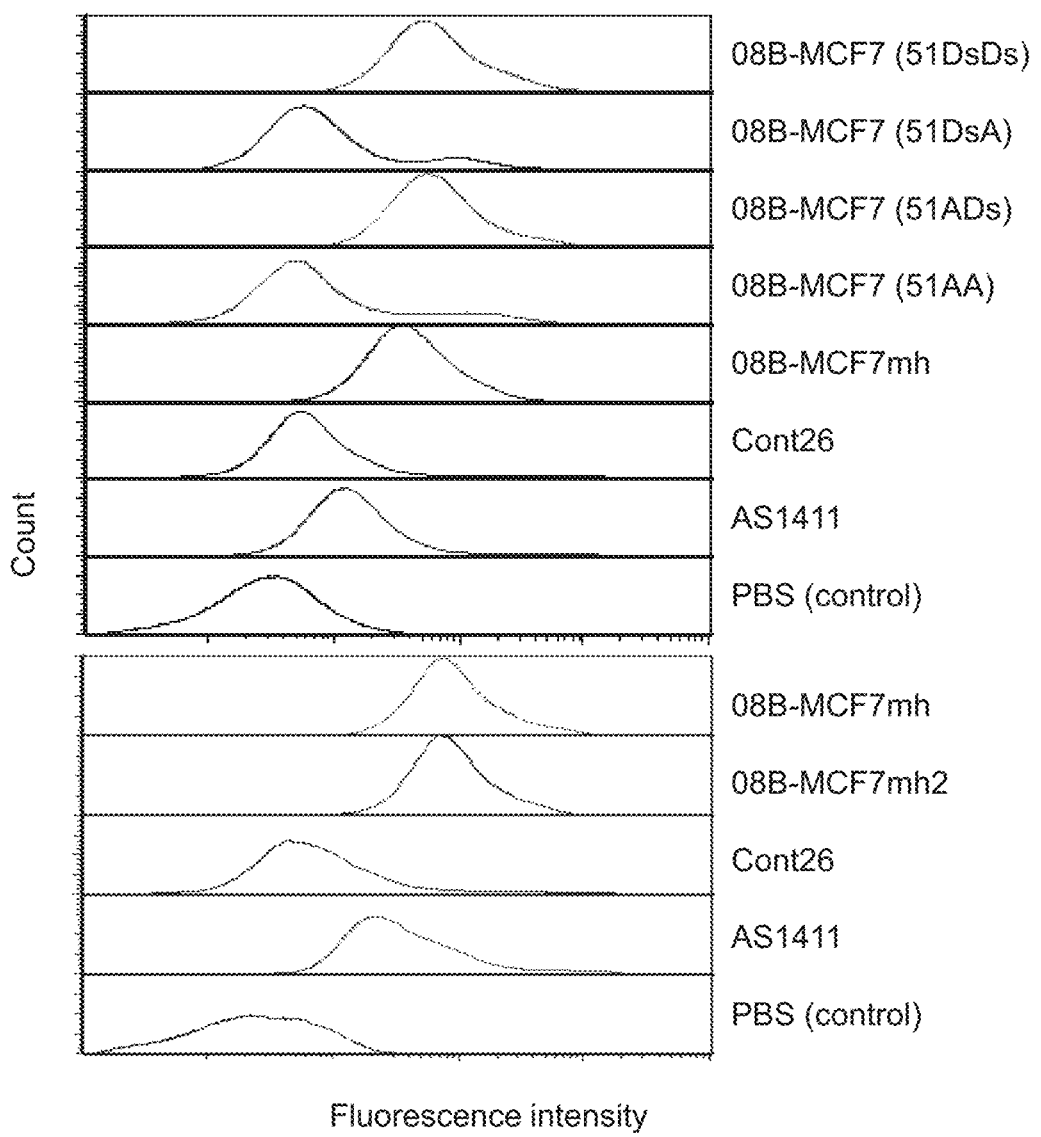
FIG. 12 shows the results of flow cytometric analysis of the cell-binding ability of the DNA aptamers shown in FIG. 11, as well as AS1411, and Cont26.

The results are shown in FIG. 12. While activity of 08B-MCF7 (51ADs) was maintained, activity of 08B-MCF7 (51DsA) was lowered. This indicates that 5'-terminal Ds (position 18) is not contributed to cell binding and only 3'-terminal Ds (position 32) is responsible for the cell-binding ability. Since 5'-terminal Ds is not contributed to cell binding, the 5'-terminal stem-loop structure was substituted with the mini-hairpin structure to synthesize 08B-MCF7mh2, and the resultant was tested. As a result, 08B-MCF7mh2 was found to bind to MCF7 cells (FIG. 12).

Example 6: Modification of 03-T47D Aptamer

The 03-T47D aptamer was also modified. Specifically, On the basis of 03-T47D (DsDs) (SEQ ID NO: 29) in which GC pairs were added to 03-T47D (SEQ ID NO: 27) at its terminus, Ds at position 24 was substituted with A to design 03-T47D (DsA) (SEQ ID NO: 30), Ds at position 15 was substituted with A to design 03-T47D (ADs) (SEQ ID NO: 31), Ds at positions 15 and 24 were each substituted with A to design 03-T47D (AA) (SEQ ID NO: 32), and a mini-hairpin structure was added to the terminus of 03-T47D (DsDs) to design 03-T47Dmh (SEQ ID NO: 33). Thus, the DNA aptamers comprising the relevant nucleotide sequences were chemically synthesized. (FIG. 13 shows the nucleotide sequences and the secondary structures thereof deduced by doped selection.)

The DNA aptamers were incubated with cells at 250 nM each (25 pmol of Alexa488-labeled DNA/$2.5 \times 10^5$ cells/100 μl) at 4° C. for 30 minutes, and the cell-binding ability was examined based on changes in the fluorescence intensity using a flow cytometer as with Example 1.

Figure 14:
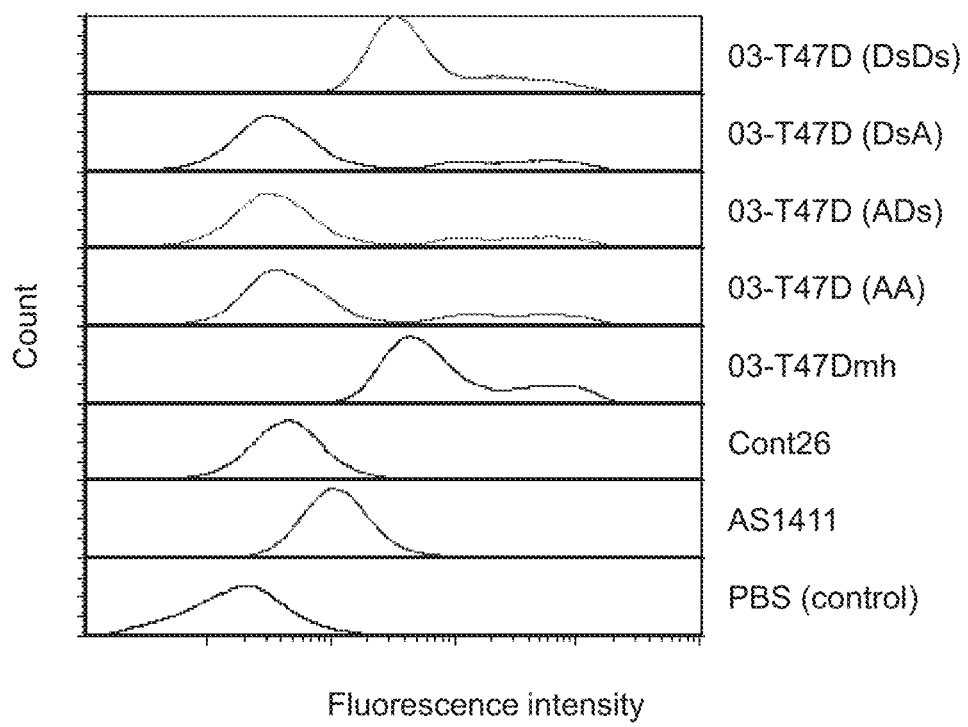
FIG. 14 shows the results of flow cytometric analysis of the cell-binding ability of the DNA aptamers shown in FIG. 13, as well as AS1411, and Cont26.

The results are shown in FIG. 14. A lowered binding activity observed in both 03-T47D (DsA) and 03-T47D (ADs) indicates that 2 Ds bases in the sequence are contributed to cell binding. The cell binding activity of the DNA aptamer (03-T47Dmh), in which a mini-hairpin structure was added to the terminus, was also examined (FIG. 14).

Example 7: Modification of 05-MB231 Aptamer

The 05-MB231 aptamer was also modified. Specifically, On the basis of 05-MB231 (DsDs) (SEQ ID NO: 36) in which a part of the terminal stem portion of 05-MB231 (SEQ ID NO: 34) was substituted with GC pairs, Ds at position 44 was substituted with A to design 05-MB231 (DsA) (SEQ ID NO: 37), Ds at position 33 was substituted with A to design 05-MB231 (ADs) (SEQ ID NO: 38). Ds at positions 33 and 44 were each substituted with A to design 05-MB231 (AA) (SEQ ID NO: 39), a part of the terminal sequence of 05-MB231 (DsDs) was removed and a part of the stem was substituted with GC pairs to design 05-MB231GC (SEQ ID NO: 40), and a mini-hairpin structure was added to 05-MB231GC to design 05-MB231GCmh (SEQ ID NO: 41). Thus, the DNA aptamers comprising the relevant nucleotide sequences were chemically synthesized. (FIG. 15 shows the nucleotide sequences and the secondary structures thereof deduced by doped selection.)

The DNA aptamers were incubated with cells at 250 nM each (25 pmol of Alexa488-labeled DNA/$2.5 \times 10^5$ cells/100 μl) at 4° C. for 30 minutes, and the cell-binding ability was examined based on changes in the fluorescence intensity using a flow cytometer as with Example 1.

Figure 16:
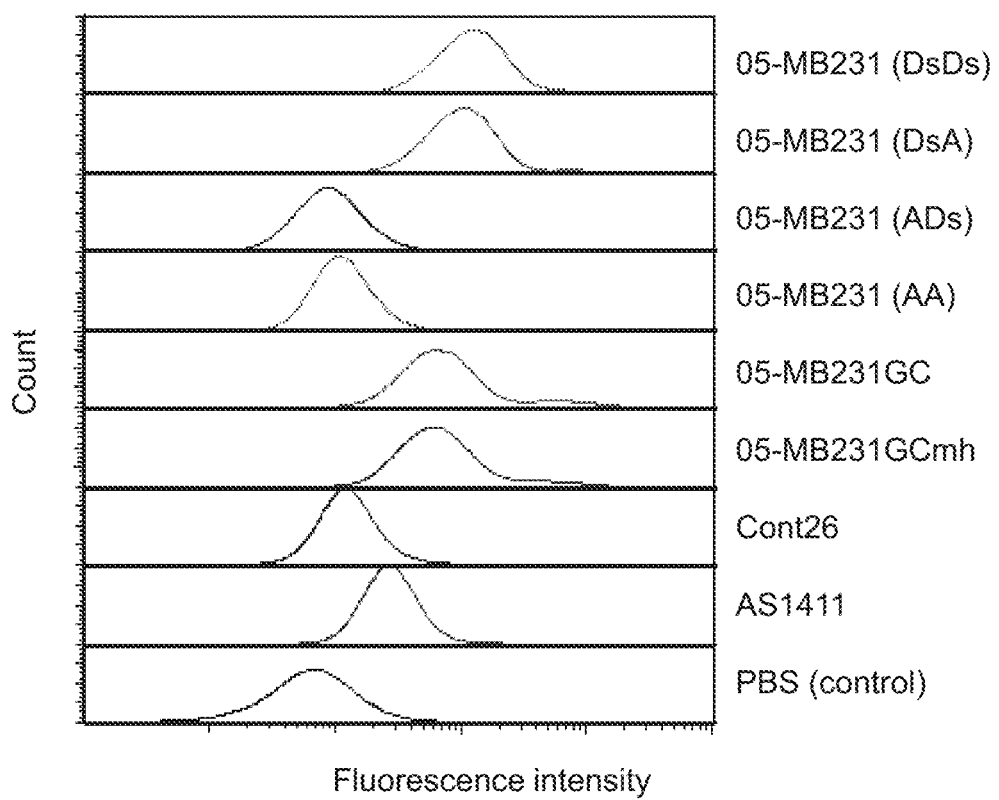
FIG. 16 shows the results of flow cytometric analysis of the cell-binding ability of the DNA aptamers shown in FIG. 15, as well as AS1411, and Cont26.

The results are shown in FIG. 16. While activity of 05-MB231 (ADs) was lowered, activity of 05-MB231 (DsA) was not lowered. This indicates that 3'-terminal Ds is not contributed to cell binding. The binding ability of the DNA aptamer in which such region was removed (05-MB231 GC), and the DNA aptamer in which a mini-hairpin structure was added to its terminus (05-MB231GCmh) was also confirmed.

Example 8: Modification of 07-MB231 Aptamer

The 07-MB231 aptamer was also modified. Specifically, on the basis of 07-MB231 (DsDs) (SEQ ID NO: 44) in which a part of the terminal stem portion of 07-MB231 (SEQ ID NO: 42) was substituted with GC pairs, Ds at position 28 was substituted with A to design 07-MB231 (DsA) (SEQ ID NO: 46), Ds at position 15 was substituted with A to design 07-MB231 (ADs) (SEQ ID NO: 47), Ds at positions 15 and 28 were each substituted with A to design 07-MB231 (AA) (SEQ ID NO: 48), and a mini-hairpin structure was added to the terminus of 07-MB231 to design 07-MB231mh (SEQ ID NO: 45). Thus, the DNA aptamers comprising the relevant nucleotide sequences were chemically synthesized. (FIG. 17 shows the nucleotide sequences and the secondary structures thereof deduced by doped selection.)

The DNA aptamers were incubated with cells at 250 nM each (25 pmol of Alexa488-labeled DNA/2.5×10⁵ cells/100 µl) at 4° C. for 30 minutes, and the cell-binding ability was examined based on changes in the fluorescence intensity using a flow cytometer as with Example 1.

Figure 18:
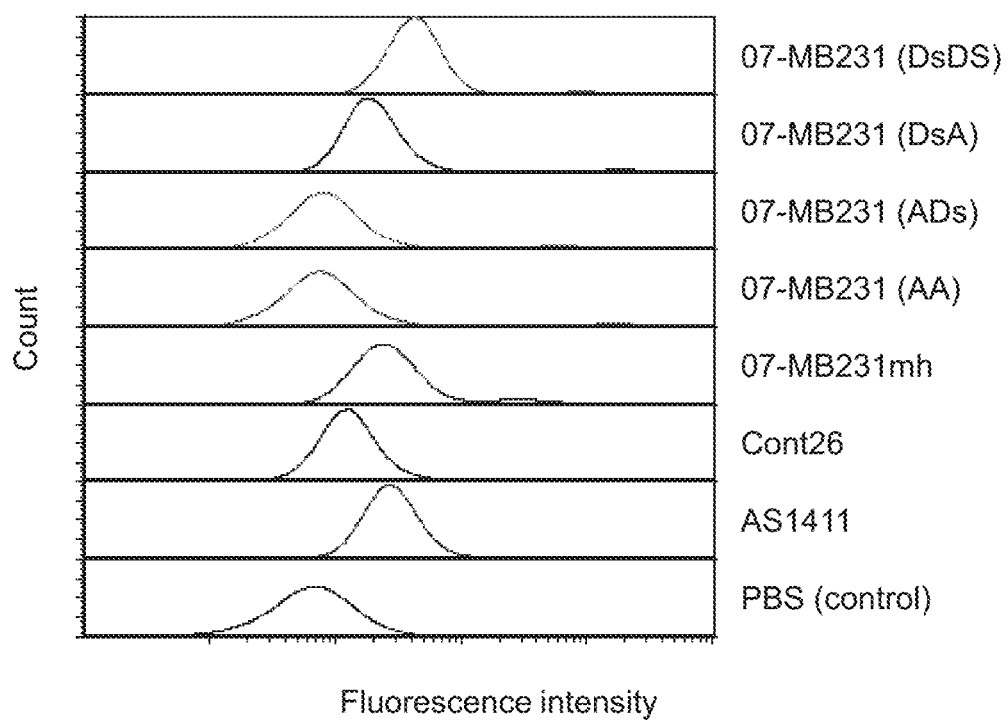
FIG. 18 shows the results of flow cytometric analysis of the cell-binding ability of the DNA aptamers shown in FIG. 17, as well as AS1411, and Cont26.

The results are shown in FIG. 18. The binding ability of both 07-MB231 (DsA) and 07-MB231 (ADs) was lowered and the binding ability of 07-MB231 (ADs) was more significantly lowered. This indicates that 2 Ds bases in the structure are contributed to cell binding and, in particular, 5'-terminal Ds is significantly contributed to cell binding. The binding ability of the DNA aptamer (07-MB231mh) in which a mini-hairpin structure was added at its terminus was also confirmed.

Example 9: Modification of 23-MB231 Aptamer

Figure 19:
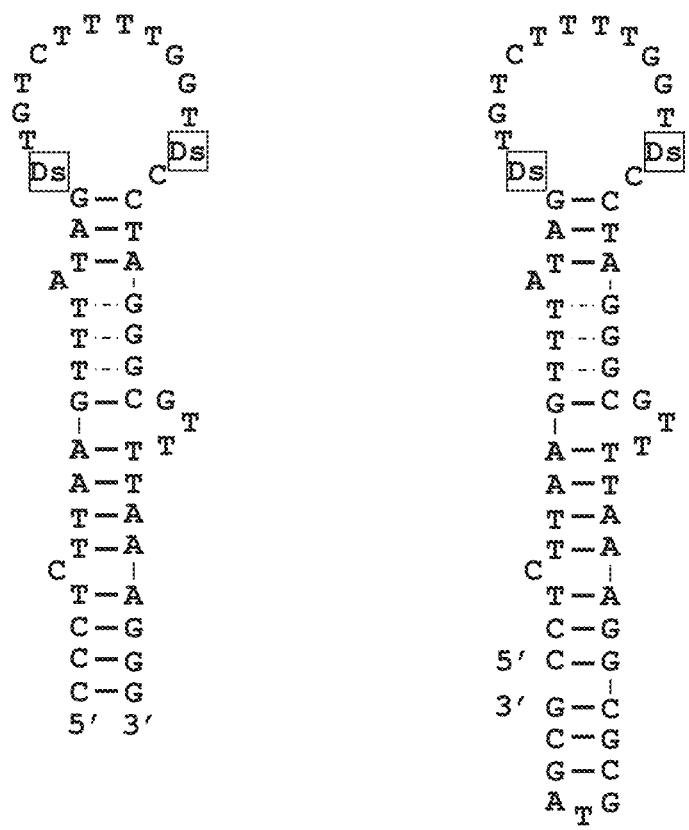
FIG. 19 shows the sequences of the DNA aptamers used in Example 9 and its putative secondary structures. A mini-hairpin structure was added to the terminus of 23-MB231b (SEQ ID NO: 51) to design 23-MB231bmh (SEQ ID NO: 52). Ds is marked as boxed.

The 23-MB231 aptamer was also modified. Specifically, a mini-hairpin structure was added to the terminus of 23-MB231b (SEQ ID NO: 51) to design 23-MB231bmh (SEQ ID NO: 52). Thus, the DNA aptamers comprising the relevant nucleotide sequences were chemically synthesized. (FIG. 19 shows the nucleotide sequences and the secondary structures thereof deduced by doped selection.)

The DNA aptamers were incubated with cells at 250 nM each (25 pmol of Alexa488-labeled DNA/2.5×10⁵ cells/100 µl) at 4° C. for 30 minutes, and the cell-binding ability was examined based on changes in the fluorescence intensity using a flow cytometer as with Example 1.

Figure 20:
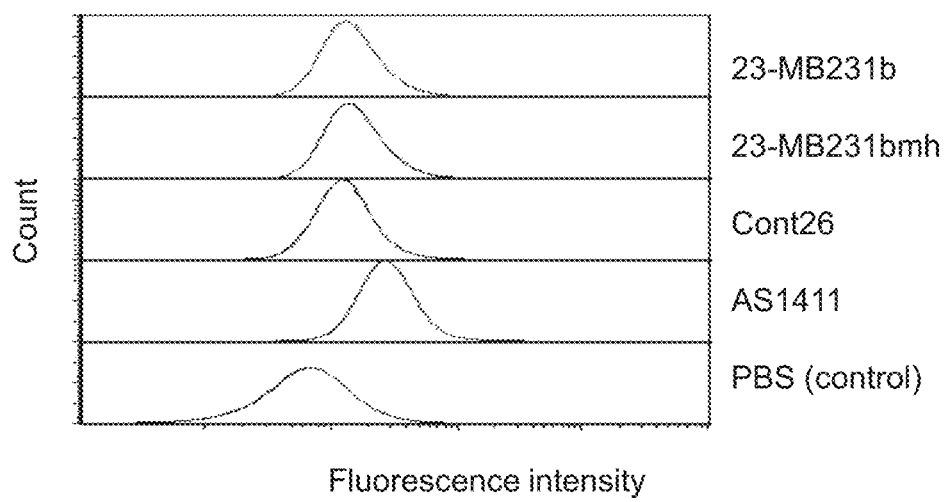
FIG. 20 shows the results of flow cytometric analysis of the cell-binding ability of the DNA aptamers shown in Example 9, as well as AS1411, and Cont26.
Figure 21:
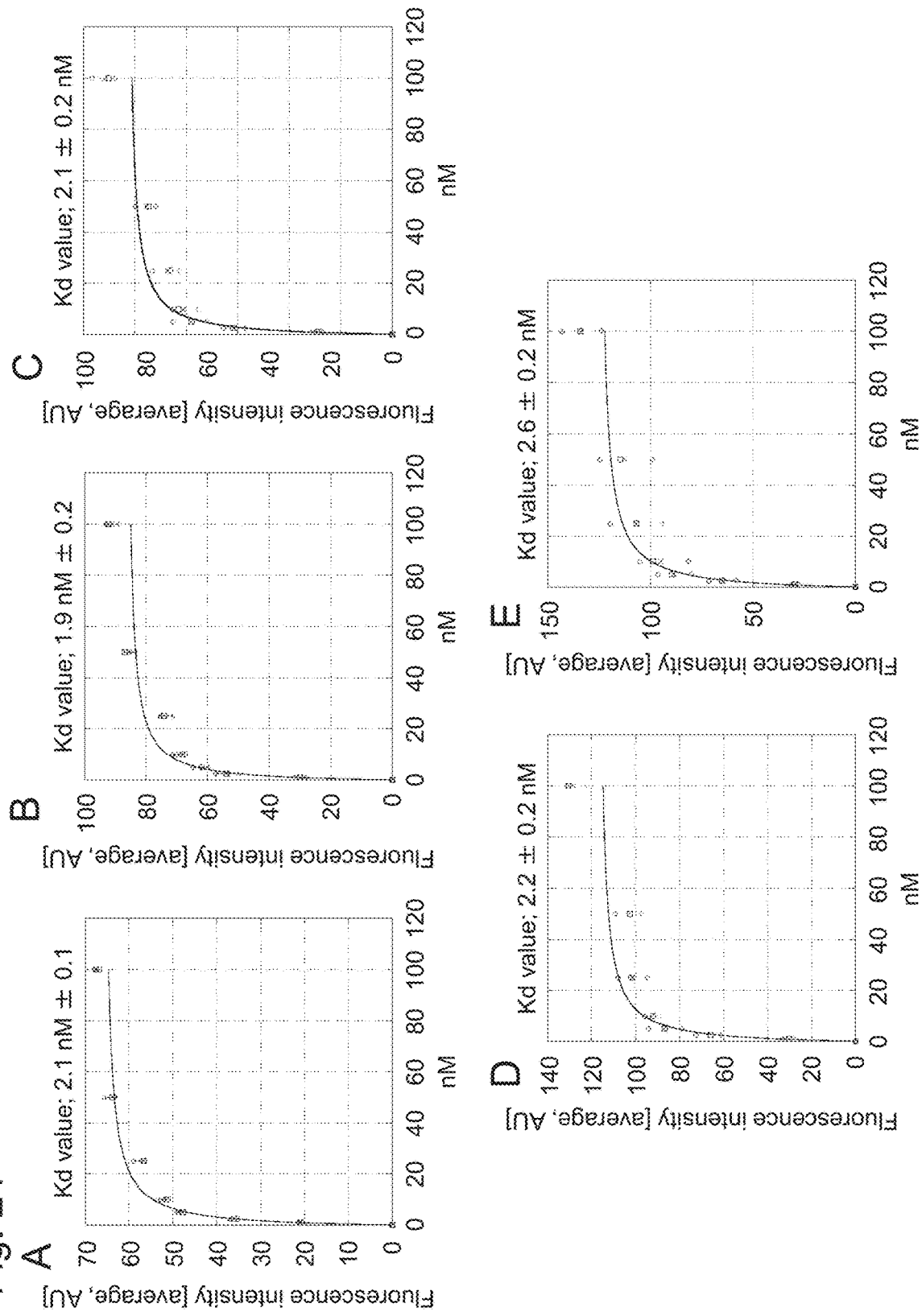
FIG. 21 shows the results of measurement of the Kd values of 14A-MCF7 (37DsDs) and its modified forms analized by a flow cytometry. A horizontal axis represents the concentration of the DNA aptamer and a vertical axis represents the fluorescence intensity. A shows the results of 14A-MCF7 (37DsDs), B shows the results of 14A-MCF7mh (44DsDs), C shows the results of 14A-MCF7mh, D shows the results of 14A-MCF7mh (40DsDs), and E shows the results of 14A-MCF7mh (38DsDs).
Figure 22:
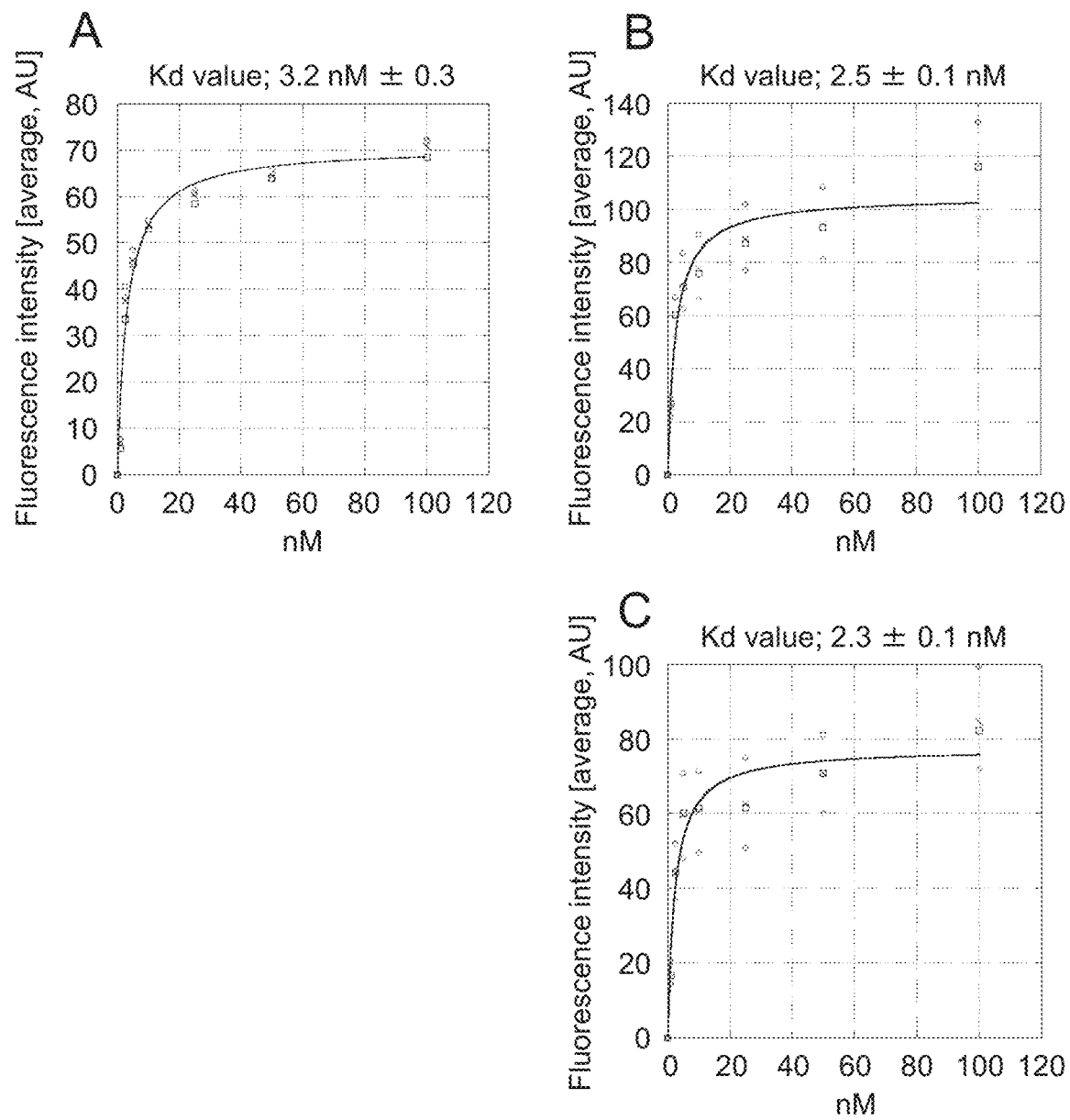
FIG. 22 shows the results of measurement of the Kd values of 08B-MCF7 (51DsDs) and its modified forms analized by a flow cytometry. A horizontal axis represents the concentration of the DNA aptamer and a vertical axis represents the fluorescence intensity. A shows the results of 08B-MCF7 (51DsDs). B shows the results of 08B-MCF7mh, and C shows the results of 08B-MCF7mh2.
Figure 23:
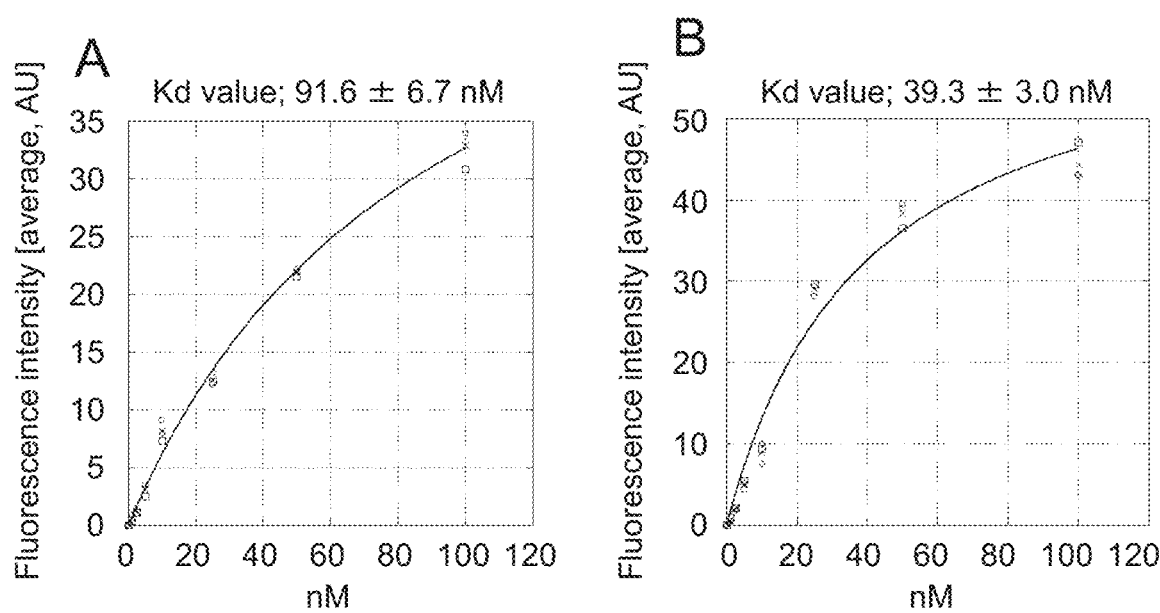
FIG. 23 shows the results of measurement of the Kd values of 03-T47D (DsDs) and its modified form analized by a flow cytometry. A horizontal axis represents the concentration of the DNA aptamer and a vertical axis represents the fluorescence intensity. A shows the results of 03-T47D (DsDs) and B shows the results of 03-T47Dmh.
Figure 24:
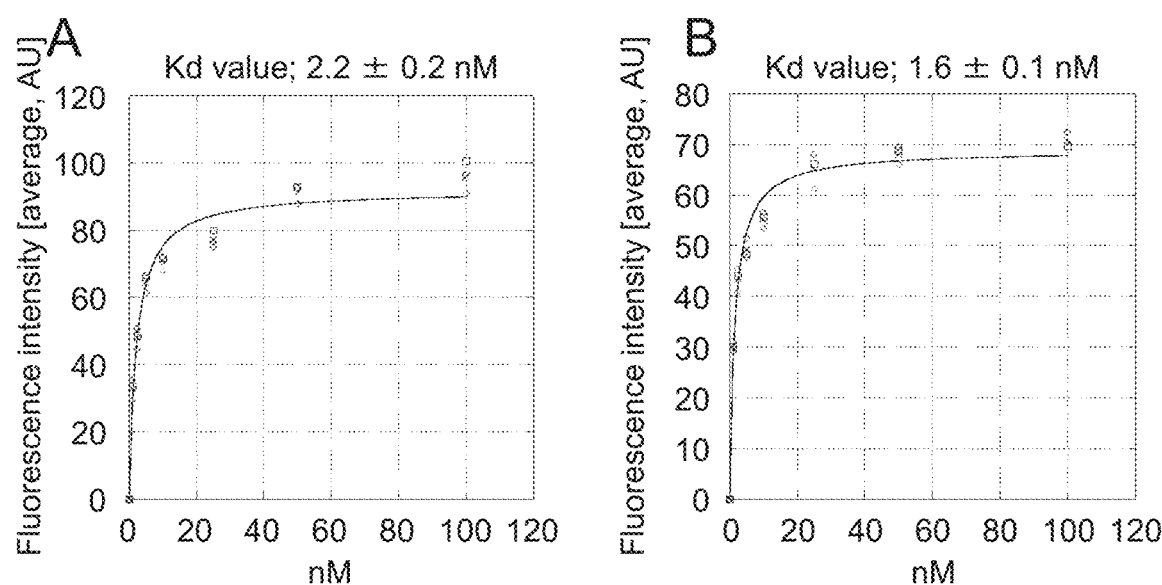
FIG. 24 shows the results of measurement of the Kd values of 05-MB231GC and its modified form analized by a flow cytometry. A horizontal axis represents the concentration of the DNA aptamer and a vertical axis represents the fluorescence intensity. A shows the results concerning 05-MB231GC and B shows the results concerning 05-MB231GCmh.
Figure 26:
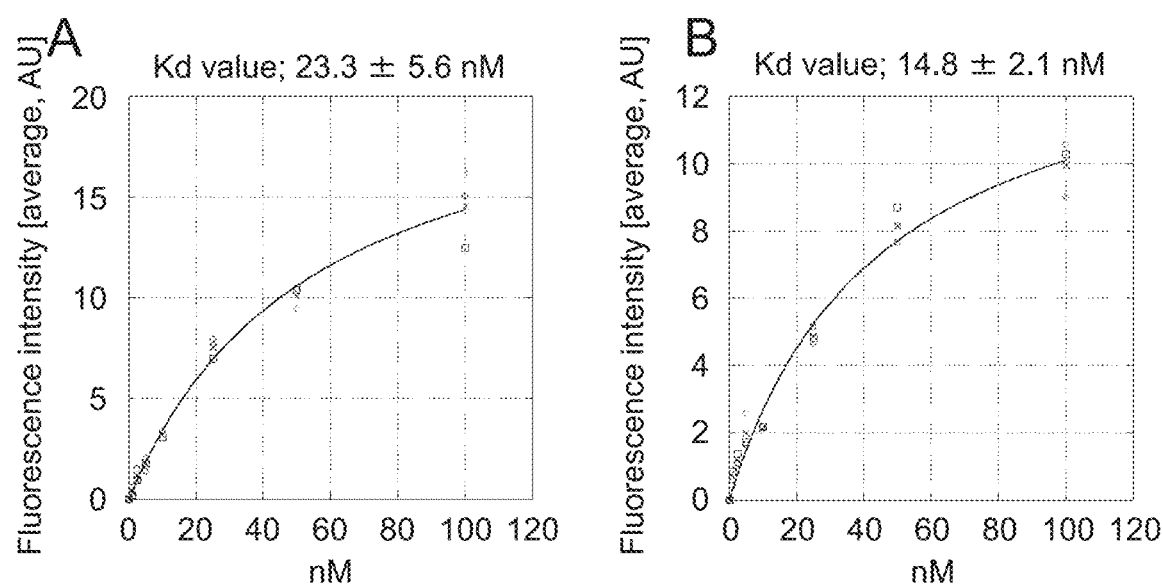
FIG. 26 shows the results of measurement of the Kd values of 23-MB231b and its modified form analized by a flow cytometry. A horizontal axis represents the concentration of the DNA aptamer and a vertical axis represents the fluorescence intensity. A shows the results concerning 23-MB231b and B shows the results concerning 23-MB231bmh.

The results are shown in FIG. 20. The binding activity of the DNA aptamers was examined.

Example 10: Examination of DNA Aptamer Affinity (KD)

Affinity of the optimized and stabilized DNA aptamers to target cell lines was compared and examined. The DNA aptamers were labeled with Alexa488, and changes in the fluorescence intensity caused upon cell binding were analyzed using a flow cytometer.

Specifically, the labeled DNA aptamers were sequentially diluted to the final concentration of 100, 50, 25, 10, 5, 2.5, 1, and 0 nM, and incubated with an enzyme-free suspension of MCF7 (2.5×10⁵ cells) at 4° C. for 30 minutes, and washed two times.

Thereafter, the fluorescence intensity was measured with a flow cytometer (3 times). On the basis of the fluorescence intensity measured at each concentration, the Kd value was determined using Kaleida Graph. The calculation formula: y=m1×M0/(m2+M0) was used.

The results are shown in FIGS. 21 to 26 and Table 8. All the aptamers derived from 08B-MCF7, 14A-MCF7, 05-MB231, and 07-MB231 comprising either fundamental structure or a modified structure comprising a mini-hairpin structure at its terminus had very strong cell-binding ability at several nM levels. The aptamers derived from 03-T47D and 23-MB231 had cell-binding ability at several tens to several nM levels.

TABLE 8

Binding affinity of aptamers to target cell lines

| Aptamer name | Kd value |
| --- | --- |
| 14A-MCF7 (37DsDs) | 2.1 nM ± 0.1 |
| 14A-MCF7mh (44DsDs) | 1.9 nM ± 0.2 |
| 14A-MCF7rmh | 2.1 nM ± 0 2 |
| 14A-MCF7mh (40DsDs) | 2.2 nM ± 0.2 |
| 14A-MCF7mh (38DsDs) | 2.6 nM ± 0.02 |
| 08B-MCF7 (51DsDs) | 3.2 nM ± 0.3 |
| 08B-MCF7mh | 2.5 nM ± 01 |
| 08B-MCF7mh2 | 2.3 nM ± 0.1 |
| 03-T47D (DsDs) | 91.6 nM ± 6.7 |
| 03-T47Dmh | 39.3 nM ± 3.0 |
| 05-MB231GC | 2.2 nM ± 0.2 |
| 05-MB231GCmh | 1.6 nM ± 0.1 |
| 07-MB231 (DsDs) | 2.2 nM ± 0.5 |
| 07-MB231mh | 2.0 nM ± 0.3 |
| 23-MB231b | 23.3 nM ± 5.6 |
| 23-MB231bmh | 2.5 nM ± 0.9 |

Example 11: Determination of Tm Value

The Tm values of aptamers derived from the 14A-MCF7 aptamer and aptamers derived from the 08B-MCF7 aptamer were measured using UV-2450 (Shimadzu Corporation) (the average of 3 measurements).

Specifically, the DNA aptamers were diluted with D-PBS (−) to prepare a 5-ml round tube comprising 260 pmol/130 µl each thereof. After the samples were heated at 95° C. for 3 minutes, the tubes were degassed in a desiccator for 1 minute. These samples were transferred to cuvettes, the temperature was raised by 0.5° C. per second within a range of 15° C. to 100° C., and the absorbance at 260 nm was then measured. The data was graphed using IGOR pro, and shown as the average of 3 measurements.

Figure 27:
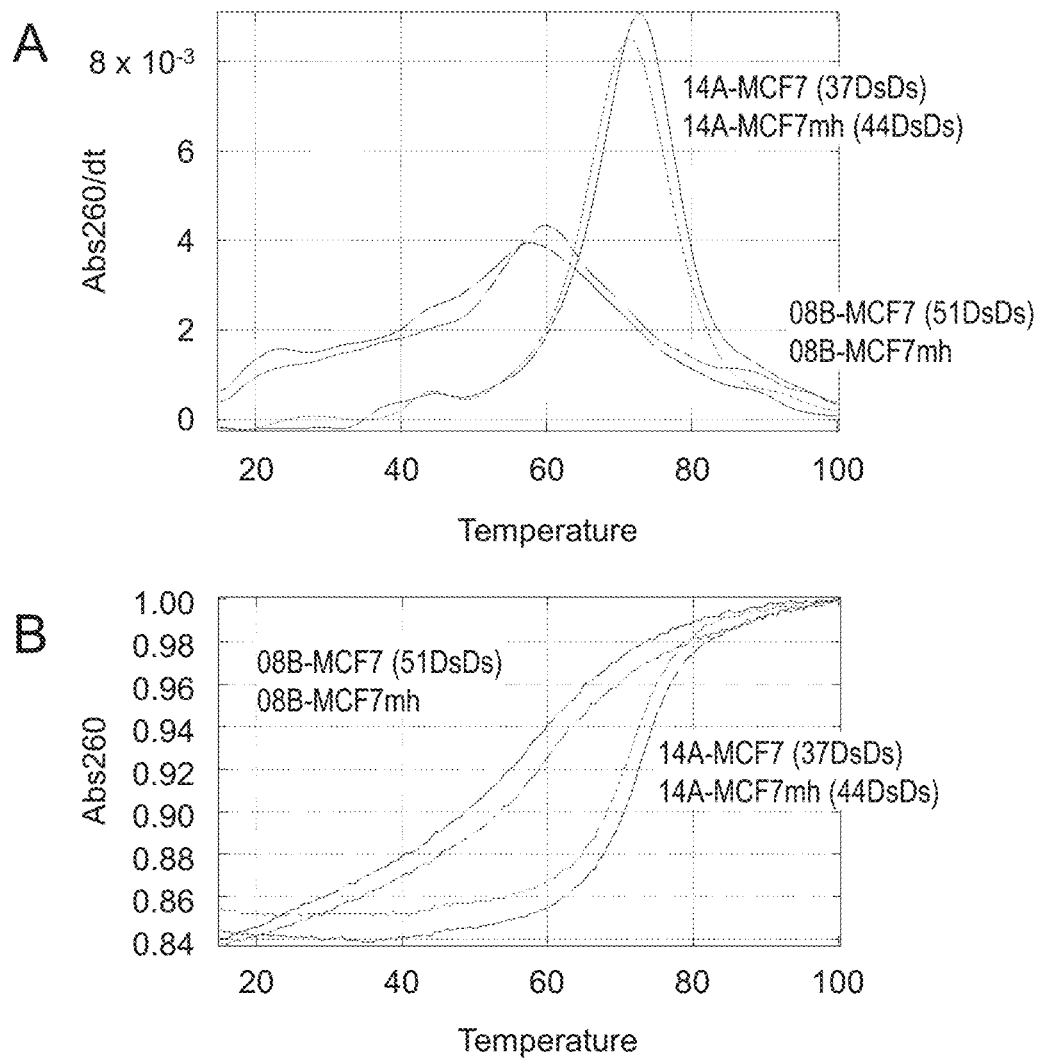
FIG. 27 shows the results of measurement of the Tm values of 14A-MCF7 (37DsDs) and 14A-MCF7mh (44DsDs) in addition to 08B-MCF7 (51DsDs) and 08B-MCF7mh. A horizontal axis represents temperature. A shows a first-derivation of the absorbance at 260 nm and B shows the absorbance at 260 nm.

The results are shown in FIG. 27 and Table 9.

TABLE 9

Tm values of aptamers

| Aptamer name | Tm value |
| --- | --- |
| 08B-MCF7 (51DsDs) | 57.2° C. |
| 08B-MCF7mh | 59.7° C. |
| 08B-MCF7mh2 | 57.0° C. |
| 14A-MCF7 (35DsDs) | 71.5° C. |
| 14 A-MCF7mh (44DsDs) | 73.0° C. |
| 14A-MCF7mh | 68.0° C. |
| 14 A-MCF7tmh (40DsDs) | 64.7° C. |
| 14A-MCF7 (38DsDs) | 59.9° C. |

While the absorbance of the aptamer derived from 14A-MCF7 at 260 nm began to sharply change at around 60° C., that of the aptamer derived from 08B-MCF7 moderately changed. This indicates that the aptamer derived from 14A-MCF7 has structurally superior heat stability to the aptamer derived from 08B-MCF7.

Example 12: Competitive Binding Inhibition Assay

Cell-binding properties of the 4 types of aptamers exhibiting particularly high cell-binding ability (14A-MCF7mh, 08B-MCF7mh, 05-MB231GCmh, and 07-MB231mh) were analyzed via competitive experiment to examine whether or not these aptamers bind to the same target. Specifically, the DNA aptamers were labeled with Alexa488, and whether or not the fluorescence intensity at around their Kd value changes upon cell binding was analyzed in the presence of other DNA aptamers using a flow cytometer.

Specifically, the final concentration of the labeled DNA aptamer was adjusted to 2.5 or 5 nM, and the competitive DNA aptamers were mixed therewith at 0, 1, 2.5, 5, 10, 25, 50, or 100 nM. These DNA aptamers were each incubated with an enzyme-free suspension of MCF7 ($2.5 \times 10^5$ cells) at 4° C. for 30 minutes and washed two times with a wash buffer (0.45% glucose, 5 mM $MgCl_2$). Thereafter, the fluorescence intensity was measured using a flow cytometer. The cell used were MCF7 cell line when 14A-MCF7mh and 08B-MCF7mh were used as fluorescence-labeled aptamers, and MDA-MB-231 cell when 05-MB231GCmh and 07-MB231 mh were used as fluorescence-labeled aptamers.

The results are shown in Table 10. While a binding competition was observed between 14A-MCF7mh and 08B-MCF7mh2, cell-binding activity of 05-MB231GCmh and 07-MB231mh was not interfered in the presence of other DNA aptamers. This indicates that 14A-MCF7mh and 08B-MCF7mh2 bind to the same target, whereas 05-MB231GCmh and 07-MB231mh each bind specifically to different targets.

TABLE 10

|  | 08B-MCF7mh2 | 14A-MCF7mh | 05-MB231GCmh | 07-MB231mh |
|---|---|---|---|---|
| 14A-MCF7mh | + | + | − | − |
| 05-MB231GCmh | − | − | + | − |
| 07-MB231mh | − | − | − | + |

Example 13: Cell-Binding Specificity of DNA Aptamers

In order to examine binding specificity of the DNA aptamers obtained, the Alexa488-labeled aptamers were incubated with various cultured cancer cell lines, and the presence or absence of the binding was analyzed on the basis of changes in the fluorescence intensity using a flow cytometer as with Example 1. This analysis was carried out based on changes in the fluorescence intensity with the use of AS1411 as a positive control and AS1411 mutant, Cont26 as a negative control. The aptamer observed to exhibit a fluorescence intensity lower than that of Cont26 was indicated by the symbol "−," the aptamer observed to exhibit a fluorescence intensity higher than that of Cont26 was indicated by the symbol "+," and the aptamer observed to exhibit a fluorescence intensity higher than that of AS1141 was indicated by the symbol "++."

The results are shown in Table 11.

TABLE 11

| Tissue | Cell line | Origin | 08B-MCF7mh2 | 14A-MCF7mh | 05-MB231GCmh | 07-MB231mh | 03-T47Dmh | AS1411 |
|---|---|---|---|---|---|---|---|---|
| Breast | MCF7 | Epithelial breast cancer established from metastatic focus (pleural fluid) | ++ | ++ | ++ | − | + | + |
|  | T-47D | Epithelial ductal breast cancer established from metastatic focus (pleural fluid) | − | − | ++ | − | ++ | + |
|  | MDA-MB-231 | Epithelial breast cancer established from metastatic focus (pleural fluid) | − | − | ++ | ++ | ++ | + |
|  | MDA-MB-453 | Epithelial breast cancer established from metastatic focus (pericardial fluid) | − | − | ++ | − | ++ | + |
| Liver | PLC/PRT/5 | HBV-infected hepatic cell (Alexander cell) | − | − | ++ | − | + | + |
| Pancreas | MIAPaCa-2 | Pancreatic adenocarcinoma | − | − | ++ | − | ++ | + |
|  | PANC-1 | Pancreatic ductal adenocarcinoma | − | − | ++ | − | ++ | + |
| Prostate gland | PC-3 | Established from metastatic focus (bone) of Grade IV patient | − | − | ++ | ++ | ++ | + |
| Ovary | NIH:OVCAR-3 | Serous adenocarcinoma | − | − | ++ | − | + | + |
| Colon | HCT116 | Colorectal adenocarcinoma | − | − | ++ | − | + | + |
| Stomach | MKN45 | Anaplastic gastric adenocarcinoma | − | − | ++ | − | ++ | + |
| Uterine cervix | HeLa | Epithelial cancer of uterine cervix | − | − | ++ | − | + | + |
| Leukemia | KG-1 | Acute myelocytic leukemia | − | − | ++ | − | ++ | + |
|  | CCRF-CEM | Acute lymphoblastic leukemia | − | − | ++ | − | ++ | + |
| Lung | A549 | Epithelial adenocarcinoma (alveolar basal epithelial cells) | − | − | ++ | ++ | ++ | ++ |
| Non-cancer cell | MCF10A | Mammary gland epithelium of fibrous disease of breast | − | − | − | − | − | + |
|  | HUVEC | Human umbilical vein endothelial cells | − | − | − | − | − | + |

As shown in Table 11, both 14A-MCF7mh and 08B-MCF7mh2 exhibited sharp changes in the fluorescence intensity indicating binding, only for MCF7 cell line. Also, 07-MB231mh was observed to specifically bind to the MDA-MB-231 cell line. Meanwhile, 03-T47Dmh and 05-MB231GCmh were observed to bind to most cancer cell lines other than non-cancer cells.

Example 14: Examination of Intracellular Localization of DNA Aptamer

In order to examine binding localization of the DNA aptamers, the Alexa488-labeled DNA aptamer (250 nM) was incubated with cells in OPTI-MEM (GibcoBRL) at 4° C. or 37° C. for 30 minutes. The origin cells of the DNA aptamers were used. 75 nM of LysoTracker Red DND-99 (Molecular Probes) which stains the late endosome and lysosome was added to the medium and used as an intracellular organelle marker for indicator of localization. The incubated cells were fixed with 4% paraformaldehyde, stained with DAPI, and sealed to prepare samples. These samples were observed under a fluorescence microscope (ECLIPSE Ti, NiKon Corporation) and an FV10i or FV1200 (Olympus Corporation) confocal microscope.

Figure 28:
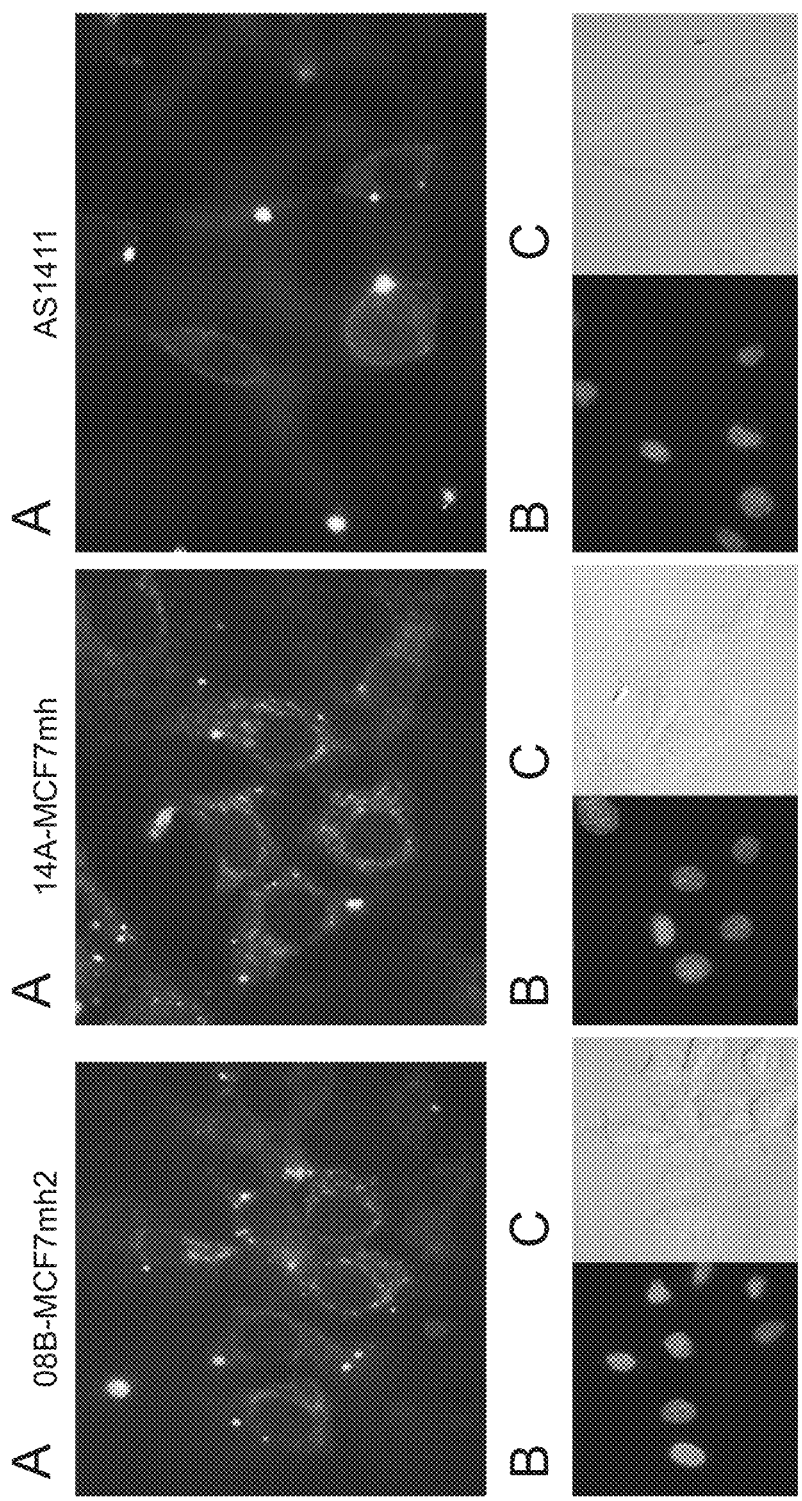
FIG. 28 shows the binding to the cells and cell localization of the DNA aptamers (08B-MCF7mh2, 14A-MCF7mh, and AS1411). The fluorescence image of Alexa488 is shown in A, the fluorescence image of DAPI is shown in B, and the transmission image is shown in C.
Figure 29:
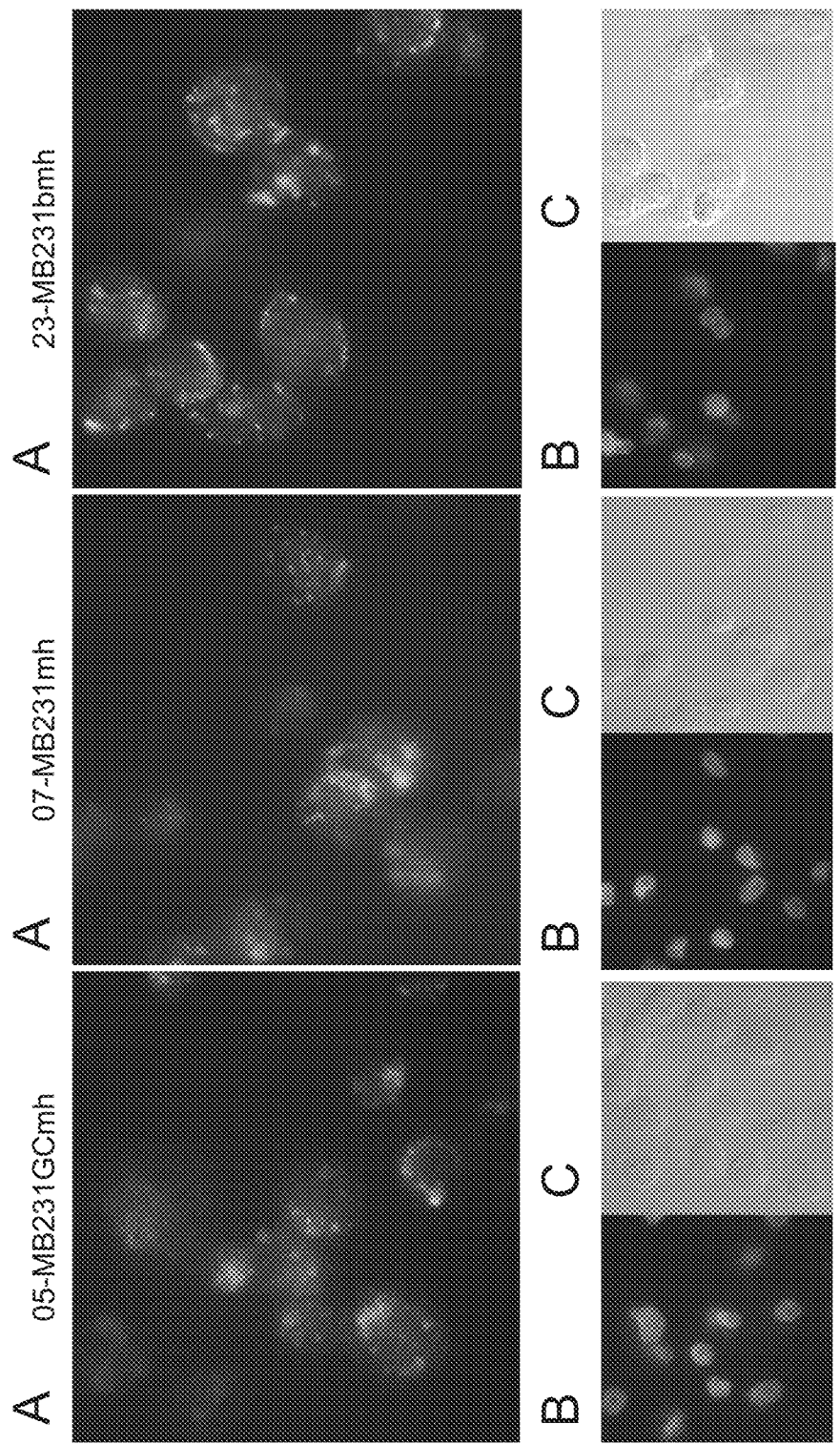
FIG. 29 shows the results of analysis of binding of the DNA aptamers (05-MB231GCmh, 07-MB231mh, and 23-MB231bmh) to the cells and cell localization thereof. A shows the results based on the fluorescence observed with Alexa488. B shows the results based on the fluorescence observed with DAPI, and C shows the results observed under a transmitted beam.
Figure 30:
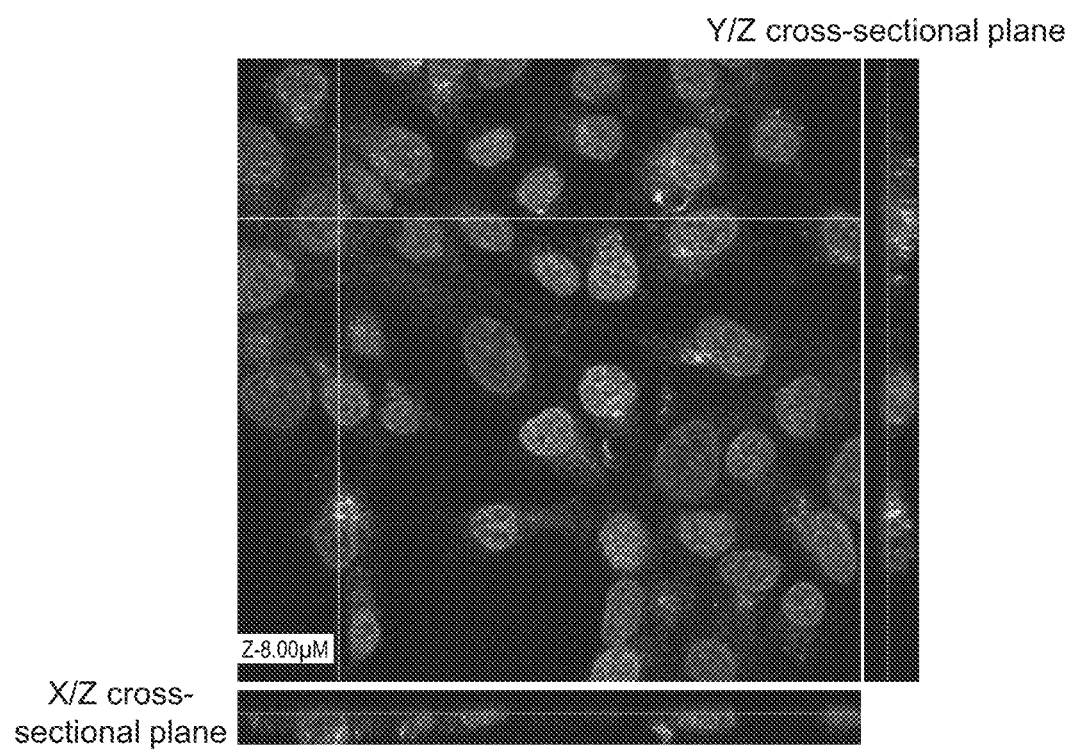
FIG. 30 shows the results of analysis of binding of the 14A-MCF7mh (44DsDs) aptamer to the cells and cell localization thereof.

The results are shown in FIGS. 28 to 31. All the DNA aptamers were observed to bind to the cell surface because of dot-like Alexa488 fluorescence scattered on the cell surface (FIGS. 28 and 29). Among them, in confocal microscopic observation using 14A-MCF7mh, Alexa488 fluorescence was localized not only in the cell surface but also the endosome (colocalized with LysoTracker) (FIG. 30). This indicates that the 14A-MCF7mh aptamer bound to a target on the cell membrane surface is incorporated into the cell via endocytosis and it is gradually transferred to the endosome (i.e., the lysosome).

Figure 31:
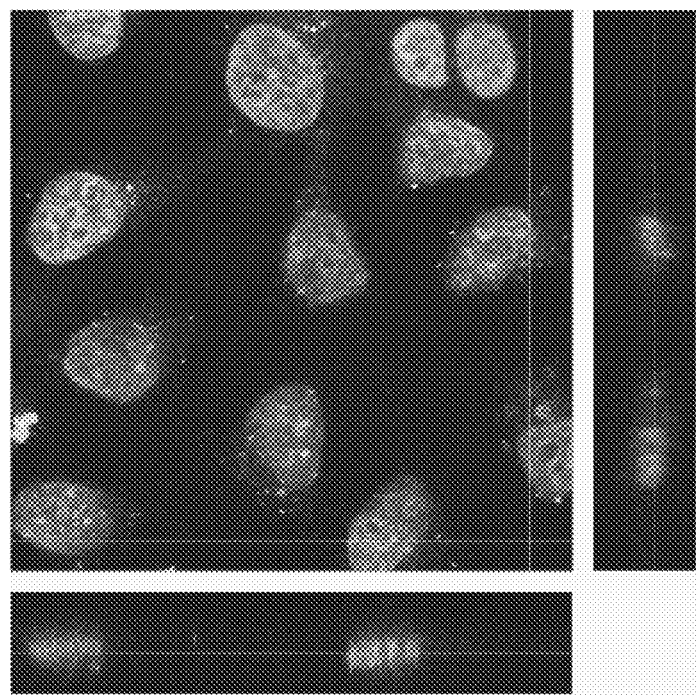
FIG. 31 shows the results of analysis of binding of AS1411 to the cells and cell localization thereof.

In contrast, dot-like localization of AS1411 used as a positive control was observed on the cell surface (not consistent with localization detected with LysoTracker) (FIG. 31). This indicates that the endocytic mechanism of the DNA aptamer according to the present invention is different from that of AS1141 (i.e., their targets are different).

Example 15: Examination of Effect of DNA Aptamer on Cultured Cell

Cell growth inhibitory effects of the DNA aptamers were examined, using various cultured cancer cell lines. Various adhesive cancer cells (MCF7/MEM medium. T47D/RPMI medium, MDA-MB-231/DMEM medium, MDA-MB-453/DMEM medium. MIAPaca2/RPMI medium. PC-3/RPMI medium, HCT-116/DMEM medium, A549/DMEM medium) were seeded on a 96-well plate to be a concentration of $1 \times 10^3$ to $2.5 \times 10^3$ cells/well on the day before the drug was added. The myelocytic leukemia-derived cell line KG-1 (RPMI medium) was seeded to be $4 \times 10^4$ cells/ml and 90 μl/well about 2 hours before the drug was added. The non-cancer cells (MCF10A and HUVEC) were seeded to be $4 \times 10^3$ cells/well.

The DNA aptamers were diluted to 100 μM with D-PBS (−), heated at 95° C. for 5 minutes, and then allowed to stand at room temperature for 20 minutes or longer for folding. AS1411 and Cont26 were used as nucleic acid control samples, and diluted to 50 μM or 100 μM with D-PBS(−), and then gradually cooled at 1° C./min from 95° C. for folding. As control samples of low-molecular-weight compounds, conventional anticancer agents; i.e., Paclitaxel (Sigma-Aldrich Co., LLC., abbreviated as PTX, final concentration: 10 nM), and floxuridine (Nacalai Tesque, abbreviated as FUdR, final concentration: 10 nM) were used. The DNA aptamers were diluted 10-fold to be the final concentration in the designated media at 1, 2.5, 5, or 10 μM and added to the cells via medium exchange (adherent cell). Alternatively, 10 μl of the sample diluted with D-PBS(−) to 10-hold concentration of the final concentration was directly added to the cell solution. PTX and FUdR were diluted 1,000-fold and 10-fold, respectively, with the media and added to the cells. The media D-PBS(−) and DMSO by themselves were designated as treatment groups as control media. After adding drugs, cells were cultured for 4 days (adherent cell culture) or 3 days (floating cell culture). Assays were carried out using a living cell counting reagent (WST-8 assay reagent, Nacalai Tesque, the absorbance at 450 nm of each well was assayed using the Arvo multilabel counter (Perkin Elmer)), and the results were normalized to the group subjected only to medium exchange so as to evaluate the cell growth.

Figure 3:
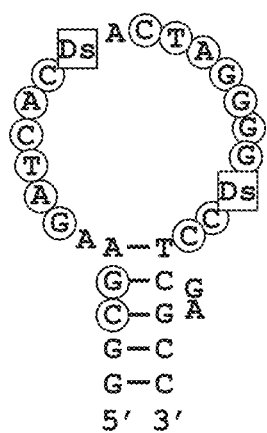
FIG. 3 shows the sequence of the DNA aptamer (03-T47D) (SEQ ID NO: 27) selected by Cell-SELEX targeting the T47D cells and the putative secondary structure. A base found to have a degree of conservation of 85% or higher in a second selection is circled and a Ds is boxed.
Figure 4:
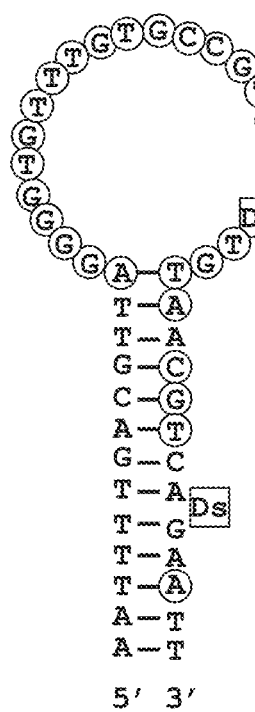
FIG. 4 shows the sequence of the DNA aptamer (05-MB231) (SEQ ID NO: 34) selected by Cell-SELEX targeting the MB231 cells and the putative secondary structure. A base found to have a degree of conservation of 85% or higher in a second selection is circled and a Ds is boxed.
Figure 5:
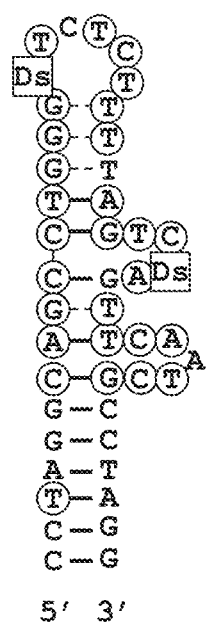
FIG. 5 shows the sequence of the DNA aptamer (07-MB231) (SEQ ID NO: 42) selected via Cell-SELEX targeting the MB231 cells and the putative secondary structure. A base found to have a degree of conservation of 85% or higher in a second selection is circled and a Ds is boxed.
Figure 6:
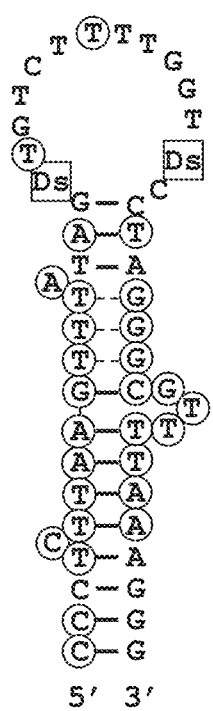
FIG. 6 shows the sequence of the DNA aptamer (23-MB231) (SEQ ID NO: 49) selected by Cell-SELEX targeting the MB231 cells and the putative secondary structure. A base found to have a degree of conservation of 85% or higher in a second selection is circled and a Ds is boxed.
Figures 1, 32:
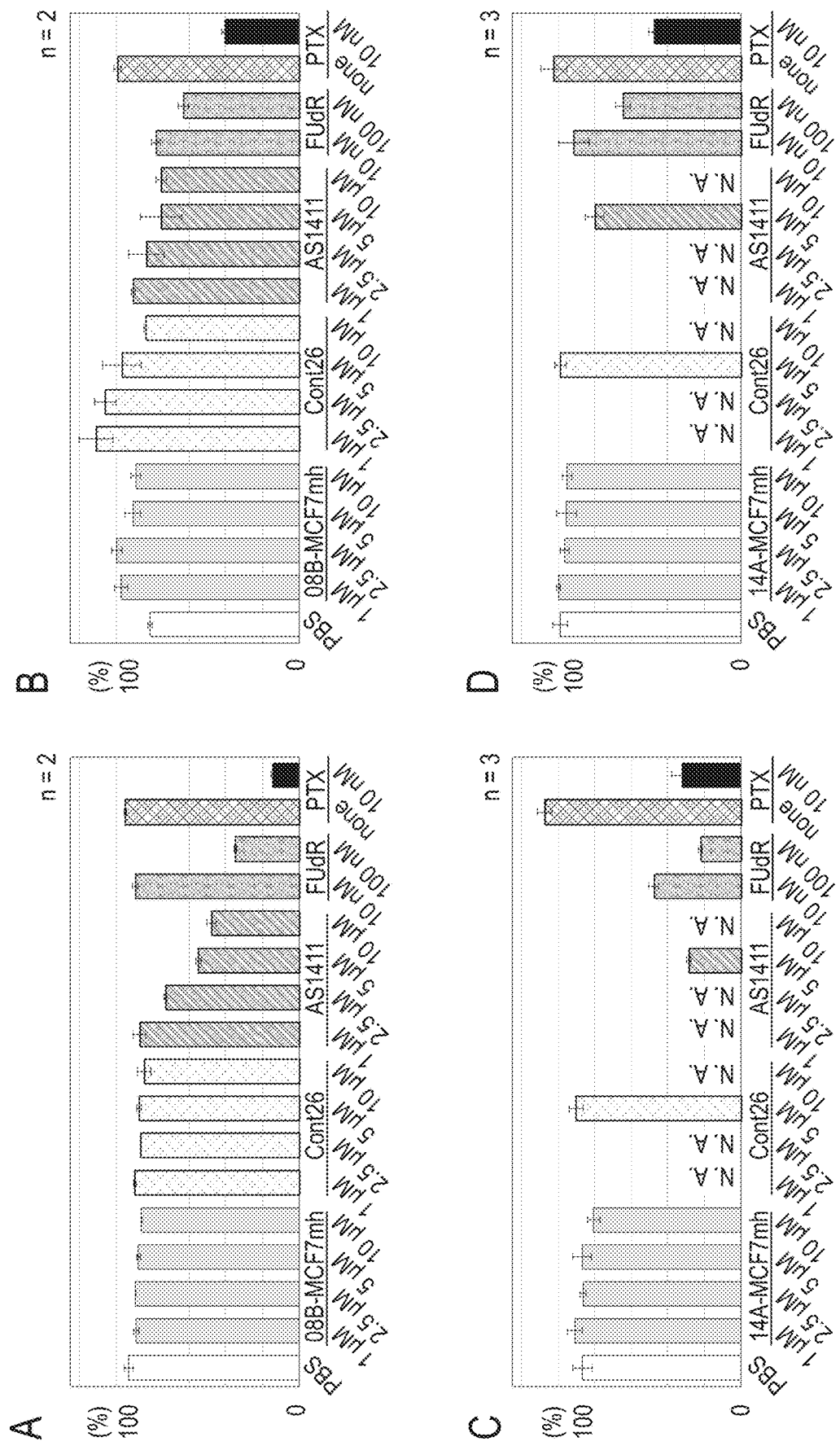
Figures 2, 32:
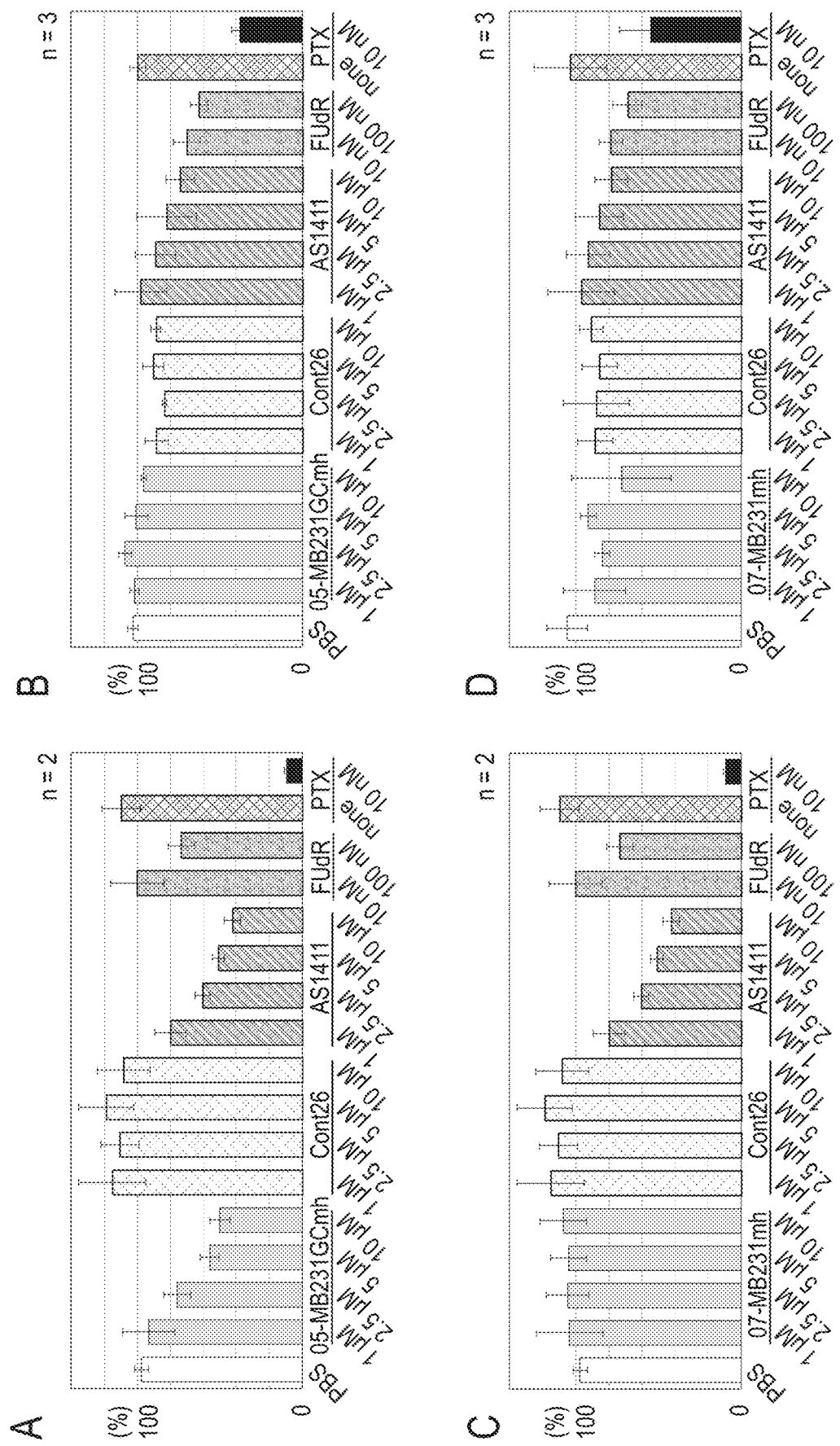
Figures 3, 32:
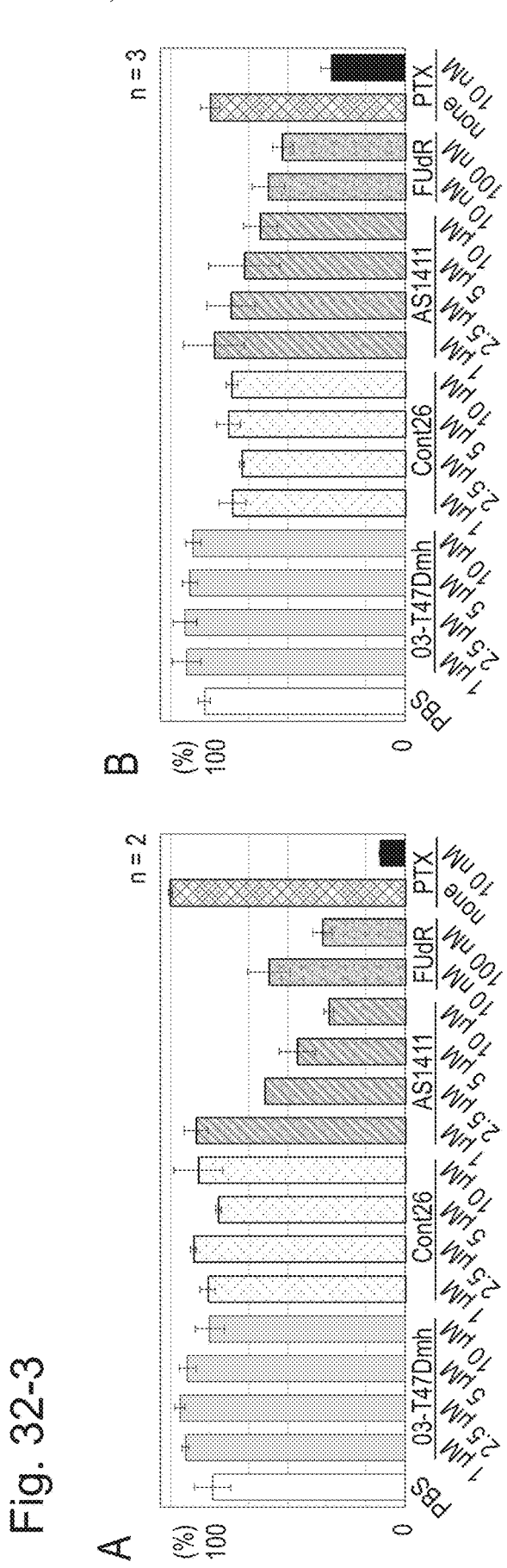

FIGS. 32-1 to 32-3 show the results of growth inhibitory effects of the non-fluorescence-labeled DNA aptamers (08B-MCF7mh, 14A-MCF7mh, 05-MB231GCmh, 07-MB231mh, and 03-T47Dmh) on target cancer cells used to obtain the DNA aptamers (i.e., MCF7 cells in the case of 08B-MCF7mh and 14A-MCF7mh. MB231 cells in the case of 05-MB231GCmh and 07-MB231mh, and T47D cells in the case of 03-T47Dmh). As with a positive control AS1411, 05-MB231GCmh was found to exert the cell growth inhibitory effects in a concentration-dependent manner, and 05-MB231GCmh was found to exert no growth inhibitory effects on non-cancer cells (MCF10A). As with a negative control Cont26, DNA aptamers other than 05-MB231GCmh were found to have no effect on the growth of the target cancer cells or non-cancer cells.

Figures 1, 33:
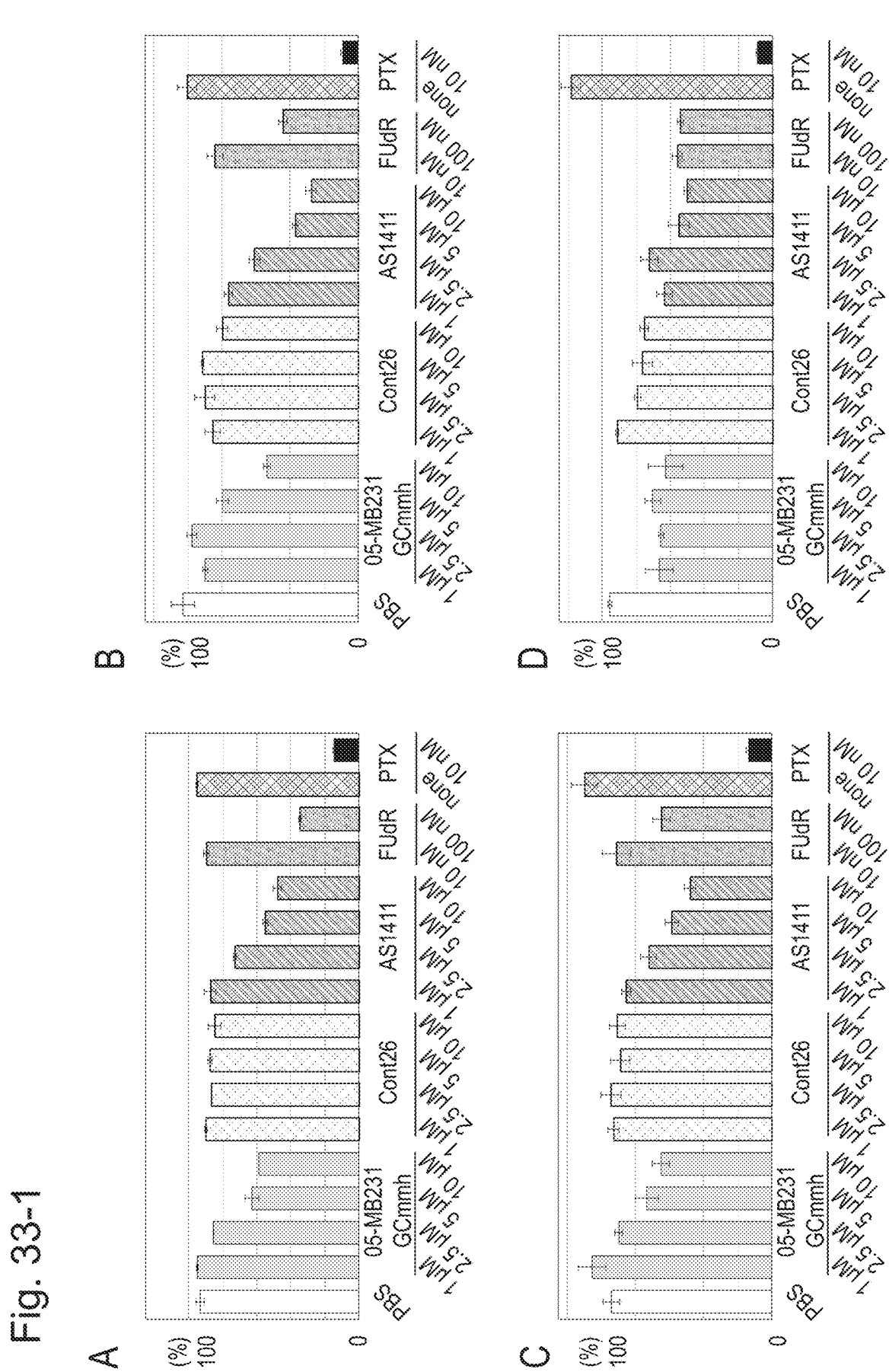

FIGS. 33-1 to 33-3 show the results of growth inhibitory effects of 05-MB231GCmmh (SEQ ID NO: 80), a single-nucleotide substituent of 05-MB231GCmh which exhibits the cell growth inhibitory effects on the target cancer cells, on various cancer cells. As with the case of 05-MB231GCmh, 05-MB231GCmmh was found to exert effects of the growth inhibition not only on the target cancer cell line MDA-MB231, but also on various cancer cells, in a concentration-dependent manner. As shown in FIGS. 32-1 to 32-3, also, substantially no growth inhibitory effects were observed on non-cancer cell lines such as MCF10A and HUVEC.

All publications, patents, and patent applications cited herein are incorporated herein by reference in their entirety.

The invention claimed is:

1. A DNA aptamer that binds to a cancer cell comprising the nucleotide sequence (i) or (ii) below:
   (i) (a) a nucleotide sequence represented by $N_1N_2N_3N_4N_5AGGGGTGTTTGTGCCGTGAGN_{26}TGTN_{30}N_{31}N_{32}N_{33}N_{34}$ (SEQ ID NO: 35), wherein $N_1$ to $N_5$ each independently represent G, T, A, or C, $N_{26}$ represents 7-(2-thienyl)-3H-imidazo[4,5-b]pyridin-3-yl, $N_{30}$ forms a base pair with $N_5$, $N_{31}$ forms a base pair with $N_4$, $N_{32}$ forms a base pair with $N_3$, $N_{33}$ forms a base pair with $N_2$, and $N_{34}$ forms a base pair with $N_1$), or
   (b) a nucleotide sequence in which one to six nucleotides are added, removed, and/or substituted in the nucleotide sequence (i)(a) at position(s) other than the position of $N_{26}$; and
   (ii) (a) a nucleotide sequence represented by $N_1N_2N_3N_4N_5N_6GATCACN_{13}N_{14}CTAGGGGN_{22}CCN_{25}N_{26}N_{27}N_{28}N_{29}N_{30}N_{31}$ (SEQ ID NO: 28), wherein, $N_1$ to $N_6$, $N_{14}$, and $N_{25}$ each independently represent G, T, A, or C, $N_{13}$ and $N_{22}$ each represent 7-(2-thienyl)-3H-imidazo[4,5-b]pyridin-3-yl, $N_{26}$ forms a base pair with $N_4$, $N_{29}$ forms a base pair with $N_3$, $N_{30}$ forms a base pair with $N_2$, $N_{31}$ forms a base pair with $N_1$, and $N_{27}$ and $N_{28}$ each independently represent G, T, A, or C or none), or
   (b) a nucleotide sequence in which one to six nucleotides are added, deleted, and/or substituted in the nucleotide sequence (ii)(a) at position(s) other than the positions of $N_{13}$ and $N_{22}$.

2. The DNA aptamer according to claim 1, wherein the nucleotide sequence (i) (a) or (ii) (a) further comprises 1 to 5 GC base-pairs at its terminus.

3. The DNA aptamer according to claim 1, wherein the nucleotide sequence (i)(a), the base pair formed between $N_{30}$ with $N_5$, and/or $N_{31}$ with $N_4$, and/or $N_{32}$ with $N_3$, and/or $N_{33}$ with $N_2$, and/or $N_{34}$ with $N_1$ is a GC pair,
   wherein the nucleotide sequence (ii)(a), the base pair formed between $N_{26}$ with $N_4$, and/or $N_{29}$ with $N_3$, and/or $N_{30}$ with $N_2$, and/or $N_{31}$ with $N_1$ is a GC pair.

4. The DNA aptamer according to claim 1, wherein the one or several nucleotides of the nucleotide sequence (i) (b) are added, removed, and/or substituted at position(s) 1 to 5 or 30 to 34 of SEQ ID NO: 35.

5. The DNA aptamer according to claim 1, wherein the one or several nucleotides of the nucleotide sequence (ii) (b) are added, removed, and/or substituted at position(s) 1 to 6, 14, or 25 to 31 of SEQ ID NO: 28.

6. The DNA aptamer according to claim 1, wherein the nucleotide sequence (i) (a) is the sequence as shown in SEQ ID NO: 36, 37, or 40.

7. The DNA aptamer according to claim 1, wherein the nucleotide sequence (ii) (a) is the sequence as shown in SEQ ID NO: 29.

8. The DNA aptamer according to claim 1, which further comprises a mini-hairpin structure at the 3'-terminus of the aptamer, wherein the mini-hairpin structure is composed of the nucleic acid regions (A) to (C) below sequentially ligated from the 5'-terminus to the 3'-terminus:
   (A) a first nucleic acid region consisting of 2 to 5 random nucleotides;
   (B) a second nucleic acid region consisting of a nucleotide sequence of GNA or GNNA (wherein each "N" independently represents any of G, T, A, or C); and
   (C) a third nucleic acid region consisting of a nucleotide sequence complementary to the first nucleic acid region,
   wherein the first nucleic acid region and the third nucleic acid region form a stem portion by base pairing, and the second nucleic acid region forms a loop portion.

9. A cancer detecting agent comprising the DNA aptamer according to claim 1.

10. A cancer cell detecting kit comprising the DNA aptamer according to claim 1.

11. A pharmaceutical composition comprising the DNA aptamer according to claim 1.

12. An anticancer agent consisting of the DNA aptamer of the nucleotide sequence (i) (a) or (b) according to claim 1.

13. A pharmaceutical composition for delivering a drug to a cancer cell, comprising the DNA aptamer according to claim 1 and a drug.

14. A method for detecting a cancer cell comprising:
   a step of contacting a sample containing cells obtained from a subject with the DNA aptamer according to claim 1; and
   a step of detecting a cancer cell based on the binding between the sample and the DNA aptamer.

15. A method for classifying cancer cells obtained from a subject comprising:
   a step of contacting cancer cells obtained from a subject with the DNA aptamer according to claim 1;
   a step of determining the presence or absence of the binding between the cancer cells and the DNA aptamer, or measuring the strength of the binding; and
   a step of classifying cancer cells based on the presence or absence of the binding, or the strength of the binding.

16. The DNA aptamer according to claim 1, which further comprises a mini-hairpin structure, wherein the mini-hairpin structure is composed of the nucleic acid regions (A) to (C) below sequentially ligated from the 5'-terminus towards the 3'-terminus:
   (A) a first nucleic acid region consisting of 2 to 5 random nucleotides;
   (B) a second nucleic acid region consisting of a nucleotide sequence of GNA or GNNA (wherein each "N" independently represents any of G, T, A, or C); and
   (C) a third nucleic acid region consisting of a nucleotide sequence complementary to the first nucleic acid region,
   wherein the first nucleic acid region and the third nucleic acid region form a stem portion by base pairing, and the second nucleic acid region forms a loop portion.

* * * * *

SEQUENCE LISTING

```
<160> NUMBER OF SEQ ID NOS: 83

<210> SEQ ID NO 1
<211> LENGTH: 53
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (28)..(28)
<223> OTHER INFORMATION: n is
      7-(2-thienyl)-3H-imidazo[4,5-b]pyridine-3-yl

<400> SEQUENCE: 1
```
caggctgtct ctagtcngtc gaactgtnat gagcgtgcta gggggagggt ctg    53

<210> SEQ ID NO 2
<211> LENGTH: 31
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is
    7-(2-thienyl)-3H-imidazo[4,5-b]pyridine-3-yl or A
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, t, or none
<220> FEATURE:
<221> NAME/KEY: misc_feature
<222> LOCATION: (31)..(31)
<223> OTHER INFORMATION: n is a, c, g, or t

<400> SEQUENCE: 2
nnnncnntcg aactgnnatg agngtnnnnn n    31

<210> SEQ ID NO 3
<211> LENGTH: 53
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (17)..(17)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (28)..(28)
<223> OTHER INFORMATION: n is
    7-(2-thienyl)-3H-imidazo[4,5-b]pyridine-3-yl

<400> SEQUENCE: 3
cagacccttt ttagccnatc gaactgcnat gagtgtgctt taaaagggt ctg    53

<210> SEQ ID NO 4
<211> LENGTH: 53
<212> TYPE: DNA

```
<213> ORGANISM: Artificial
<220> FEATURE:
<223> OTHER INFORMATION: Synthetic construct
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (28)..(28)
<223> OTHER INFORMATION: n is
      7-(2-thienyl)-3H-imidazo[4,5-b]pyridine-3-yl

<400> SEQUENCE: 4
caggctgtct ctagtcngtc gaactgtnat gagcgtgcta ggggagggt ctg           53

<210> SEQ ID NO 5
<211> LENGTH: 53
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (28)..(28)
<223> OTHER INFORMATION: n is
      7-(2-thienyl)-3H-imidazo[4,5-b]pyridine-3-yl

<400> SEQUENCE: 5
caggctgtct ctagtcagtc gaactgtnat gagcgtgcta ggggagggt ctg           53

<210> SEQ ID NO 6
<211> LENGTH: 53
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl

<400> SEQUENCE: 6
caggctgtct ctagtcngtc gaactgtaat gagcgtgcta ggggagggt ctg           53

<210> SEQ ID NO 7
<211> LENGTH: 53
<212> TYPE: DNA
<213> ORGANISM: Artificial
<220> FEATURE:
<223> OTHER INFORMATION: Synthetic construct

<400> SEQUENCE: 7
caggctgtct ctagtcagtc gaactgtaat gagcgtgcta ggggagggt ctg           53

<210> SEQ ID NO 8
<211> LENGTH: 37
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (20)..(20)
```

```
<223> OTHER INFORMATION: n is
      7-(2-thienyl)-3H-imidazo[4,5-b]pyridine-3-yl

<400> SEQUENCE: 8
ctctagtcng tcgaactgtn atgagcgtgc taggggg                          37

<210> SEQ ID NO 9
<211> LENGTH: 35
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (20)..(20)
<223> OTHER INFORMATION: n is
      7-(2-thienyl)-3H-imidazo[4,5-b]pyridine-3-yl

<400> SEQUENCE: 9
cggcggtcng tcgaactgtn atgagcgtgc cgccg                            35

<210> SEQ ID NO 10
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (20)..(20)
<223> OTHER INFORMATION: n is
      7-(2-thienyl)-3H-imidazo[4,5-b]pyridine-3-yl

<400> SEQUENCE: 10
cggcggtcng tcgaactgtn atgagcgtgc cgccgcgcgt agcg                  44

<210> SEQ ID NO 11
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (19)..(19)
<223> OTHER INFORMATION: n is
      7-(2-thienyl)-3H-imidazo[4,5-b]pyridine-3-yl

<400> SEQUENCE: 11
ggcggtcngt cgaactgtna tgagcgtgcc gcccgcgtag cg                    42

<210> SEQ ID NO 12
<211> LENGTH: 40
<212> TYPE: DNA
<213> ORGANISM: Artificial
<220> FEATURE:
```

```
<223> OTHER INFORMATION: Synthetic construct
<220> FEATURE:
<221> NAME/KEY: misc_feature
<222> LOCATION: (7)..(7)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl

<400> SEQUENCE: 12
gcggtcngtc gaactgtnat gagcgtgccg ccgcgtagcg                              40

<210> SEQ ID NO 13
<211> LENGTH: 38
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl

<400> SEQUENCE: 13
cggtcngtcg aactgtnatg agcgtgccgc gcgtagcg                                38

<210> SEQ ID NO 14
<211> LENGTH: 33
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (19)..(19)
<223> OTHER INFORMATION: n is
      7-(2-thienyl)-3H-imidazo[4,5-b]pyridine-3-yl

<400> SEQUENCE: 14
ggcggtcngt cgaactgtna tgagcgtgcc gcc                                     33

<210> SEQ ID NO 15
<211> LENGTH: 31
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (7)..(7)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl

<400> SEQUENCE: 15
```
gcggtcngtc gaactgtnat gagcgtgccg c                               31

<210> SEQ ID NO 16
<211> LENGTH: 29
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl

<400> SEQUENCE: 16
cggtcngtcg aactgtnatg agcgtgccg                                  29

<210> SEQ ID NO 17
<211> LENGTH: 51
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl

<400> SEQUENCE: 17
ggcccggctg gcatgtantc atgcctcctg gnctaaggtt tctaaagggt c          51

<210> SEQ ID NO 18
<211> LENGTH: 51
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, t, or none
<220> FEATURE:
<221> NAME/KEY: misc_feature
<222> LOCATION: (13)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl, A or none
<220> FEATURE:
<221> NAME/KEY: misc_feature
<222> LOCATION: (19)..(22)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, t, or none

```
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (46)..(51)
<223> OTHER INFORMATION: n is a, c, g, or t

<400> SEQUENCE: 18
nnnccggctn nnnnnnnnnn nnnnntcctg gnntaaggtt tctaannnnn n          51

<210> SEQ ID NO 19
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (25)..(25)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (26)..(26)
<223> OTHER INFORMATION: n is a, c, g, or t

<400> SEQUENCE: 19
nnnccggctc ggtatgcctc ctggnntaag gtttctaaag ggtc                  44

<210> SEQ ID NO 20
<211> LENGTH: 51
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl

<400> SEQUENCE: 20
ggcccggctg gcatgtantc atgcctcctg gnctaaggtt tctaaagggc c          51

<210> SEQ ID NO 21
<211> LENGTH: 51
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl

<400> SEQUENCE: 21
```
ggcccggctg gcatgtaatc atgcctcctg gnctaaggtt tctaaagggc c    51

<210> SEQ ID NO 22
<211> LENGTH: 51
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl

<400> SEQUENCE: 22
ggcccggctg gcatgtantc atgcctcctg gactaaggtt tctaaagggc c    51

<210> SEQ ID NO 23
<211> LENGTH: 51
<212> TYPE: DNA
<213> ORGANISM: Artificial
<220> FEATURE:
<223> OTHER INFORMATION: Synthetic construct

<400> SEQUENCE: 23
ggcccggctg gcatgtaatc atgcctcctg gactaaggtt tctaaagggc c    51

<210> SEQ ID NO 24
<211> LENGTH: 60
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl

<400> SEQUENCE: 24
ggcccggctg gcatgtantc atgcctcctg gnctaaggtt tctaaagggc ccgcgtagcg    60

<210> SEQ ID NO 25
<211> LENGTH: 53
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (25)..(25)
<223> OTHER INFORMATION: n is
      7-(2-thienyl)-3H-imidazo[4,5-b]pyridine-3-yl

<400> SEQUENCE: 25
ggcccggctg gcgaagcctc ctggnctaag gtttctaaag ggcccgcgta gcg    53

<210> SEQ ID NO 26
<211> LENGTH: 44
<212> TYPE: DNA
<213> ORGANISM: Artificial
<220> FEATURE:
<223> OTHER INFORMATION: Synthetic construct
<220> FEATURE:

```
<221> NAME/KEY: misc_feature
<222> LOCATION: (25)..(25)
<223> OTHER INFORMATION: n is
      7-(2-thienyl)-3H-imidazo[4,5-b]pyridine-3-yl

<400> SEQUENCE: 26
ggcccggctg gcgaagcctc ctggnctaag gtttctaaag ggcc                    44

<210> SEQ ID NO 27
<211> LENGTH: 31
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (13)..(13)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: n is
      7-(2-thienyl)-3H-imidazo[4,5-b]pyridine-3-yl

<400> SEQUENCE: 27
ggcgaagatc acnactaggg gncctcgagc c                                  31

<210> SEQ ID NO 28
<211> LENGTH: 31
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (22)..(22)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, t, or none
<220> FEATURE:
<221> NAME/KEY: misc_feature
<222> LOCATION: (29)..(31)
<223> OTHER INFORMATION: n is a, c, g, or t

<400> SEQUENCE: 28
nnnnnngatc acnnctaggg gnccnnnnnn n                                  31

<210> SEQ ID NO 29
<211> LENGTH: 33
<212> TYPE: DNA
<213> ORGANISM: Artificial
<220> FEATURE:
```

```
<223> OTHER INFORMATION: Synthetic construct
<220> FEATURE:
<221> NAME/KEY: misc_feature
<222> LOCATION: (15)..(15)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (24)..(24)
<223> OTHER INFORMATION: n is
      7-(2-thienyl)-3H-imidazo[4,5-b]pyridine-3-yl

<400> SEQUENCE: 29
gcggcgaaga tcacnactag gggncctcgc cgc                                33

<210> SEQ ID NO 30
<211> LENGTH: 33
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (15)..(15)
<223> OTHER INFORMATION: n is
      7-(2-thienyl)-3H-imidazo[4,5-b]pyridine-3-yl

<400> SEQUENCE: 30
gcggcgaaga tcacnactag gggacctcgc cgc                                33

<210> SEQ ID NO 31
<211> LENGTH: 33
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (24)..(24)
<223> OTHER INFORMATION: n is
      7-(2-thienyl)-3H-imidazo[4,5-b]pyridine-3-yl

<400> SEQUENCE: 31
gcggcgaaga tcacaactag gggncctcgc cgc                                33

<210> SEQ ID NO 32
<211> LENGTH: 33
<212> TYPE: DNA
<213> ORGANISM: Artificial
<220> FEATURE:
<223> OTHER INFORMATION: Synthetic construct

<400> SEQUENCE: 32
gcggcgaaga tcacaactag gggacctcgc cgc                                33

<210> SEQ ID NO 33
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (15)..(15)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (24)..(24)
<223> OTHER INFORMATION: n is
      7-(2-thienyl)-3H-imidazo[4,5-b]pyridine-3-yl
```

<400> SEQUENCE: 33
gcggcgaaga tcacnactag gggncctcgc cgccgcgtag cg                    42

<210> SEQ ID NO 34
<211> LENGTH: 49
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (33)..(33)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (44)..(44)
<223> OTHER INFORMATION: n is
     7-(2-thienyl)-3H-imidazo[4,5-b]pyridine-3-yl

<400> SEQUENCE: 34
aattttgacg ttaggggtgt tgtgccgtg agntgtaacg tcangaatt              49

<210> SEQ ID NO 35
<211> LENGTH: 34
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (26)..(26)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (30)..(34)
<223> OTHER INFORMATION: n is a, c, g, or t

<400> SEQUENCE: 35
nnnnnagggg tgtttgtgcc gtgagntgtn nnnn                             34

<210> SEQ ID NO 36
<211> LENGTH: 49
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (33)..(33)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (44)..(44)
<223> OTHER INFORMATION: n is
     7-(2-thienyl)-3H-imidazo[4,5-b]pyridine-3-yl

<400> SEQUENCE: 36
ggctttgacg ttaggggtgt tgtgccgtg agntgtaacg tcangagcc              49

<210> SEQ ID NO 37
<211> LENGTH: 49
<212> TYPE: DNA
<213> ORGANISM: Artificial

```
<220> FEATURE:
<223> OTHER INFORMATION: Synthetic construct
<220> FEATURE:
<221> NAME/KEY: misc_feature
<222> LOCATION: (33)..(33)
<223> OTHER INFORMATION: n is
      7-(2-thienyl)-3H-imidazo[4,5-b]pyridine-3-yl

<400> SEQUENCE: 37
ggctttgacg ttagggggtgt ttgtgccgtg agntgtaacg tcaagagcc          49

<210> SEQ ID NO 38
<211> LENGTH: 49
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (44)..(44)
<223> OTHER INFORMATION: n is
      7-(2-thienyl)-3H-imidazo[4,5-b]pyridine-3-yl

<400> SEQUENCE: 38
ggctttgacg ttagggggtgt ttgtgccgtg agatgtaacg tcangagcc          49

<210> SEQ ID NO 39
<211> LENGTH: 49
<212> TYPE: DNA
<213> ORGANISM: Artificial
<220> FEATURE:
<223> OTHER INFORMATION: Synthetic construct

<400> SEQUENCE: 39
ggctttgacg ttagggggtgt ttgtgccgtg agatgtaacg tcaagagcc          49

<210> SEQ ID NO 40
<211> LENGTH: 36
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (27)..(27)
<223> OTHER INFORMATION: n is
      7-(2-thienyl)-3H-imidazo[4,5-b]pyridine-3-yl

<400> SEQUENCE: 40
ggcgccaggg gtgtttgtgc cgtgagntgt ggcgcc                          36

<210> SEQ ID NO 41
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (27)..(27)
<223> OTHER INFORMATION: n is
      7-(2-thienyl)-3H-imidazo[4,5-b]pyridine-3-yl

<400> SEQUENCE: 41
ggcgccaggg gtgtttgtgc cgtgagntgt ggcgcccgcg tagcg                45

<210> SEQ ID NO 42
<211> LENGTH: 45
<212> TYPE: DNA
```

```
<213> ORGANISM: Artificial
<220> FEATURE:
<223> OTHER INFORMATION: Synthetic construct
<220> FEATURE:
<221> NAME/KEY: misc_feature
<222> LOCATION: (16)..(16)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (29)..(29)
<223> OTHER INFORMATION: n is
      7-(2-thienyl)-3H-imidazo[4,5-b]pyridine-3-yl

<400> SEQUENCE: 42
cctaggcagc ctgggntctc ttttagtcna gttcaatcgc ctagg            45

<210> SEQ ID NO 43
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (16)..(16)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (40)..(45)
<223> OTHER INFORMATION: n is a, c, g, or t

<400> SEQUENCE: 43
nnnnnncagc ctgggntntc tttnagtcna nttcantcgn nnnnn            45

<210> SEQ ID NO 44
<211> LENGTH: 43
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (15)..(15)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (28)..(28)
<223> OTHER INFORMATION: n is
```

7-(2-thienyl)-3H-imidazo[4,5-b]pyridine-3-yl

<400> SEQUENCE: 44
ccgcgcagcc tgggntctct tttagtcnag ttcaatcgcg cgg             43

<210> SEQ ID NO 45
<211> LENGTH: 52
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (15)..(15)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (28)..(28)
<223> OTHER INFORMATION: n is
      7-(2-thienyl)-3H-imidazo[4,5-b]pyridine-3-yl

<400> SEQUENCE: 45
ccgcgcagcc tgggntctct tttagtcnag ttcaatcgcg cggcgcgtag cg    52

<210> SEQ ID NO 46
<211> LENGTH: 43
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (15)..(15)
<223> OTHER INFORMATION: n is
      7-(2-thienyl)-3H-imidazo[4,5-b]pyridine-3-yl

<400> SEQUENCE: 46
ccgcgcagcc tgggntctct tttagtcaag ttcaatcgcg cgg             43

<210> SEQ ID NO 47
<211> LENGTH: 43
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (28)..(28)
<223> OTHER INFORMATION: n is
      7-(2-thienyl)-3H-imidazo[4,5-b]pyridine-3-yl

<400> SEQUENCE: 47
ccgcgcagcc tgggatctct tttagtcnag ttcaatcgcg cgg             43

<210> SEQ ID NO 48
<211> LENGTH: 43
<212> TYPE: DNA
<213> ORGANISM: Artificial
<220> FEATURE:
<223> OTHER INFORMATION: Synthetic construct

<400> SEQUENCE: 48
ccgcgcagcc tgggatctct tttagtcaag ttcaatcgcg cgg             43

<210> SEQ ID NO 49
<211> LENGTH: 49
<212> TYPE: DNA
<213> ORGANISM: Artificial

```
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (30)..(30)
<223> OTHER INFORMATION: n is
      7-(2-thienyl)-3H-imidazo[4,5-b]pyridine-3-yl

<400> SEQUENCE: 49
ccctcttaag tttatagntg tcttttggtn cctagggcgt tttaaaggg                49

<210> SEQ ID NO 50
<211> LENGTH: 49
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (25)..(29)
<223> OTHER INFORMATION: n is a, c, g, or t
<220> FEATURE:
<221> NAME/KEY: misc_feature
<222> LOCATION: (30)..(30)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (46)..(49)
<223> OTHER INFORMATION: n is a, c, g, or t

<400> SEQUENCE: 50
nnntcttaag tttananntn nnntnnnnnn nntngggcgt tttaannnn                49

<210> SEQ ID NO 51
<211> LENGTH: 49
<212> TYPE: DNA
<213> ORGANISM: Artificial
<220> FEATURE:
<223> OTHER INFORMATION: Synthetic construct
<220> FEATURE:
```

```
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (30)..(30)
<223> OTHER INFORMATION: n is
      7-(2-thienyl)-3H-imidazo[4,5-b]pyridine-3-yl

<400> SEQUENCE: 51
ccctcttaag tttatagntg tcttttggtn cctagggcgt tttaaaggg         49

<210> SEQ ID NO 52
<211> LENGTH: 58
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (30)..(30)
<223> OTHER INFORMATION: n is
      7-(2-thienyl)-3H-imidazo[4,5-b]pyridine-3-yl

<400> SEQUENCE: 52
ccctcttaag tttatagntg tcttttggtn cctagggcgt tttaaagggc gcgtagcg   58

<210> SEQ ID NO 53
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(24)
<223> OTHER INFORMATION: n is a, c, g, or t
<220> FEATURE:
<221> NAME/KEY: misc_feature
<222> LOCATION: (25)..(25)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (26)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 53
gagnnnnnnn nnnnnnnnnn nnnnnnnnnn nnnnnnnnnn nnnnn           45

<210> SEQ ID NO 54
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
```

```
<222> LOCATION: (4)..(23)
<223> OTHER INFORMATION: n is a, c, g, or t
<220> FEATURE:
<221> NAME/KEY: misc_feature
<222> LOCATION: (24)..(24)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (25)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 54
gacnnnnnnn nnnnnnnnnn nnnnnnnnnn nnnnnnnnnn nnnnn          45

<210> SEQ ID NO 55
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(22)
<223> OTHER INFORMATION: n is a, c, g, or t
<220> FEATURE:
<221> NAME/KEY: misc_feature
<222> LOCATION: (23)..(23)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (24)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 55
cagnnnnnnn nnnnnnnnnn nnnnnnnnnn nnnnnnnnnn nnnnn          45

<210> SEQ ID NO 56
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(21)
<223> OTHER INFORMATION: n is a, c, g, or t
<220> FEATURE:
<221> NAME/KEY: misc_feature
<222> LOCATION: (22)..(22)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (23)..(31)
<223> OTHER INFORMATION: n is a, c, g, or t
```

```
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 56
cacnnnnnnn nnnnnnnnnn nnnnnnnnnn nnnnnnnnnn nnnnn          45

<210> SEQ ID NO 57
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (22)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 57
aggnnnnnnn nnnnnnnnnn nnnnnnnnnn nnnnnnnnnn nnnnn          45

<210> SEQ ID NO 58
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(19)
<223> OTHER INFORMATION: n is a, c, g, or t
<220> FEATURE:
<221> NAME/KEY: misc_feature
<222> LOCATION: (20)..(20)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (21)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 58
```
ggannnnnnn nnnnnnnnnn nnnnnnnnnn nnnnnnnnnn nnnnn                45

<210> SEQ ID NO 59
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (20)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 59
gggnnnnnnn nnnnnnnnnn nnnnnnnnnn nnnnnnnnnn nnnnn                45

<210> SEQ ID NO 60
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (19)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 60
ggcnnnnnnn nnnnnnnnnn nnnnnnnnnn nnnnnnnnnn nnnnn                45

<210> SEQ ID NO 61
<211> LENGTH: 45
<212> TYPE: DNA
<213> ORGANISM: Artificial
<220> FEATURE:
<223> OTHER INFORMATION: Synthetic construct
<220> FEATURE:

<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (18)..(31)
<223> OTHER INFORMATION: n is a, c, g, or t
<220> FEATURE:
<221> NAME/KEY: misc_feature
<222> LOCATION: (32)..(32)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (33)..(45)
<223> OTHER INFORMATION: n is a, c, g, or t

<400> SEQUENCE: 61
ggtnnnnnnn nnnnnnnnn nnnnnnnnnn nnnnnnnnnn nnnnn    45

<210> SEQ ID NO 62
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (18)..(23)
<223> OTHER INFORMATION: n is a, c, g, or t
<220> FEATURE:
<221> NAME/KEY: misc_feature
<222> LOCATION: (24)..(24)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (25)..(45)
<223> OTHER INFORMATION: n is a, c, g, or t

<400> SEQUENCE: 62
cgannnnnnn nnnnnnnnnn nnnnnnnnnn nnnnnnnnnn nnnnn    45

<210> SEQ ID NO 63
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (18)..(24)

```
<223> OTHER INFORMATION: n is a, c, g, or t
<220> FEATURE:
<221> NAME/KEY: misc_feature
<222> LOCATION: (25)..(25)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (26)..(45)
<223> OTHER INFORMATION: n is a, c, g, or t

<400> SEQUENCE: 63
cggnnnnnnn nnnnnnnnnn nnnnnnnnnn nnnnnnnnnn nnnnn                      45

<210> SEQ ID NO 64
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(25)
<223> OTHER INFORMATION: n is a, c, g, or t
<220> FEATURE:
<221> NAME/KEY: misc_feature
<222> LOCATION: (26)..(26)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (27)..(45)
<223> OTHER INFORMATION: n is a, c, g, or t

<400> SEQUENCE: 64
cgcnnnnnnn nnnnnnnnnn nnnnnnnnnn nnnnnnnnnn nnnnn                      45

<210> SEQ ID NO 65
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(26)
<223> OTHER INFORMATION: n is a, c, g, or t
<220> FEATURE:
<221> NAME/KEY: misc_feature
<222> LOCATION: (27)..(27)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (28)..(45)
<223> OTHER INFORMATION: n is a, c, g, or t
```

```
<400> SEQUENCE: 65
cgtnnnnnnn nnnnnnnnn nnnnnnnnnn nnnnnnnnnn nnnnn          45

<210> SEQ ID NO 66
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(27)
<223> OTHER INFORMATION: n is a, c, g, or t
<220> FEATURE:
<221> NAME/KEY: misc_feature
<222> LOCATION: (28)..(28)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (29)..(45)
<223> OTHER INFORMATION: n is a, c, g, or t

<400> SEQUENCE: 66
tggnnnnnnn nnnnnnnnn nnnnnnnnnn nnnnnnnnnn nnnnn          45

<210> SEQ ID NO 67
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(28)
<223> OTHER INFORMATION: n is a, c, g, or t
<220> FEATURE:
<221> NAME/KEY: misc_feature
<222> LOCATION: (29)..(29)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (30)..(45)
<223> OTHER INFORMATION: n is a, c, g, or t

<400> SEQUENCE: 67
tgcnnnnnnn nnnnnnnnn nnnnnnnnnn nnnnnnnnnn nnnnn          45

<210> SEQ ID NO 68
<211> LENGTH: 45
<212> TYPE: DNA
<213> ORGANISM: Artificial
<220> FEATURE:
<223> OTHER INFORMATION: Synthetic construct
```

```
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(29)
<223> OTHER INFORMATION: n is a, c, g, or t
<220> FEATURE:
<221> NAME/KEY: misc_feature
<222> LOCATION: (30)..(30)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (31)..(45)
<223> OTHER INFORMATION: n is a, c, g, or t

<400> SEQUENCE: 68
acgnnnnnnn nnnnnnnnnn nnnnnnnnnn nnnnnnnnnn nnnnn                45

<210> SEQ ID NO 69
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (18)..(30)
<223> OTHER INFORMATION: n is a, c, g, or t
<220> FEATURE:
<221> NAME/KEY: misc_feature
<222> LOCATION: (31)..(31)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (32)..(45)
<223> OTHER INFORMATION: n is a, c, g, or t

<400> SEQUENCE: 69
gcannnnnnn nnnnnnnnnn nnnnnnnnnn nnnnnnnnnn nnnnn                45

<210> SEQ ID NO 70
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(20)
<223> OTHER INFORMATION: n is a, c, g, or t
<220> FEATURE:
<221> NAME/KEY: misc_feature
<222> LOCATION: (21)..(21)
<223> OTHER INFORMATION: n is
      7-(2-thienyl)-3H-imidazo[4,5-b]pyridine-3-yl
<220> FEATURE:
<221> NAME/KEY: misc_feature
```

<222> LOCATION: (22)..(27)
<223> OTHER INFORMATION: n is a, c, g, or t
<220> FEATURE:
<221> NAME/KEY: misc_feature
<222> LOCATION: (28)..(28)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (29)..(45)
<223> OTHER INFORMATION: n is a, c, g, or t

<400> SEQUENCE: 70
gcgnnnnnnn nnnnnnnnnn nnnnnnnnnn nnnnnnnnnn nnnnn        45

<210> SEQ ID NO 71
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(19)
<223> OTHER INFORMATION: n is a, c, g, or t
<220> FEATURE:
<221> NAME/KEY: misc_feature
<222> LOCATION: (20)..(20)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (21)..(27)
<223> OTHER INFORMATION: n is a, c, g, or t
<220> FEATURE:
<221> NAME/KEY: misc_feature
<222> LOCATION: (28)..(28)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (29)..(45)
<223> OTHER INFORMATION: n is a, c, g, or t

<400> SEQUENCE: 71
gccnnnnnnn nnnnnnnnnn nnnnnnnnnn nnnnnnnnnn nnnnn        45

<210> SEQ ID NO 72
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(19)
<223> OTHER INFORMATION: n is a, c, g, or t
<220> FEATURE:
<221> NAME/KEY: misc_feature
<222> LOCATION: (20)..(20)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (21)..(28)
<223> OTHER INFORMATION: n is a, c, g, or t
<220> FEATURE:
<221> NAME/KEY: misc_feature
<222> LOCATION: (29)..(29)
<223> OTHER INFORMATION: n is
    7-(2-thienyl)-3H-imidazo[4,5-b]pyridine-3-yl
<220> FEATURE:
<221> NAME/KEY: misc_feature
<222> LOCATION: (30)..(45)
<223> OTHER INFORMATION: n is a, c, g, or t

```
<400> SEQUENCE: 72
gctnnnnnnn nnnnnnnnn nnnnnnnnnn nnnnnnnnnn nnnnn              45

<210> SEQ ID NO 73
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (20)..(28)
<223> OTHER INFORMATION: n is a, c, g, or t
<220> FEATURE:
<221> NAME/KEY: misc_feature
<222> LOCATION: (29)..(29)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (30)..(45)
<223> OTHER INFORMATION: n is a, c, g, or t

<400> SEQUENCE: 73
ccannnnnnn nnnnnnnnnn nnnnnnnnnn nnnnnnnnnn nnnnn              45

<210> SEQ ID NO 74
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(18)
<223> OTHER INFORMATION: n is a, c, g, or t
<220> FEATURE:
<221> NAME/KEY: misc_feature
<222> LOCATION: (19)..(19)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (20)..(29)
<223> OTHER INFORMATION: n is a, c, g, or t
<220> FEATURE:
<221> NAME/KEY: misc_feature
<222> LOCATION: (30)..(30)
<223> OTHER INFORMATION: n is
      7-(2-thienyl)-3H-imidazo[4,5-b]pyridine-3-yl
<220> FEATURE:
<221> NAME/KEY: misc_feature
<222> LOCATION: (31)..(45)
<223> OTHER INFORMATION: n is a, c, g, or t

<400> SEQUENCE: 74
ccgnnnnnnn nnnnnnnnnn nnnnnnnnnn nnnnnnnnnn nnnnn              45

<210> SEQ ID NO 75
<211> LENGTH: 45
<212> TYPE: DNA
<213> ORGANISM: Artificial
<220> FEATURE:
```

```
<223> OTHER INFORMATION: Synthetic construct
<220> FEATURE:
<221> NAME/KEY: misc_feature
<222> LOCATION: (4)..(16)
<223> OTHER INFORMATION: n is a, c, g, or t
<220> FEATURE:
<221> NAME/KEY: misc_feature
<222> LOCATION: (17)..(17)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (18)..(29)
<223> OTHER INFORMATION: n is a, c, g, or t
<220> FEATURE:
<221> NAME/KEY: misc_feature
<222> LOCATION: (30)..(30)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (31)..(45)
<223> OTHER INFORMATION: n is a, c, g, or t

<400> SEQUENCE: 75
cccnnnnnnn nnnnnnnnnn nnnnnnnnnn nnnnnnnnnn nnnnn            45

<210> SEQ ID NO 76
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (4)..(17)
<223> OTHER INFORMATION: n is a, c, g, or t
<220> FEATURE:
<221> NAME/KEY: misc_feature
<222> LOCATION: (18)..(18)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (19)..(30)
<223> OTHER INFORMATION: n is a, c, g, or t
<220> FEATURE:
<221> NAME/KEY: misc_feature
<222> LOCATION: (31)..(31)
<223> OTHER INFORMATION: n is
     7-(2-thienyl)-3H-imidazo[4,5-b]pyridine-3-yl
<220> FEATURE:
<221> NAME/KEY: misc_feature
<222> LOCATION: (32)..(45)
<223> OTHER INFORMATION: n is a, c, g, or t

<400> SEQUENCE: 76
cctnnnnnnn nnnnnnnnnn nnnnnnnnnn nnnnnnnnnn nnnnn            45

<210> SEQ ID NO 77
<211> LENGTH: 25
<212> TYPE: DNA
<213> ORGANISM: Artificial
<220> FEATURE:
<223> OTHER INFORMATION: Primer

<400> SEQUENCE: 77
acgaccgttc tctaattttg acgtt                                  25

<210> SEQ ID NO 78
<211> LENGTH: 41
<212> TYPE: DNA
<213> ORGANISM: Artificial
```

```
<220> FEATURE:
<223> OTHER INFORMATION: Synthetic construct
<220> FEATURE:
<221> NAME/KEY: misc_feature
<222> LOCATION: (16)..(16)
<223> OTHER INFORMATION: n is Spacer C12 CE Phosphoramidite

<400> SEQUENCE: 78
tttttttttt tttttnacca aattattgcg atacagaccc t                    41

<210> SEQ ID NO 79
<211> LENGTH: 25
<212> TYPE: DNA
<213> ORGANISM: Artificial
<220> FEATURE:
<223> OTHER INFORMATION: Primer

<400> SEQUENCE: 79
accaaattat tgcgatacag accct                                      25

<210> SEQ ID NO 80
<211> LENGTH: 45
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (27)..(27)
<223> OTHER INFORMATION: N=7-(2-thienyl)-3H-imidazo[4,5-b]pyridine-3-yl

<400> SEQUENCE: 80
ggcgccaggg gtgtttgtgc cgtgagntgt ggcgcccgcg aagcg                45

<210> SEQ ID NO 81
<211> LENGTH: 26
<212> TYPE: DNA
<213> ORGANISM: Artificial
<220> FEATURE:
<223> OTHER INFORMATION: Synthetic construct

<400> SEQUENCE: 81
ggtggtggtg gttgtggtgg tggtgg                                     26

<210> SEQ ID NO 82
<211> LENGTH: 26
<212> TYPE: DNA
<213> ORGANISM: Artificial
<220> FEATURE:
<223> OTHER INFORMATION: Synthetic construct

<400> SEQUENCE: 82
cctcctcctc cttctcctcc tcctcc                                     26

<210> SEQ ID NO 83
<211> LENGTH: 9
<212> TYPE: DNA
<213> ORGANISM: Artificial
<220> FEATURE:
<223> OTHER INFORMATION: Synthetic construct

<400> SEQUENCE: 83 cgcgtagcg                                                        9
```